United States Patent
Coats et al.

(10) Patent No.: US 8,846,655 B2
(45) Date of Patent: Sep. 30, 2014

(54) 4-SUBSTITUTED-2-PHENOXY-PHENYLAMINE DELTA OPIOID RECEPTOR MODULATORS

(75) Inventors: Steven J. Coats, McDonough, GA (US); Haiyan Bian, Princeton, NJ (US); Chaozhong Cai, North Wales, PA (US); Bart L. DeCorte, Southampton, PA (US); Li Liu, Germantown, MD (US); Mark J. Macielag, Gwynedd Valley, PA (US); Scott L. Dax, Landenberg, PA (US); Philip M. Pitis, North Wales, PA (US); Peter J. Connolly, New Providence, NJ (US); Wei He, Audubon, PA (US)

(73) Assignee: Janssen Pharmaceutica, NV (BE)

( * ) Notice: Subject to any disclaimer, the term of this patent is extended or adjusted under 35 U.S.C. 154(b) by 295 days.

(21) Appl. No.: 13/503,433

(22) PCT Filed: Oct. 28, 2010

(86) PCT No.: PCT/US2010/054497
§ 371 (c)(1), (2), (4) Date: Aug. 1, 2012

(87) PCT Pub. No.: WO2011/053706
PCT Pub. Date: May 5, 2011

(65) Prior Publication Data
US 2012/0302541 A1 Nov. 29, 2012

Related U.S. Application Data

(60) Provisional application No. 61/256,412, filed on Oct. 30, 2009.

(51) Int. Cl.
| | |
|---|---|
| *A61K 31/40* | (2006.01) |
| *A61K 31/445* | (2006.01) |
| *A61K 31/4439* | (2006.01) |
| *A61K 31/4025* | (2006.01) |
| *A61K 31/506* | (2006.01) |
| *A61K 31/495* | (2006.01) |
| *C07D 211/56* | (2006.01) |
| *C07D 405/12* | (2006.01) |
| *C07D 207/09* | (2006.01) |
| *C07C 255/50* | (2006.01) |
| *C07C 211/48* | (2006.01) |
| *C07D 413/12* | (2006.01) |
| *C07D 401/12* | (2006.01) |
| *C07C 211/50* | (2006.01) |
| *C07D 205/04* | (2006.01) |
| *C07C 233/08* | (2006.01) |
| *C07C 233/11* | (2006.01) |
| *C07C 233/65* | (2006.01) |
| *C07D 451/04* | (2006.01) |
| *C07D 453/02* | (2006.01) |
| *C07D 409/12* | (2006.01) |

(52) U.S. Cl.
CPC ............ *C07D 401/12* (2013.01); *C07D 211/56* (2013.01); *C07D 405/12* (2013.01); *C07C 255/50* (2013.01); *C07C 211/48* (2013.01); *C07D 413/12* (2013.01); *C07D 207/09* (2013.01); *C07C 211/50* (2013.01); *C07D 205/04* (2013.01); *C07C 233/08* (2013.01); *C07C 233/11* (2013.01); *C07C 233/65* (2013.01); *C07D 451/04* (2013.01); *C07D 453/02* (2013.01); *C07D 409/12* (2013.01)
USPC ........ 514/210.2; 514/408; 514/331; 514/343; 514/422; 514/256; 514/255.03; 514/364; 514/304; 514/646; 514/305; 548/557; 548/517; 548/527; 548/950; 546/232; 546/124; 546/133; 544/333; 544/395; 564/443

(58) Field of Classification Search
None
See application file for complete search history.

(56) References Cited

U.S. PATENT DOCUMENTS 4,866,091 A * 9/1989 Matsuo et al. ................ 514/471

FOREIGN PATENT DOCUMENTS

| EP | 1833826 B1 | 5/2009 |
|---|---|---|
| WO | WO 2006/074388 A2 | 7/2006 |
| WO | WO 2008/032156 A1 | 3/2008 |

OTHER PUBLICATIONS

International Search Report dated Dec. 27, 2010 for corresponding Patent Application No. PCT/US2010/054497.
Evans, C.J.(1993), "Diversity Among the Opioid Receptors", in *Biological Basis of Substance Abuse*, eds. Koreman SG and Barchas J.D. (Oxford University Press, New York) pp. 31-48.
Gilbert, P. & Martin, W., "The Effects of Morphine- and Nalorphine-Like Drugs in the Nondependent, Morphine-Dependent and Cyclazocine-Dependent Chronic Spinal Dog", *J. Pharmacol Epx Ther.* 1976, vol. 198, pp. 66-82.

(Continued)

*Primary Examiner* — Yong Chu

(57) ABSTRACT

Disclosed are compounds, compositions and methods for treating various diseases, syndromes, conditions and disorders, including pain. Such compounds are represented by Formula I as follows:

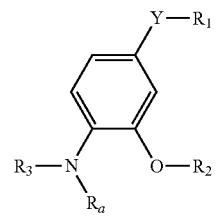

Formula I wherein $R_1$, $R_2$, $R_3$, $R_a$, and Y are defined herein.

24 Claims, No Drawings

(56) References Cited

OTHER PUBLICATIONS

Gross, R., et al., "Dynorphin A and c-AMP-dependent Protein Kinase Independently Regulate Neuronal Calcium Currents", *Pro Natl Acad Sci USA*, 1990, vol. 87, pp. 7025-7029.

Lord, J., et al., "Endogenous Opioid Peptides; Multiple Agonists and Receptors", *Nature*, 1977, vol. 11, pp. 308-314.

Mansour, A., et al., "Anatomy of CNS Opioid Receptors", Trends in Neurosci, 1988, vol. 11, pp. 308-314.

Pert, C., et al., Opiate Receptor: Demonstration in Nervous Tissue, Science (1973)179:1011-1014.

Sharma, S., et al., "Dual Regulation of Adenylate Cyclase Accounts for Narcotic Dependence and Tolerance", *Proc Natl Acad Sci USA*, 1975, vol. 72, pp. 3092-3096.

Wollemann, M., "Recent Developments in th Research of Opioid Receptor Subtype Molecular Characterization", *J. Neurchem* 1990, vol. 54, pp. 1095-1101.

\* cited by examiner

4-SUBSTITUTED-2-PHENOXY-PHENYLAMINE DELTA OPIOID RECEPTOR MODULATORS

CROSS REFERENCE TO RELATED APPLICATIONS

This application is a national stage application of Patent Application No. PCT/US2010/054497, filed Oct. 28, 2010, which in turn claims the benefit of U.S. Provisional Patent Application No. 61/256,412 filed Oct. 30, 2009. The complete disclosures of the aforementioned related patent applications are hereby incorporated herein by reference for all purposes.

FIELD OF THE INVENTION

The present invention is directed to novel opioid receptor modulators of Formula (I). The invention further relates to methods for preparing such compounds, pharmaceutical compositions containing them, and their use in the treatment of opioid modulated disorders.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mention, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

There is a continuing need for new opioid receptor modulators as analgesics. There is a further need for delta and mu opioid receptor agonists as analgesics having reduced side effects. There is a further need for mu opioid receptor agonists as analgesics having reduced side effects for the treatment of pain, immune function, esophageal reflux, and cough. There is also a need for delta opioid receptor agonists as analgesic agents, agents for the treatment of respiratory diseases, cardiovascular agents, agents for treating urological dysfunction, and agents for the treatment of neurological and psychiatric conditions. There is further need for dual delta opioid receptor/mu opioid receptor agonists.

SUMMARY OF THE INVENTION

The present invention is directed to a compound of Formula I

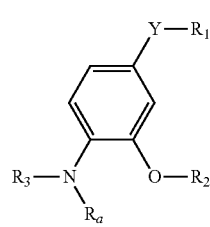

Formula I wherein
R₁ is selected from the group consisting of
  i) phenyl optionally substituted with one to two substituents independently selected from the group consisting of $C_{1-4}$alkyl, $C_{1-4}$alkoxy, $C_{1-4}$alkylthio, hydroxy, di($C_{1-4}$alkyl)aminocarbonyl, chloro, and fluoro; such that only one di($C_{1-4}$alkyl)aminocarbonyl is present;
  ii) naphthyl;
  iii) pyridinyl optionally substituted with one substituent selected from the group consisting of $C_{1-4}$alkyl, $C_{1-4}$alkoxy, $C_{1-4}$alkylthio, hydroxy, fluoro, chloro, and cyano;
  iv) pyrimidin-5-yl;
  v) furanyl;
  vi) thienyl;
  vii) 5-oxo-4,5-dihydro-[1,2,4]oxadiazol-3-yl; and
  viii) di($C_{1-2}$alkyl)aminocarbonyl;
  with the proviso that when R₁ is 5-oxo-4,5-dihydro-[1,2,4]oxadiazol-3-yl, Y is a bond;
Y is ethyl, vinyl, or a bond;
or, Y is O when R₁ is an optionally substituted phenyl;
R₂ is phenyl optionally substituted with one to two substituents independently selected from the group consisting of $C_{1-4}$alkyl, $C_{1-4}$alkoxy, fluoro, chloro, cyano, trifluoromethoxy, and hydroxy;
or, R₂ is phenyl substituted with one aminocarbonyl, di($C_{1-4}$alkyl)aminocarbonyl, $C_{1-4}$alkoxycarbonyl, or carboxy substituent;
R₃ is selected from the group consisting of
  i) 3-amino-cyclohexyl;
  ii) 4-amino-cyclohexyl;
  iii) piperidin-3-yl;
  iv) piperidin-4-yl;
  v) pyrrolidin-2-ylmethyl wherein pyrrolidin-2-yl is optionally substituted at the 3- or 4-position with one to two fluoro substituents;
  vi) azetidin-3-ylmethyl;
  vii) 2-(N-methylamino)ethyl;
  viii) 3-hydroxy-2-amino-propyl;
  ix) piperidin-3-ylmethyl;
  x) 1-azabicyclo[2.2.2]octan-3-yl; and
  xi) 8-azabicyclo[3.2.1]octan-3-yl;
  or, R₃ is taken with $R_a$ and the nitrogen atom to which they are both attached to form piperazinyl optionally substituted with 4-$C_{1-4}$alkyl;
$R_a$ is hydrogen, 2-(N-methylamino)ethyl, or $C_{1-2}$alkyl optionally substituted with azetidin-3-yl;
and enantiomers, diastereomers, solvates, and pharmaceutically acceptable salts thereof.

The present invention is also directed to a pharmaceutical composition comprising a pharmaceutically acceptable carrier and a compound of Formula (I) or a pharmaceutically acceptable salt form thereof.

Also provided are processes for making a pharmaceutical composition comprising mixing a compound of Formula (I) and a pharmaceutically acceptable carrier.

The present invention is further directed to methods for treating or ameliorating an opioid receptor-modulated disorder. In particular, the methods of the present invention are directed to treating or ameliorating an opioid receptor-modulated disorder including, but not limited to, inflammatory pain, centrally mediated pain, peripherally mediated pain, visceral pain, structural related pain, cancer/pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

The present invention also provides methods for producing the instant compounds and pharmaceutical compositions and medicaments thereof.

As used herein, the following terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

With reference to substituents, the term "independently" means that when more than one of such substituent is possible, such substituents may be the same or different from each other. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an -Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as ($C_{1-6}$alkyl)₂-amino- the $C_{1-6}$alkyl groups of the dialkylamino may be the same or different.

"Halogenated alkyl" refers to a saturated branched or straight chain alkyl radical derived by removal of 1 hydrogen atom from the parent alkane; the parent alkyl chain contains from 1 to 8 carbon atoms with 1 or more hydrogen atoms replaced with halogen atoms up to and including replacement of all hydrogen atoms with halogen. Preferred halogenated alkyl groups include trifluoromethyl substituted alkyls, difluoromethyl substituted alkyls, and perfluorinated alkyls; more preferred fluorinated alkyls include trifluoromethyl and difluoromethyl.

"Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, monocyclic or polycyclic hydrocarbon of from 3 to 20 carbon atom members (preferably from 3 to 14 carbon atom members). Examples of such groups include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), or a 5 or 6 membered heteroaryl ring (containing one of O, S or N and, optionally, one additional nitrogen) to form a heteroaryl fused cycloalkyl.

The term "heterocyclyl" refers to a nonaromatic monocyclic ring of 5 to 10 members in which 1 to 4 members are nitrogen or a nonaromatic monocyclic ring of 5 to 10 members in which zero, one or two members are nitrogen and up to two members are oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzofused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinoxalinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

The term "vinyl" refers to a two-carbon unsaturated linker in which the unsaturation is a double bond between said two carbon atoms. When two substituents occur on the vinyl linker, the substituents are understood to be bound on adjacent carbon atoms, such that the substituents are 1,2-configured.

The term "oxo" whether used alone or as part of a substituent group refers to an O= to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$ $C_{3-6}$, $C_{4-6}$, $C_{5-6}$, $C_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

Throughout this disclosure, the terminal portion of the designated side chain is described first, followed by the adjacent functionality toward the point of attachment. Thus, for example, a "phenyl($C_{1-6}$)alkylaminocarbonyl($C_{1-6}$)alkyl" substituent refers to a group of the formula

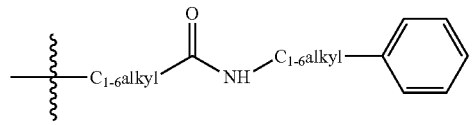

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

For purposes of the present invention, the term "opioid receptor-modulated" is used to refer to the condition of being affected by the modulation of an opioid receptor, including but not limited to, the state of being mediated by the opioid receptor.

Embodiments of the present invention include those compounds of Formula (I)

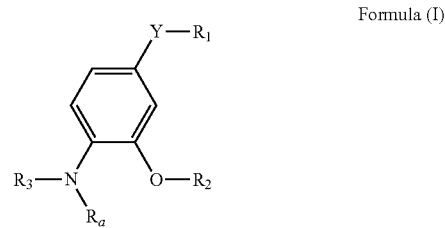

Formula (I)

wherein
a) R$_1$ is selected from the group consisting of
   i) phenyl optionally substituted with one to two substituents independently selected from the group consisting of C$_{1-4}$alkoxy, di(C$_{1-4}$-alkyl)aminocarbonyl, and fluoro; such that only one di(C$_{1-4}$-alkyl)aminocarbonyl is present;
   ii) naphthyl;
   iii) pyridinyl optionally substituted with one substituent selected from the group consisting of C$_{1-4}$ alkyl, C$_{1-4}$alkoxy, C$_{1-4}$alkylthio, fluoro, and cyano;
   iv) pyrimidin-5-yl;
   v) furanyl;
   vi) thienyl; and
   vii) di(C$_{1-2}$alkyl)aminocarbonyl;
b) R$_1$ is selected from the group consisting of
   i) phenyl optionally substituted with one substituent selected from the group consisting of C$_{1-4}$alkoxy, di(C$_{1-4}$alkyl)aminocarbonyl, and fluoro;
   ii) pyridinyl optionally substituted with one substituent selected from the group consisting of C$_{1-4}$alkyl, C$_{1-4}$alkoxy, C$_{1-4}$alkylthio, fluoro, and cyano;
   iii) pyrimidin-5-yl; and
   iv) di(C$_{1-2}$alkyl)aminocarbonyl;
c) R$_1$ is selected from the group consisting of
   i) phenyl optionally substituted with one methoxy substituent;
   ii) pyridinyl optionally substituted with one substituent selected from the group consisting of C$_{1-4}$alkyl, C$_{1-4}$alkoxy, C$_{1-4}$alkylthio, fluoro, and cyano;
   iii) pyrimidin-5-yl; and
   iv) di(C$_{1-2}$alkyl)aminocarbonyl;
d) Y is vinyl or a bond; or, Y is O when R$_1$ is an optionally substituted phenyl;
e) Y is vinyl or a bond;
f) R$_2$ is phenyl optionally substituted with one to two substituents independently selected from the group consisting of C$_{1-4}$alkyl, C$_{1-4}$alkoxy, fluoro, chloro, and hydroxy; or, R$_2$ is phenyl substituted with one aminocarbonyl or di(C$_{1-4}$alkyl)aminocarbonyl substituent;
g) R$_2$ is phenyl optionally substituted with one to two substituents independently selected from the group consisting of C$_{1-4}$alkyl, C$_{1-4}$alkoxy, and hydroxy; or, R$_2$ is phenyl substituted with one aminocarbonyl or di(C$_{1-4}$alkyl)aminocarbonyl substituent;
h) R$_2$ is phenyl optionally substituted with one substituent independently selected from the group consisting of methoxy, hydroxy, aminocarbonyl, and di(C$_{1-4}$alkyl)aminocarbonyl;
i) R$_3$ is selected from the group consisting of
   i) 3-amino-cyclohexyl;
   ii) 4-amino-cyclohexyl;
   iii) pyrrolidin-2-ylmethyl wherein pyrrolidin-2-yl is optionally substituted at the 3- or 4-position with one to two fluoro substituents;
   iv) 2-(N-methylamino)ethyl;
   v) piperidin-3-ylmethyl; and
   vi) 1-azabicyclo[2.2.2]octan-3-yl; or, R$_3$ is taken with R$_a$ and the nitrogen atom to which they are both attached to form piperazinyl;
j) R$_3$ is selected from the group consisting of
   i) 3-amino-cyclohexyl;
   ii) 4-amino-cyclohexyl; and
   iii) pyrrolidin-2-ylmethyl wherein pyrrolidin-2-yl is optionally substituted at the 3- or 4-position with one fluoro substituent; or, R$_3$ is taken with R$_a$ and the nitrogen atom to which they are both attached to form piperazinyl;
k) R$_a$ is hydrogen or C$_{1-2}$alkyl;
l) R$_a$ is hydrogen;
   and any combination of embodiments a) through l) above, provided that it is understood that combinations in which different embodiments of the same substituent would be combined are excluded; and enantiomers, diastereomers, solvates, and pharmaceutically acceptable salts thereof.

A further embodiment of the present invention includes compounds of Formula (I)

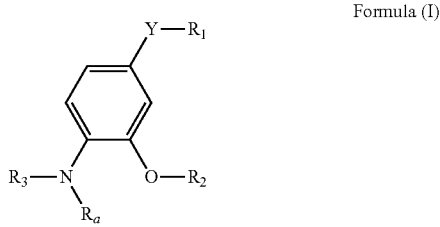

Formula (I)

wherein
R$_1$ is selected from the group consisting of
   i) phenyl optionally substituted with one to two substituents independently selected from the group consisting of C$_{1-4}$alkoxy, di(C$_{1-4}$-alkyl)aminocarbonyl, and fluoro; such that only one di(C$_{1-4}$-alkyl)aminocarbonyl is present;
   ii) naphthyl;
   iii) pyridinyl optionally substituted with one substituent selected from the group consisting of C$_{1-4}$alkyl, C$_{1-4}$alkoxy, C$_{1-4}$alkylthio, fluoro, and cyano;
   iv) pyrimidin-5-yl;
   v) furanyl;
   vi) thienyl; and
   vii) di(C$_{1-2}$alkyl)aminocarbonyl;
Y is vinyl or a bond; or, Y is O when R$_1$ is an optionally substituted phenyl;
R$_2$ is phenyl optionally substituted with one to two substituents independently selected from the group consisting of C$_{1-4}$alkyl, C$_{1-4}$alkoxy, fluoro, chloro, and hydroxy;
or, R$_2$ is phenyl substituted with one aminocarbonyl or di(C$_{1-4}$alkyl)aminocarbonyl substituent;
R$_3$ is selected from the group consisting of
   i) 3-amino-cyclohexyl;
   ii) 4-amino-cyclohexyl;
   iii) pyrrolidin-2-ylmethyl wherein pyrrolidin-2-yl is optionally substituted at the 3- or 4-position with one to two fluoro substituents;
   v) 2-(N-methylamino)ethyl;
   vi) piperidin-3-ylmethyl; and
   vii) 1-azabicyclo[2.2.2]octan-3-yl; or, R$_3$ is taken with R$_a$ and the nitrogen atom to which they are both attached to form piperazinyl;
R$_a$ is hydrogen or C$_{1-2}$alkyl;
and enantiomers, diastereomers, solvates, and pharmaceutically acceptable salts thereof.

A further embodiment of the present invention includes compounds of Formula (I)

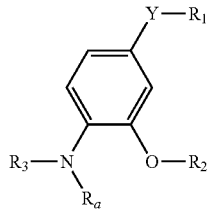

Formula (I)

wherein
$R_1$ is selected from the group consisting of
i) phenyl optionally substituted with one substituent selected from the group consisting of $C_{1-4}$alkoxy, di($C_{1-4}$alkyl)aminocarbonyl, and fluoro;
ii) pyridinyl optionally substituted with one substituent selected from the group consisting of $C_{1-4}$alkyl, $C_{1-4}$alkoxy, $C_{1-4}$alkylthio, fluoro, and cyano;
iii) pyrimidin-5-yl; and
iv) di($C_{1-2}$alkyl)aminocarbonyl;
Y is vinyl or a bond;
$R_2$ is phenyl optionally substituted with one to two substituents independently selected from the group consisting of $C_{1-4}$alkyl, $C_{1-4}$alkoxy, and hydroxy;
or, $R_2$ is phenyl substituted with one aminocarbonyl or di($C_{1-4}$alkyl)aminocarbonyl substituent;
$R_3$ is selected from the group consisting of
i) 3-amino-cyclohexyl;
ii) 4-amino-cyclohexyl;
iii) pyrrolidin-2-ylmethyl wherein pyrrolidin-2-yl is optionally substituted at a carbon atom with one to two fluoro substituents;
v) 2-(N-methylamino)ethyl;
vi) piperidin-3-ylmethyl; and
vii) 1-azabicyclo[2.2.2]octan-3-yl;
or, $R_3$ is taken with $R_a$ and the nitrogen atom to which they are both attached to form piperazinyl;
$R_a$ is hydrogen;
and enantiomers, diastereomers, solvates, and pharmaceutically acceptable salts thereof.

A further embodiment of the present invention includes compounds of Formula (I)

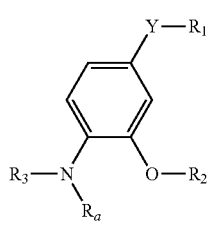

Formula (I)

wherein
$R_1$ is selected from the group consisting of
i) phenyl optionally substituted with one methoxy substituent;
ii) pyridinyl optionally substituted with one substituent selected from the group consisting of $C_{1-4}$alkyl, $C_{1-4}$alkoxy, $C_{1-4}$alkylthio, fluoro, and cyano;
iii) pyrimidin-5-yl; and
iv) di($C_{1-2}$alkyl)aminocarbonyl;

Y is vinyl or a bond;
$R_2$ is phenyl optionally substituted with one substituent independently selected from the group consisting of methoxy, hydroxy, aminocarbonyl, and di($C_{1-4}$-alkyl)aminocarbonyl;
$R_3$ is selected from the group consisting of
i) 3-amino-cyclohexyl;
ii) 4-amino-cyclohexyl;
iii) pyrrolidin-2-ylmethyl wherein pyrrolidin-2-yl is optionally substituted at a carbon atom with one fluoro substituent;
or, $R_3$ is taken with $R_a$ and the nitrogen atom to which they are both attached to form piperazinyl;
$R_a$ is hydrogen;
and enantiomers, diastereomers, solvates, and pharmaceutically acceptable salts thereof.

A further embodiment of the present invention includes compounds of Formula (I)

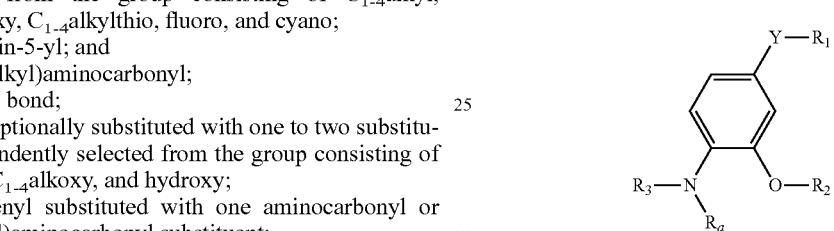

Formula (I)

selected from the group consisting of
a compound wherein $R_1$ is 2-(N,N-diethylaminocarbonyl), Y is (E)-vinyl, $R_2$ is 4-methoxy-phenyl, $R_3$ is pyrrolidin-2-ylmethyl, and $R_a$ is H; (2S)
a compound wherein $R_1$ is 2-(N,N-diethylaminocarbonyl), Y is ethyl, $R_2$ is 4-methoxy-phenyl, $R_3$ is pyrrolidin-2-ylmethyl, and $R_a$ is H; (2S)
a compound wherein $R_1$ is 2-(4-methoxy-phenyl), Y is ethyl, $R_2$ is 4-methoxy-phenyl, $R_3$ is pyrrolidin-2-ylmethyl, and $R_a$ is H; (2S)
a compound wherein $R_1$ is 2-(3-methoxy-phenyl), Y is ethyl, $R_2$ is 4-methoxy-phenyl, $R_3$ is pyrrolidin-2-ylmethyl, and $R_a$ is H; (2S)
a compound wherein $R_1$ is 2-phenyl, Y is ethyl, $R_2$ is 4-methoxy-phenyl, $R_3$ is pyrrolidin-2-ylmethyl, and $R_a$ is H; (2S)
a compound wherein $R_1$ is 2-(4-fluoro-phenyl), Y is ethyl, $R_2$ is 4-methoxy-phenyl, $R_3$ is pyrrolidin-2-ylmethyl, and $R_a$ is H; (2S)
a compound wherein $R_1$ is 2-(3-fluoro-phenyl), Y is ethyl, $R_2$ is 4-methoxy-phenyl, $R_3$ is pyrrolidin-2-ylmethyl, and $R_a$ is H; (2S)
a compound wherein $R_1$ is 2-[3-(N,N-diethylaminocarbonyl)phenyl], Y is ethyl, $R_2$ is 4-methoxy-phenyl, $R_3$ is pyrrolidin-2-ylmethyl, and $R_a$ is H; (2S)
a compound wherein $R_1$ is N,N-diethylaminocarbonyl, Y is a bond, $R_2$ is phenyl, $R_3$ is pyrrolidin-2-ylmethyl, and $R_a$ is H; (2S)
a compound wherein $R_1$ is N,N-diethylaminocarbonyl, Y is a bond, $R_2$ is 4-methoxy-phenyl, $R_3$ is pyrrolidin-2-ylmethyl, and $R_a$ is H; (2S)
a compound wherein $R_1$ is N,N-diethylaminocarbonyl, Y is a bond, $R_2$ is 2-methoxy-phenyl, $R_3$ is pyrrolidin-2-ylmethyl, and $R_a$ is H; (2S)
a compound wherein $R_1$ is phenyl, Y is a bond, $R_2$ is 4-cyano-phenyl, $R_3$ is pyrrolidin-2-ylmethyl, and $R_a$ is H; (2S)

a compound wherein $R_1$ is phenyl, Y is a bond, $R_2$ is 3-cyano-phenyl, $R_3$ is pyrrolidin-2-ylmethyl, and $R_a$ is H; (2S)

a compound wherein $R_1$ is phenyl, Y is a bond, $R_2$ is phenyl, $R_3$ is pyrrolidin-2-ylmethyl, and $R_a$ is H; (2S)

a compound wherein $R_1$ is phenyl, Y is a bond, $R_2$ is 3-methoxy-phenyl, $R_3$ is pyrrolidin-2-ylmethyl, and $R_a$ is H; (2S)

a compound wherein $R_1$ is phenyl, Y is a bond, $R_2$ is 4-fluoro-phenyl, $R_3$ is pyrrolidin-2-ylmethyl, and $R_a$ is H; (2S)

a compound wherein $R_1$ is phenyl, Y is a bond, $R_2$ is 4-trifluoromethoxy-phenyl, $R_3$ is pyrrolidin-2-ylmethyl, and $R_a$ is H; (2S)

a compound wherein $R_1$ is phenyl, Y is a bond, $R_2$ is 2,6-dichloro-phenyl, $R_3$ is pyrrolidin-2-ylmethyl, and $R_a$ is H; (2S)

a compound wherein $R_1$ is phenyl, Y is a bond, $R_2$ is 4-methoxy-phenyl, $R_3$ is 2-(N-methylamino)ethyl, and $R_a$ is H;

a compound wherein $R_1$ is phenyl, Y is a bond, $R_2$ is 4-methoxycarbonyl-phenyl, $R_3$ is pyrrolidin-2-ylmethyl, and $R_a$ is H; (2S)

a compound wherein $R_1$ is phenyl, Y is a bond, $R_2$ is 3-methoxycarbonyl-phenyl, $R_3$ is pyrrolidin-2-ylmethyl, and $R_a$ is H; (2S)

a compound wherein $R_1$ is phenyl, Y is a bond, $R_2$ is 2,4-dichloro-phenyl, $R_3$ is pyrrolidin-2-ylmethyl, and $R_a$ is H; (2S)

a compound wherein $R_1$ is phenyl, Y is a bond, $R_2$ is 4-methoxy-phenyl, $R_3$ is piperidin-4-yl, and $R_a$ is H;

a compound wherein $R_1$ is 5-cyano-pyridin-3-yl, Y is a bond, $R_2$ is 4-methoxy-phenyl, $R_3$ is 4-fluoro-pyrrolidin-2-ylmethyl, and $R_a$ is H; (2S,4R)

a compound wherein $R_1$ is 5-fluoro-pyridin-3-yl, Y is a bond, $R_2$ is 4-methoxy-phenyl, $R_3$ is 4-fluoro-pyrrolidin-2-ylmethyl, and $R_a$ is H; (2S,4R)

a compound wherein $R_1$ is 5-methylthio-pyridin-3-yl, Y is a bond, $R_2$ is 4-methoxy-phenyl, $R_3$ is 4-fluoro-pyrrolidin-2-ylmethyl, and $R_a$ is H; (2S,4R)

a compound wherein $R_1$ is 5-methoxy-pyridin-3-yl, Y is a bond, $R_2$ is 4-methoxy-phenyl, $R_3$ is 4-fluoro-pyrrolidin-2-ylmethyl, and $R_a$ is H; (2S,4R)

a compound wherein $R_1$ is 5-methyl-pyridin-3-yl, Y is a bond, $R_2$ is 4-methoxy-phenyl, $R_3$ is 4-fluoro-pyrrolidin-2-ylmethyl, and $R_a$ is H; (2S,4R)

a compound wherein $R_1$ is phenyl, Y is a bond, $R_2$ is 4-aminocarbonyl-phenyl, $R_3$ is pyrrolidin-2-ylmethyl, and $R_a$ is H; (2S)

a compound wherein $R_1$ is phenyl, Y is a bond, $R_2$ is 3-aminocarbonyl-phenyl, $R_3$ is pyrrolidin-2-ylmethyl, and $R_a$ is H; (2S)

a compound wherein $R_1$ is phenyl, Y is a bond, $R_2$ is 4-carboxy-phenyl, $R_3$ is pyrrolidin-2-ylmethyl, and $R_a$ is H; (2S)

a compound wherein $R_1$ is phenyl, Y is a bond, $R_2$ is 3-carboxy-phenyl, $R_3$ is pyrrolidin-2-ylmethyl, and $R_a$ is H; (2S)

a compound wherein $R_1$ is phenyl, Y is a bond, $R_2$ is 4-(N,N-diethylaminocarbonyl)phenyl, $R_3$ is pyrrolidin-2-ylmethyl, and $R_a$ is H; (2S)

a compound wherein $R_1$ is phenyl, Y is a bond, $R_2$ is 3-(N,N-diethylaminocarbonyl)phenyl, $R_3$ is pyrrolidin-2-ylmethyl, and $R_a$ is H; (2S)

a compound wherein $R_1$ is phenyl, Y is a bond, $R_2$ is 4-methoxy-phenyl, $R_3$ is pyrrolidin-2-ylmethyl, and $R_a$ is H; (2S)

a compound wherein $R_1$ is naphthalen-2-yl, Y is a bond, $R_2$ is 4-methoxy-phenyl, $R_3$ is pyrrolidin-2-ylmethyl, and $R_a$ is H; (2S)

a compound wherein $R_1$ is naphthalen-1-yl, Y is a bond, $R_2$ is 4-methoxy-phenyl, $R_3$ is pyrrolidin-2-ylmethyl, and $R_a$ is H; (2S)

a compound wherein $R_1$ is pyridin-4-yl, Y is a bond, $R_2$ is 4-methoxy-phenyl, $R_3$ is pyrrolidin-2-ylmethyl, and $R_a$ is H; (2S)

a compound wherein $R_1$ is pyridin-3-yl, Y is a bond, $R_2$ is 4-methoxy-phenyl, $R_3$ is pyrrolidin-2-ylmethyl, and $R_a$ is H; (2S)

a compound wherein $R_1$ is furan-3-yl, Y is a bond, $R_2$ is 4-methoxy-phenyl, $R_3$ is pyrrolidin-2-ylmethyl, and $R_a$ is H; (2S)

a compound wherein $R_1$ is thiophen-3-yl, Y is a bond, $R_2$ is 4-methoxy-phenyl, $R_3$ is pyrrolidin-2-ylmethyl, and $R_a$ is H; (2S)

a compound wherein $R_1$ is pyrimidin-5-yl, Y is a bond, $R_2$ is 4-methoxy-phenyl, $R_3$ is pyrrolidin-2-ylmethyl, and $R_a$ is H; (2S)

a compound wherein $R_1$ is 5-fluoro-pyridin-3-yl, Y is a bond, $R_2$ is 4-methoxy-phenyl, $R_3$ is pyrrolidin-2-ylmethyl, and $R_a$ is H; (2S)

a compound wherein $R_1$ is 5-cyano-pyridin-3-yl, Y is a bond, $R_2$ is 4-methoxy-phenyl, $R_3$ is pyrrolidin-2-ylmethyl, and $R_a$ is H; (2S)

a compound wherein $R_1$ is pyridin-3-yl, Y is a bond, $R_2$ is 4-hydroxy-phenyl, $R_3$ is pyrrolidin-2-ylmethyl, and $R_a$ is H; (2S)

a compound wherein $R_1$ is phenyl, Y is a bond, $R_2$ is 4-methoxy-phenyl, $R_3$ is taken with $R_a$ and the nitrogen atom to which they are both attached to form piperazin-1-yl;

a compound wherein $R_1$ is phenyl, Y is a bond, $R_2$ is 4-methoxy-phenyl, $R_3$ is taken with $R_a$ and the nitrogen atom to which they are both attached to form 4-methyl-piperazin-1-yl;

a compound wherein $R_1$ is 5-oxo-4,5-dihydro-[1,2,4]oxadiazol-3-yl, Y is a bond, $R_2$ is 4-methoxy-phenyl, $R_3$ is pyrrolidin-2-ylmethyl, and $R_a$ is H; (2S)

a compound wherein $R_1$ is pyridin-3-yl, Y is a bond, $R_2$ is 4-methoxy-phenyl, $R_3$ is pyrrolidin-2-ylmethyl, and $R_a$ is ethyl; (2S)

a compound wherein $R_1$ is 5-fluoro-pyridin-3-yl, Y is a bond, $R_2$ is 4-methoxy-phenyl, $R_3$ is pyrrolidin-2-ylmethyl, and $R_a$ is ethyl; (2S)

a compound wherein $R_1$ is pyrimidin-5-yl, Y is a bond, $R_2$ is 4-methoxy-phenyl, $R_3$ is pyrrolidin-2-ylmethyl, and $R_a$ is ethyl; (2S)

a compound wherein $R_1$ is 5-cyano-pyridin-3-yl, Y is a bond, $R_2$ is 4-methoxy-phenyl, $R_3$ is pyrrolidin-2-ylmethyl, and $R_a$ is ethyl; (2S)

a compound wherein $R_1$ is 4-methoxy-phenyl, Y is O, $R_2$ is 4-methoxy-phenyl, $R_3$ is pyrrolidin-2-ylmethyl, and $R_a$ is H; (2S)

a compound wherein $R_1$ is 4-methoxy-phenyl, Y is O, $R_2$ is 4-methoxy-phenyl, $R_3$ is piperidin-3-yl, and $R_a$ is H; racemic a compound wherein $R_1$ is 4-methoxy-phenyl, Y is O, $R_2$ is 4-methoxy-phenyl, $R_3$ is 3-hydroxy-2(R)-amino-propyl, and $R_a$ is H;

a compound wherein $R_1$ is 4-methoxy-phenyl, Y is O, $R_2$ is 4-methoxy-phenyl, $R_3$ is piperidin-4-yl, and $R_a$ is H;

a compound wherein $R_1$ is 4-methoxy-phenyl, Y is O, $R_2$ is 4-methoxy-phenyl, $R_3$ is 8-azabicyclo[3.2.1]octan-3-yl, and $R_a$ is H; mixture of endo/exo isomers a compound wherein $R_1$ is 4-methoxy-phenyl, Y is O, $R_2$ is 4-methoxy-phenyl, $R_3$ is azetidin-3-yl-methyl, and $R_a$ is H;

a compound wherein $R_1$ is 4-methoxy-phenyl, Y is O, $R_2$ is 4-methoxy-phenyl, $R_3$ is azetidin-3-yl-methyl, and $R_a$ is azetidin-3-yl-methyl;

a compound wherein R₁ is 4-methoxy-phenyl, Y is O, R₂ is 4-methoxy-phenyl, R₃ is 1-azabicyclo[2.2.2]octan-3-yl, and R_a is H; mixture of endo/exo isomers a compound wherein R₁ is 4-methoxy-phenyl, Y is O, R₂ is 4-methoxy-phenyl, R₃ is piperidin-3-ylmethyl, and R_a is H; racemic a compound wherein R₁ is 4-methoxy-phenyl, Y is O, R₂ is 4-methoxy-phenyl, R₃ is 3-amino-cyclohexyl, and R_a is H; mixture of 4 isomers a compound wherein R₁ is 4-methoxy-phenyl, Y is O, R₂ is 4-methoxy-phenyl, R₃ is 2-(N-methylamino)ethyl, and R_a is H; and a compound wherein R₁ is 4-methoxy-phenyl, Y is O, R₂ is 4-methoxy-phenyl, R₃ is 2-(N-methylamino)ethyl, and R_a is 2-(N-methylamino)ethyl;

and pharmaceutically acceptable salts thereof.

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of formula (I) carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid;

and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treatment of embodiments of the present invention, the term "administering" encompasses the treatment of the various disorders described with the compound specifically disclosed or with a compound which may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition comprising the (+)-enantiomer of a compound of formula (I) wherein said composition is substantially free from the (−)-isomer of said compound. In the present context, substantially free means less than 25%, preferably less than 10%, more preferably less than 5%, even more preferably less than 2% and even more preferably less than 1% of the (−)-isomer calculated as.

$$\% \ (+)\text{-enantiomer} = \frac{(\text{mass}(+)\text{-enantiomer})}{(\text{mass}(+)\text{-enantiomer}) + (\text{mass}(-)\text{-enantiomer})} \times 100$$

Another embodiment of the present invention is a composition comprising the (−)-enantiomer of a compound of formula (I) wherein said composition is substantially free from the (+)-isomer of said compound. In the present context, substantially free from means less than 25%, preferably less than 10%, more preferably less than 5%, even more preferably less than 2% and even more preferably less than 1% of the (+)-isomer calculated as $$\% \ (-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice. Thus, particular embodiments of the present invention are directed to pharmaceutical compositions comprising compounds of formula (I) and one or more than one pharmaceutically acceptable carrier, excipient or diluent.

By way of example, in the pharmaceutical and veterinary compositions of embodiments of the present invention, the compounds of formula (I) may be admixed with any suitable binder(s), lubricant(s), suspending agent(s), coating agent(s), and/or solubilizing agent(s).

Tablets or capsules of the compounds may be administered one or two or more at a time, as appropriate. It is also possible to administer the compounds in sustained release formulations.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin. They can also be incorporated, at a concentration of between 1% and 10% by weight, into an ointment consisting of a white wax or white soft paraffin base together with such stabilizers and preservatives as may be required. An alternative means of transdermal administration is by use of a skin patch.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly, subcutaneously, intradermally or intrathecally. In this case, the compositions will comprise a suitable carrier or diluent.

For parenteral administration, the compositions are best used in the form of a sterile aqueous solution which may contain other substances, for example, enough salts or monosaccharides to make the solution isotonic with blood.

For buccal or sublingual administration, the compositions may be administered in the form of tablets or lozenges, which can be formulated in a conventional manner.

By way of further example, pharmaceutical and veterinary compositions containing one or more of the compounds of formula (I) as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral, etc.). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations also may be coated with substances such as sugars or be enterically-coated so as to modulate the major site of absorption. For parenteral administration, the carrier will usually consist of sterile water, and other ingredients may be added to increase solubility or preservation. Injectable suspensions or solutions may also be prepared utilizing aqueous carriers along with appropriate additives.

A therapeutically effective amount of compounds of formula (I) or a pharmaceutical composition thereof comprises a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Advantageously, compounds of formula (I) may be administered in a single daily dose, or the total daily dosage may be administered in divided doses of two, three or four times daily. Furthermore, compounds of formula (I) can be administered in intranasal form via topical use of suitable intranasal vehicles, or via transdermal skin patches well known to those skilled in that art.

It is also apparent to one skilled in the art that the therapeutically effective dose for active compounds of formula (I) or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of the compounds of formula (I) as analgesics is required for a subject in need thereof.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the diseases or conditions such as those listed above, a therapeutically effective dose can be determined by persons skilled in the art by the use of established animal models. The therapeutically effective dose of the compounds of Formula (I) exemplified in such a treatment is from about 0.001 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
AcCl acetyl chloride
AcOH glacial acetic acid
aq. aqueous
Bn or Bzl benzyl
CDI N,N'-carbonyldiimidazole
conc. concentrated
DAMGO Tyr-D-Ala-Gly-(methyl)Phe-Gly-ol
DBU 1,8-diazabicyclo[5.4.0]undec-7-ene
DCE 1,2-dichloroethane
DCM dichloromethane
DIEA diisopropylethylamine
DMF N,N-dimethylformamide
DMSO dimethylsulfoxide
DPDPE [D-Pen2,D-PenS]-enkephalin
dppf 1,1'-bis(diphenylphosphino)ferrocene
EDC 1-ethyl-3-(3-dimethylaminopropyl) carbodiimide
ESI electron-spray ionization
EtOAc ethyl acetate
EtOH ethanol
h or hrs hour(s)
HATU O-(1H-7-azabenzotriazol-1-yl)-1,1,3,3-tetramethyl-uronium-hexafluorophosphate
HBTU O-(1H-benzotriazol-1-yl)-1,1,3,3-tetramethyluronium hexafluorophosphate
HEPES 2-[4-(2-hydroxyethyl)-1-piperazinyl]ethanesulfonic acid
HOBt N-hydroxybenzotriazole
HPLC high performance liquid chromatography
Me methyl
MeOH methanol
MHz megahertz
min minutes
MPLC medium pressure liquid chromatography
MS mass spectrometry
NMR nuclear magnetic resonance
NT not tested
Ph phenyl
Pd/C palladium on activated carbon
Ph$_3$P triphenylphosphine
PPA polyphosphoric acid
PyBOP benzotriazol-1-yl-oxytripyrrolidinophosphonium hexafluorophosphate
rt room temperature
TBDMS tert-butyldimethylsilyl
TEA/Et$_3$N triethylamine
TFA trifluoroacetic acid
THF tetrahydrofuran
TLC thin layer chromatography
TMS tetramethylsilane or trimethylsilyl Scheme A illustrates the preparation of compounds of Formula (I)-A and Formula (I)-A1 wherein Y is vinyl or ethyl, respectively, $R_1$ is di($C_{1-2}$alkyl)aminocarbonyl, and $R_3$ is as defined herein. $R_{3a}$ of compound A5 is defined as (N-methylamino)methyl, pyrrolidin-2-yl, azetidin-3-yl, or piperidin-3-yl. Ring A of compound A5-1 is defined as 3- or 4-aminocyclohexyl, piperidin-3-yl, piperidin-4-yl, Scheme A

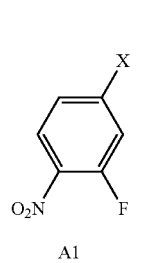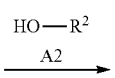

A1

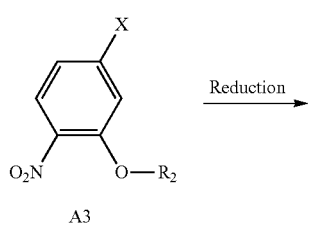

A3

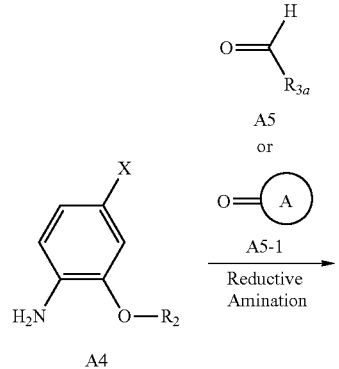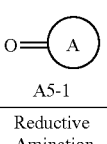

A4

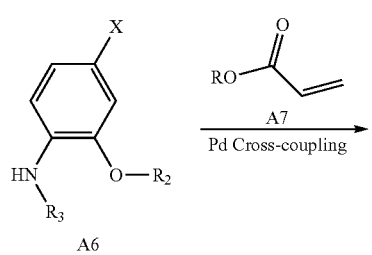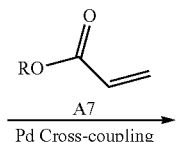

A6

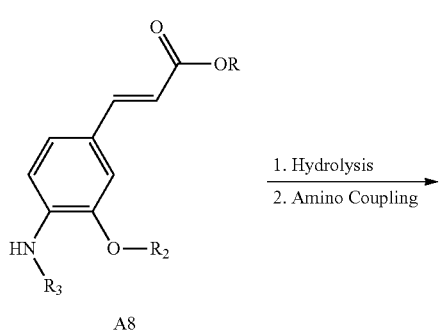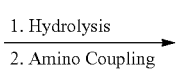

A8

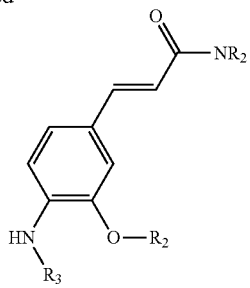

Formula (I)-A

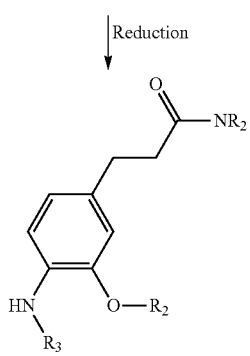

Formula (I)-A1

X = Cl or Br

Compound A1 is either commercially available or can be made by known methods described in the scientific literature. Reaction with an appropriately substituted alcohol of formula A2, optionally in the presence of a base, affords a compound of formula A3. The nitro group of a compound of formula A3 may be reduced to the corresponding amino group by the action of a reducing agent such as zinc metal in the presence of acetic acid in an organic solvent such as methanol, or by the action of sodium borohydride in the presence of nickel chloride or a catalytic hydrogenation. The resultant aniline of formula A4 may be alkylated with an $R_{3a}$-substituted aldehyde (A5) or a ketone of formula A5-1, in the presence of a reducing agent such as sodium triacetoxyborohydride in acetic acid to afford a compound of formula A6. A palladium catalyzed coupling with a compound of formula A7, wherein R is $C_{1-4}$alkyl, in the presence or absence of added ligands for palladium such as dppf or tri-o-tolylphosphine, affords an alkene of formula A8. The alkoxycarbonyl group of a compound of formula A8 may be saponified in the presence of hydroxide ion to form its corresponding carboxylic acid, which may then be coupled with a di($C_{1-4}$ alkyl)amine, in the presence of an appropriate coupling agent such as EDCI, and an activating agent such as HOBt, to form an amide of formula (I)-A. Reduction of the alkenyl group of a compound of formula (I)-A with a reducing agent such as catalytic hydrogenation affords a compound of formula (I)-A1. One skilled in the art will recognize that certain compounds of formula A5 and A5-1 may require an amino protecting group (P), which may be carried through subsequent chemical steps of the synthetic scheme. Conventional chemical methods may be used for amino deprotection at a later stage. For example, a Boc group may be removed by the action of a mineral acid or by an organic acid such as trifluoroacetic acid.

Scheme B illustrates the preparation of compounds of Formula (I)-B wherein Y is ethyl, and $R_{1a}$ is optionally substituted phenyl, naphthyl, optionally substituted pyridinyl, pyrimidin-5-yl, furanyl, or thienyl.

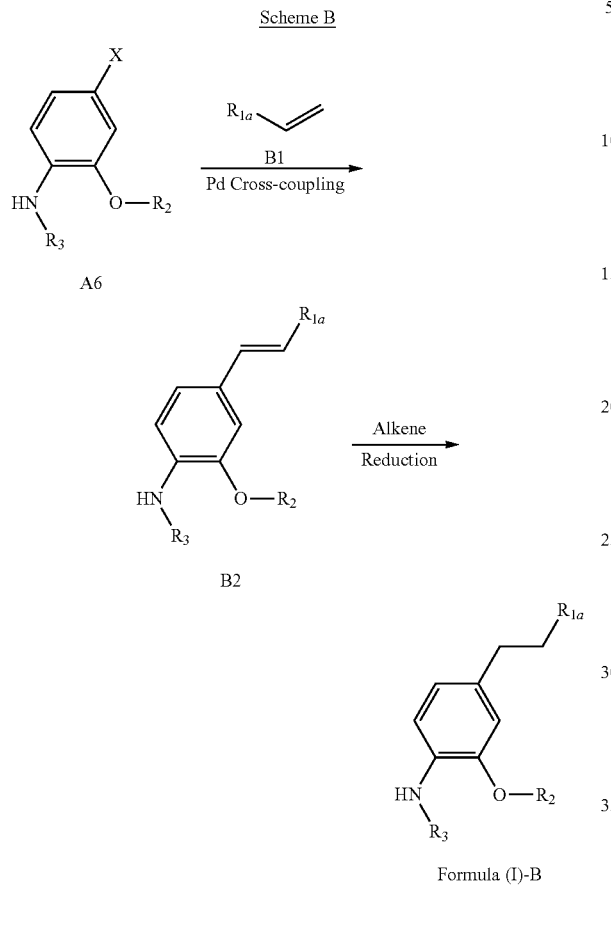

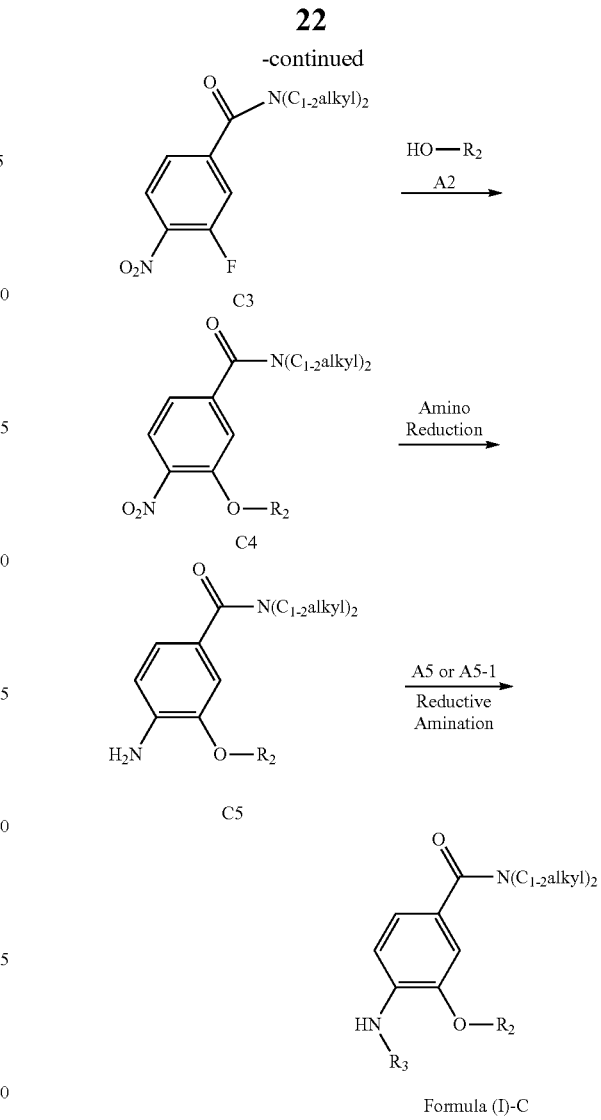

A compound of formula A6 may be coupled with a compound of formula B1 wherein $R_{1a}$ is defined herein, in the presence of a palladium catalyst and in the presence or absence of added ligands for palladium, and in the presence of an organic base such as TEA to afford an alkene of formula B2. Reduction of the alkenyl functionality may be achieved by a transition metal-catalyzed hydrogenation to afford, upon optional amino deprotection, a compound of formula (I)-B.

Scheme C illustrates the preparation of compounds of Formula (I)-C wherein Y is a bond and $R_1$ is di($C_{1-2}$alkyl)aminocarbonyl.

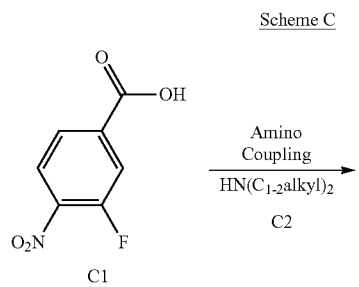

The compound C1 is either commercially available or can be made by known methods described in the scientific literature. The compound C1 may be coupled with an amine of formula C2 in the presence of an appropriate coupling agent such as EDCI, and an activating agent such as HOBt, to afford an amide of formula C3. Aromatic nucleophilic substitution with a compound of formula A2 in the presence of a base affords a compound of formula C4. The nitro group of a compound of formula C4 may be reduced to the corresponding amino group by the action of a reducing agent such as zinc metal in the presence of acetic acid in an organic solvent such as methanol, or by the action of sodium borohydride in the presence of nickel chloride, or a catalytic hydrogenation. The resultant aniline of formula C5 may be alkylated with an $R_{3a}$-substituted aldehyde (A5) or ketone of formula A5-1, in the presence of a reducing agent such as sodium triacetoxyborohydride in acetic acid to afford, upon optional amino deprotection, a compound of formula (I)-C.

Scheme D illustrates the preparation of compounds of Formula (I)-D wherein Y is a bond and $R_1$ is optionally substituted phenyl, naphthyl, optionally substituted pyridinyl, pyrimidin-5-yl, furanyl, or thienyl (represented as $R_{1a}$).

Scheme D

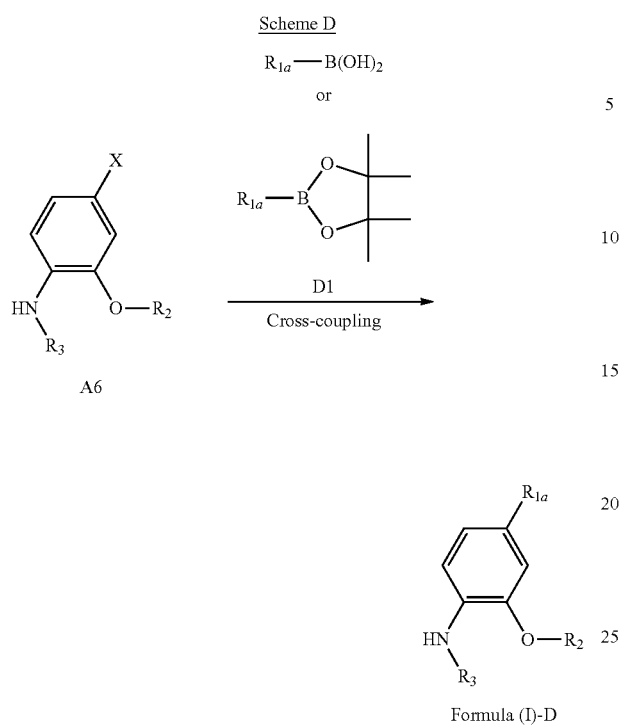

Formula (I)-D

The $R_{1a}$ group may be introduced into a compound of formula A6 through a palladium catalyzed cross-coupling reaction with an appropriately substituted boronic acid or boronate ester (D1), in the presence of a suitable base such as potassium carbonate. The reaction also may be carried out in the presence or absence of added ligands for palladium which, when used, include one or more than one of triphenylphosphine, tri-O-tolylphosphine, tri(tert-butyl)phosphine, 1,1'-bis(diphenylphosphino)ferrocene, bis[2-(diphenyl-phosphino)phenyl]ether, 2-dicyclohexylphosphino-2',6'-dimethoxybiphenyl, 1-butyl-3-methylimidazolium hexafluorophosphate, and the like. Useful solvents include ethanol, THF, DMF, toluene, DME, dioxane, or benzene. Upon optional amino deprotection, a compound of formula (I)-D may be prepared.

Scheme E illustrates the preparation of compounds of Formula (I)-E wherein Y is a bond, $R_1$ is optionally substituted phenyl, naphthyl, optionally substituted pyridinyl, pyrimidin-5-yl, furanyl, or thienyl (represented as $R_{1a}$); and $R_3$ is taken with —N—$R_a$ to form piperazin-1-yl.

Scheme E

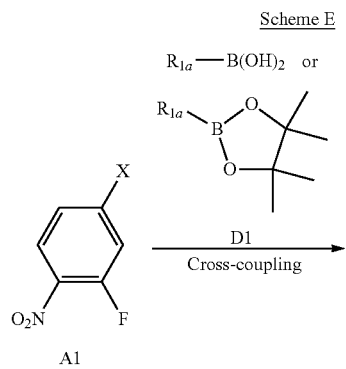

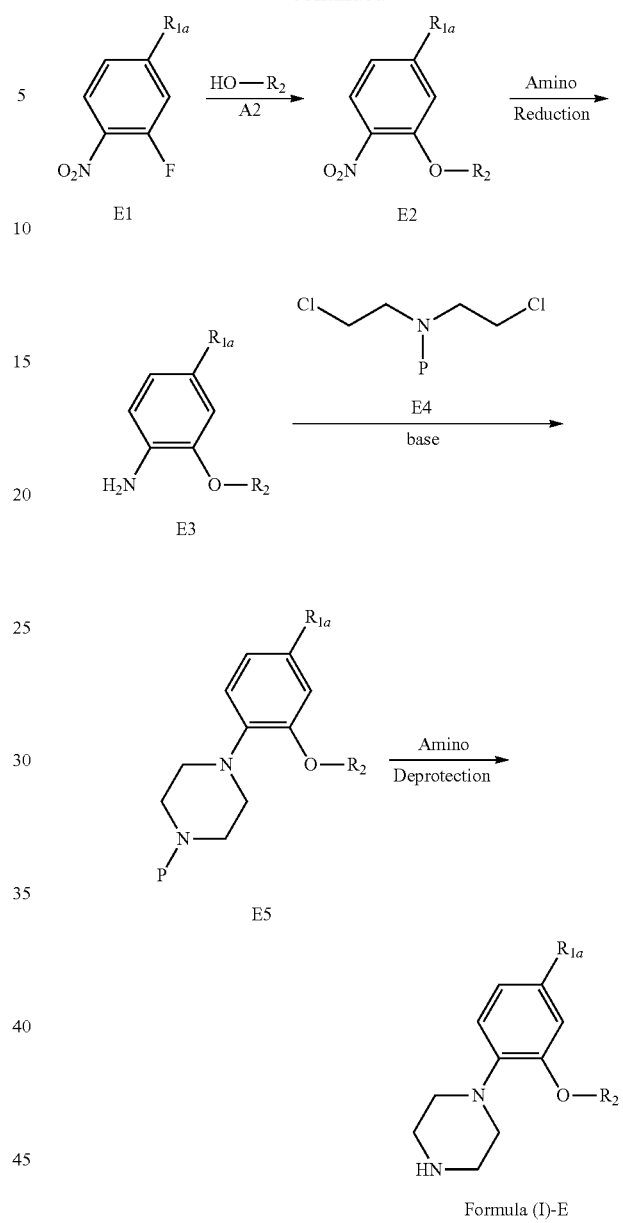

Formula (I)-E

The $R_{1a}$ group may be introduced into a compound of formula A1 through a palladium catalyzed cross-coupling reaction with an appropriately substituted boronic acid or boronate ester (D1), in the presence of a suitable base such as potassium carbonate, as further described herein. A compound of formula E1 may be reacted with a compound of formula A2 in the presence of a suitable base to form a compound of formula E2. The nitro group of a compound of formula E2 may be reduced to the corresponding aniline as previous described herein to form a compound of formula E3. Treatment with a protected amine of formula E4 in the presence of a suitable base such as potassium carbonate affords a compound of formula E5. Removal of amino protecting group (P) affords a compound of formula (I)-E.

Scheme F illustrates the preparation of compounds of Formula (I)-F wherein Y is O, $R_1$ is optionally substituted phenyl (pictured as $R_{1f}$), and $R_3$ is as defined by the invention.

Scheme F

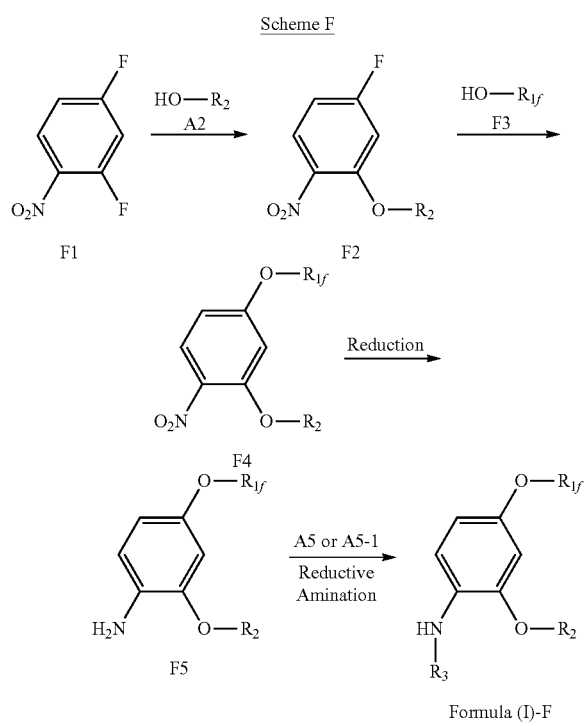

Formula (I)-F

A difluoro compound of formula F1 is either commercially available or readily synthesized according to methods described in the scientific literature. Upon nucleophilic aromatic substitution with a compound of formula A2, optionally in the presence of a base, a compound of formula F2 may be prepared. Subsequent reaction with an $R_{1f}$-substituted phenol of formula F3, optionally in the presence of a base, affords a compound of formula F4. Reduction of the nitro group as previously described affords a compound of formula F5. Treatment with an aldehyde of formula A5 or a ketone of formula A5-1 in the presence of a hydride source followed by conventional amino deprotection if $R_3$ contains an amino protecting group provides compounds of formula (I)-F.

Scheme G illustrates the preparation of certain useful $R_3$ intermediates of the present invention, useful for the synthesis of compounds of Formula (I) wherein $R_3$ is pyrrolidin-2-yl methyl substituted at the 3- or 4-position with one to two fluoro substituents.

Scheme G

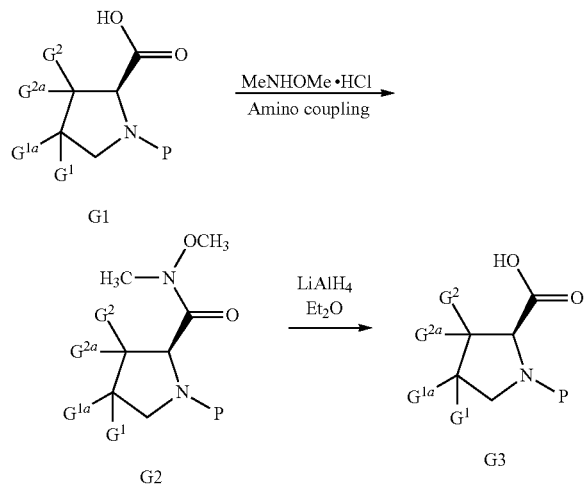

$G^1, G^{1a}, G^2, G^{2a}$=H or F
such that no more than two can be F

A compound of formula G1 is either commercially available or can be prepared according to known methods described in the scientific literature. A compound of formula G1 (wherein $G^1, G^{1a}, G^2$, and $G^{2a}$ are each hydrogen or fluoro, such that no more than two of said $G^1, G^{1a}, G^2$, and $G^{2a}$ can be fluoro) may be treated with N,O-dimethylhydroxylamine hydrochloride, in the presence of a peptide coupling agent such as HBTU and an organic base such as DIEA, in an organic solvent such as DMF, to afford a compound of formula G2. A compound of formula G2 may be converted to its corresponding aldehyde of formula G3 by the action of lithium aluminum hydride. A compound of formula G3 may be used in an analogous manner to a compound of formula A5 to form compounds of Formula (I).

Scheme H describes the preparation of compounds of Formula (I)-H wherein $R_1$ is optionally substituted phenyl, naphthyl, optionally substituted pyridinyl, pyrimidin-5-yl, furanyl, or thienyl (represented as $R_{1a}$); Y is a bond, and $R_3$ is taken with —N—$R_a$ to form piperazin-1-yl substituted with 4-$C_{1-4}$alkyl.

Scheme H

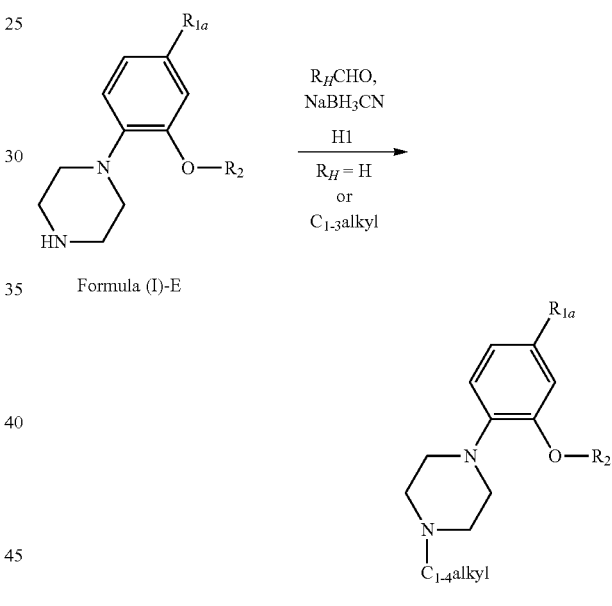

Formula (I)-H

A compound of Formula (I)-E may be reacted with a compound of formula H1 wherein $R_H$ is hydrogen or $C_{1-3}$alkyl, in the presence of a hydride source such as sodium cyanoborohydride, to form an alkylated product of formula (I)-H.

Scheme I illustrates the preparation of compounds of Formula (I)-I wherein Y is a bond, $R^1$ is 5-oxo-4,5-dihydro-[1,2,4]oxadiazol-3-yl, and $R^3$ is as defined herein.

Scheme I

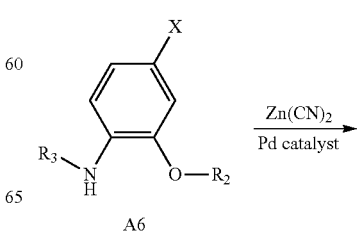

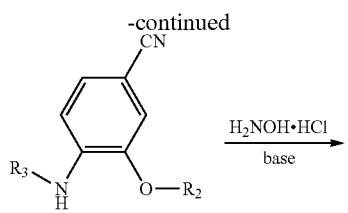

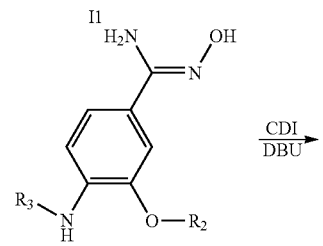

I2

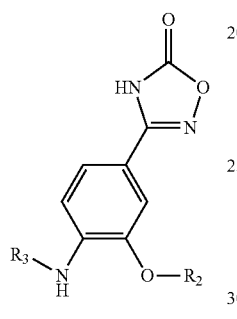

Formula (I)-I

A compound of formula A6 may be prepared by the synthetic methods described in the schemes provided herein. A compound of formula A6 may be treated with zinc cyanide in the presence of a palladium catalyst such as Pd(PPh$_3$)$_4$ to afford a cyanide of formula I1. Reaction of the cyano group with hydroxylamine hydrochloride in the presence of a base affords a compound of formula I3. Condensation of a compound of formula I2 with CDI in the presence of a base such as DBU gives a compound of formula (I)-I. Compounds of formula (I)-I wherein R$_3$ contains an amino protecting group may require conventional removal of the group.

Scheme J illustrates the preparation of compounds of formula (I)-J and (I)-J1 wherein R$_3$ is 2-(N-methylamino)ethyl or azetidin-3-ylmethyl, and R$_a$ is hydrogen or 2-(N-methylamino)ethyl, respectively. R$_{3J}$ is defined as N-protected methylaminomethyl or N-protected azetidin-3-yl.

Scheme J

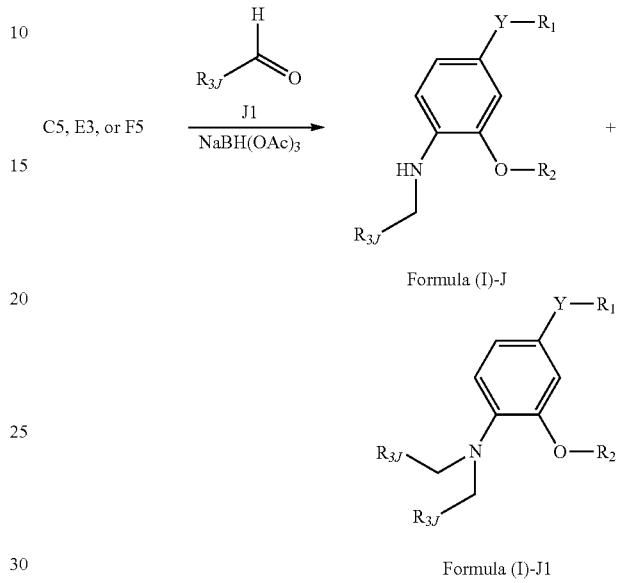

A compound of formula C5, E3, or F5 may undergo a reductive alkylation with an aldehyde of formula J1 in the presence of a hydride source such as sodium triacetoxyborohydride, followed by conventional amino deprotection, to afford a mixture of compounds of formula (I)-J and formula (I)-J1. Products of formula (I)-J and formula (I)-J1 may be separated using conventional separation methods known to those skilled in the art.

Scheme K illustrates the preparation of compounds of formula (I)-K, formula (I)-K1, and formula (I)-K2, wherein R$_1$, Y, and R$_3$ are as defined herein and R$_a$ is optionally substituted C$_{1-2}$alkyl as defined herein.

Scheme K

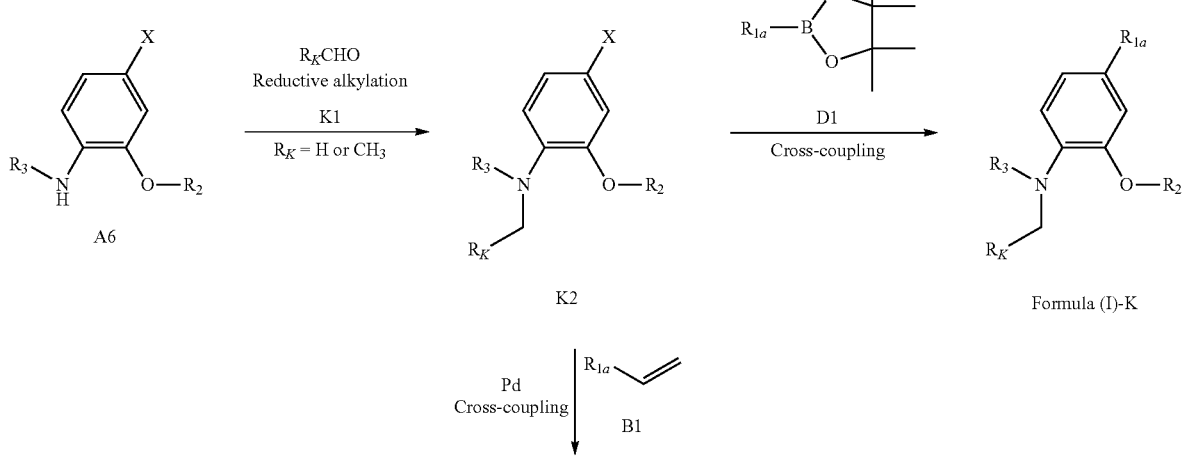

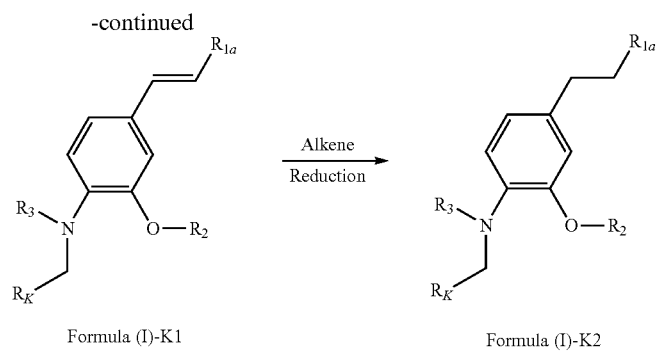

Formula (I)-K1 → Formula (I)-K2 (Alkene Reduction)

A compound of formula A6 may undergo a reductive alkylation with an aldehyde of formula K1 in the presence of a hydride source such as sodium cyanoborohydride or sodium triacetoxyborohydride to afford a compound of formula K2. A compound of formula K2 may be coupled with a compound of formula D1 which, upon removal of any chemically necessary protecting groups, may afford, upon optional amino deprotection, a compound of formula (I)-K wherein Y is a bond. Similarly, a compound of formula K1 may be coupled with a compound of formula B1 to afford a compound of formula (I)-K1 wherein Y is vinyl. Conventional reduction of the vinyl group as described in Scheme B affords, upon optional amino deprotection, a compound of formula (I)-K2 wherein Y is ethyl.

Scheme L illustrates the preparation of compounds of formula (I)-L, wherein $R_{1L}$ is di($C_{1-2}$alkyl)aminocarbonyl or —$OR_{1f}$, $R_3$ is defined herein, and $R_a$ is optionally substituted $C_{1-2}$alkyl as defined herein.

Scheme L

Formula (I)-C or Formula (I)-F → Formula (I)-L $R_K$CHO, K1
Reductive alkylation
$R_K$ = H or $CH_3$ $R_{1L}$ = di($C_{1-2}$alkyl)aminocarbonyl or —$OR_{1f}$ A compound of formula (I)-C or formula (I)-F may undergo a reductive alkylation with an aldehyde of formula K1 in the presence of a hydride source such as sodium cyanoborohydride or sodium triacetoxyborohydride to afford, upon optional amino deprotection, a compound of formula (I)-L.

Scheme M illustrates the preparation of compounds of Formula (I)-M wherein Y and $R_1$ are as defined herein, and $R_3$ is taken with —N—$R_a$ to form piperazin-1-yl.

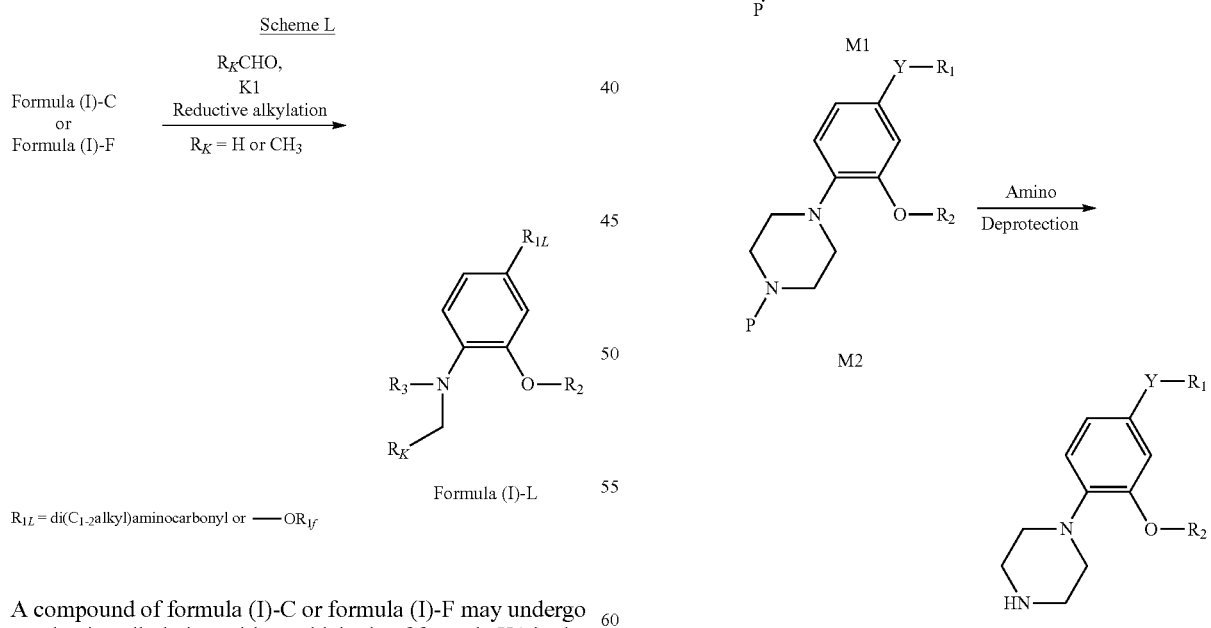

Scheme M

A compound of formula A4 may be treated with a protected amine of formula E4 in the presence of a suitable base such as potassium carbonate to afford a compound of formula M1. Suitable Y and $R_1$ groups of the present invention may be installed by reaction with a compound of formula A7, B1, or F3, for example, as taught in the schemes provided herein, to afford a compound of formula M2. Amino deprotection using conventional chemistry affords a compound of formula (I)-M.

SPECIFIC EXAMPLES

Reagents were purchased from commercial sources. Nuclear magnetic resonance (NMR) spectra for hydrogen atoms were measured in the indicated solvent with tetramethylsilane (TMS) as the internal standard on a Bruker Avance or Varian (300 or 400 MHz) spectrometer. The values are expressed in parts per million downfield from TMS. The mass spectra (MS) were determined on a Micromass Platform LC or Agilent 1100 LCMS spectrometer as (ESI) m/z (M+H$^+$) using an electrospray technique. Microwave accelerated reactions were performed using a CEM Discover or Biotage microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

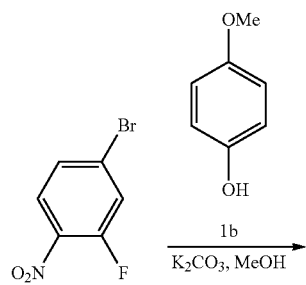
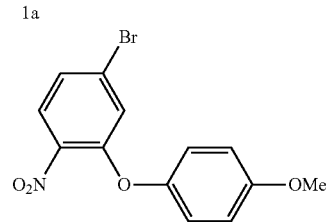
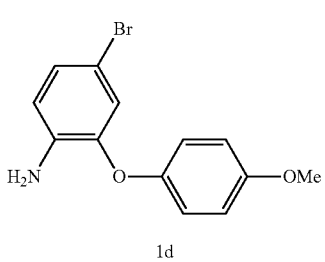
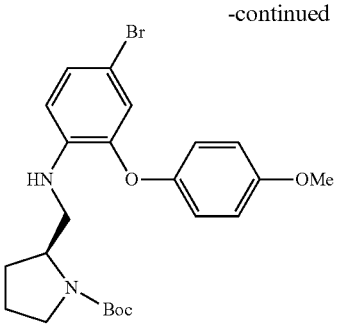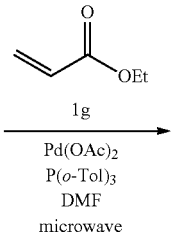
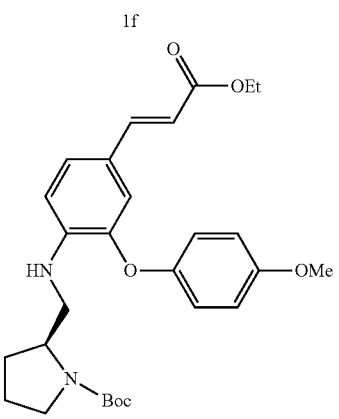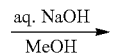
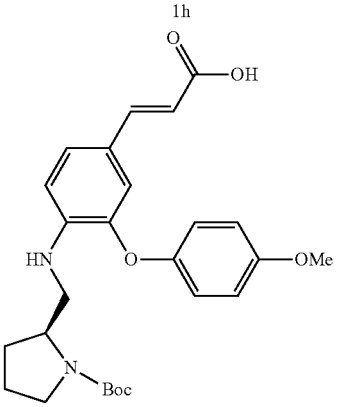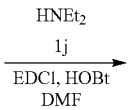
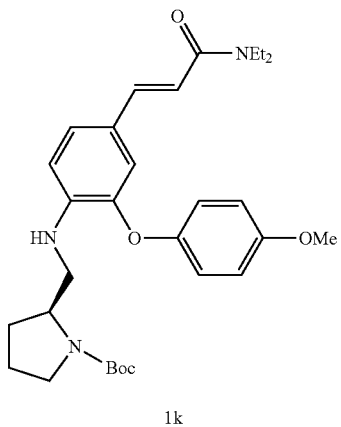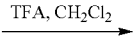

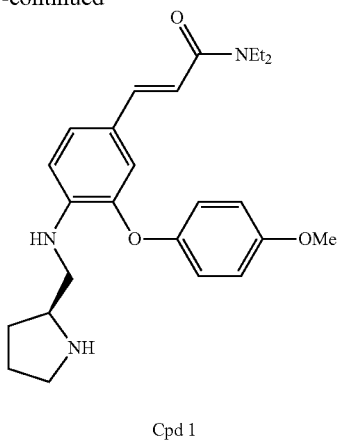

Cpd 1

A. 4-Bromo-2-(4-methoxy-phenoxy)nitrobenzene (1c). A mixture of Compound 1a (2.20 g, 10.0 mmol), 4-methoxyphenol (Compound 1b, 1.32 g, 10.5 mmol), $K_2CO_3$ (1.52 g, 11.0 mmol), and 6 mL of DMF was stirred at 75° C. for 3 h. The mixture was concentrated in vacuo and the residue was partitioned between EtOAc and water. The organic layer was washed successively with 2N aqueous NaOH, 2N aqueous HCl, saturated aqueous $NaHCO_3$, and brine, dried over $Na_2SO_4$, and concentrated to give Compound 1c as a brown gel (2.95 g, 91%). $^1$H NMR (300 MHz, $CDCl_3$): δ 7.11-7.84 (d, 1H), 7.24-7.27 (m, 1H), 7.01-7.06 (m, 3H), 6.93-6.97 (m, 2H), 3.71 (s, 3H).

B. 4-Bromo-2-(4-methoxy-phenoxy)-aniline (1d). A mixture of Compound 1c (1.64 g, 5.06 mmol), zinc (1.98 g, 30.4 mmol), 15 mL of HOAc, and 50 mL of MeOH was stirred at 20° C. for 20 h. After removal of solvents, the residue was partitioned between EtOAc and 3N aqueous NaOH. The organic phase was washed with brine, dried over $Na_2SO_4$, and concentrated to give Compound 1d as a brown oil (1.54 g, 103% yield). MS: m/z 294.0 (M+H)$^+$.

C. 2-(S)-{[4-Bromo-2-(4-methoxy-phenoxy)-phenylamino]-methyl}-pyrrolidine-1-carboxylic acid tert-butyl ester (1f). $NaBH_3CN$ (0.67 mmol, 10.1 mmol) was added to a mixture of Compound 1d (1.45 g, 5.06 mmol) and Boc-L-prolinal (Compound 1e, 1.04 g, 5.06 mmol) in 20 mL of MeOH and 2.5 mL of HOAc. The mixture was stirred at 20° C. for 1.5 h. After evaporation of solvent, the residue was extracted with EtOAc. The organic layer was washed successively with 1N aqueous NaOH, 1N aqueous HCl, and brine and was dried over $Na_2SO_4$. Concentration and purification by flash column chromatography ($SiO_2$), eluting with a hexanes-ether gradient, afforded Compound 1f as a yellow oil (2.36 g, 98% yield) MS: m/z 476.9, 478.8 (M+H)$^+$.

D. (E)-2-(S)-{[4-(2-Ethoxycarbonyl-ethenyl)-2-(4-methoxy-phenoxy)-phenylamino]methyl}-pyrrolidine-1-carboxylic acid tert-butyl ester (1h). A mixture of Compound 1f (0.19 g, 0.4 mmol), ethyl acrylate (1 g, 0.43 g, 0.045 mL, 0.5 mmol), $Pd(OAc)_2$ (0.0009 g, 0.004 mmol), tri-o-tolylphosphine (0.0049 g, 0.016 mmol), and 0.4 mL of DMF was irradiated in a microwave reactor for 10 min at 160° C. Purification by preparative TLC, eluting with 3:7 EtOAc:hexanes, gave Compound 1h as a yellow solid (0.15 g, 78% yield). MS: m/z 483.2 (M+H)$^+$.

E. (E)-2-(S)-{[4-(2-Carboxy-ethenyl)-2-(4-methoxy-phenoxy)-phenylamino]-methyl}-pyrrolidine-1-carboxylic acid tert-butyl ester (1i). A mixture of Compound 1h (0.15 g, 0.31 mmol), 1 mL of 3N aqueous NaOH (3 mmol), and 1 mL of MeOH was stirred at 20° C. for 20 h. After evaporation of the MeOH, the aqueous phase was acidified with 1N aqueous HCl and extracted with EtOAc. The organic layer was washed with brine, dried over $Na_2SO_4$, and concentrated to give Compound 11 (0.18 g, 124% yield). MS: m/z 469.3 (M+H)$^+$.

F. 2-(S)-{[4-(2-Diethylcarbamoyl-ethenyl)-2-(4-methoxy-phenoxy)-phenylamino]-methyl}-pyrrolidine-1-carboxylic acid tert-butyl ester (1k). A mixture of Compound 1i (0.18 g, 0.38 mmol), N,N-diethylamine (Compound 1j, 0.04 mL, 0.38 mmol), N-(3-dimethylaminopropyl)-N'-ethylcarbodiimide monohydrochloride (EDC-HCl, 0.095 g, 0.49 mmol), and HOBt (0.10 g, 0.76 mmol) was stirred in 3 mL of DMF at 20° C. for 20 h. Water was added and the mixture was extracted with EtOAc. The organic phase was washed successively with 1N aqueous HCl, brine, saturated aqueous $NaHCO_3$, and brine and was dried over $MgSO_4$. Evaporation of the solvent and purification by preparative TLC, eluting with 1:1 ether:hexanes, gave Compound 1k (0.100 g, 50% yield). MS: m/z 524.2 (M+H)$^+$.

G. Cpd 1: (2E)-N,N-Diethyl-3-[3-(4-methoxyphenoxy)-4-{[(2S)-pyrrolidin-2-ylmethyl]amino}phenyl]prop-2-enamide. A mixture of Compound 1k (0.026 g, 0.050 mmol), TFA, and $CH_2Cl_2$ was stirred at 20° C. for 4 h. After concentration, the residue was purified by reverse phase HPLC to afford Cpd 1 as a TFA salt (0.0063 g, 19% yield). MS: m/z 424.2 (M+H)$^+$.

Example 2

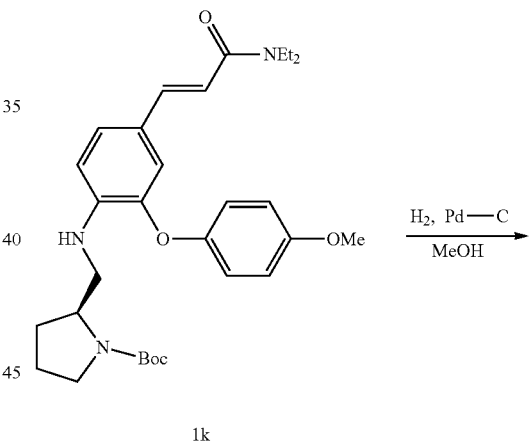

1k

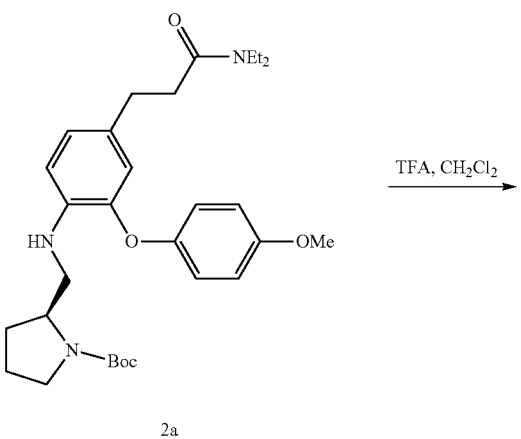

2a

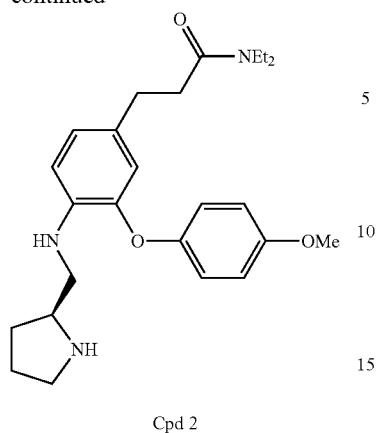

Cpd 2

A. 2-(S)-{[4-(2-Diethylcarbamoyl-ethyl)-2-(4-methoxy-phenoxy)-phenylamino]-methyl}-pyrrolidine-1-carboxylic acid tert-butyl ester (2a). A mixture of compound 1k (0.050 g, 1.0 mmol) and 10% palladium on carbon in MeOH was shaken under a hydrogen atmosphere (34 psi) at 20° C. for 4 h. The catalyst was filtered and solvent was removed by evaporation to give Compound 2a. MS: m/z 526.3 (M+H)$^+$.

B. Cpd 2: N,N-Diethyl-3-[3-(4-methoxyphenoxy)-4-{[(2S)-pyrrolidin-2-ylmethyl]amino}phenyl]propanamide. A mixture of Compound 2a (0.050 g, 0.095 mmol), TFA, and $CH_2Cl_2$ was stirred at 20° C. for 4 h. After concentration, the residue was purified by reverse phase HPLC to afford Cpd 2 as a TFA salt (0.022 g, 36% yield). $^1$H NMR (300 MHz, $CD_3OD$): δ 6.87-6.91 (m, 5H), 6.78 (d, 1H), 6.60 (d, 1H), 3.90 (m, 1H), 3.79 (s, 3H), 3.42-3.48 (m, 2H) 3.24-3.34 (m, 6H), 2.77 (t, 2H), 2.53 (t, 2H), 2.18-2.28 (m, 1H), 2.00-2.14 (m, 2H), 1.73-1.86 (m, 1H), 1.03-1.08 (m, 6H); MS: m/z 426.3 (M+H)$^+$.

Example 3

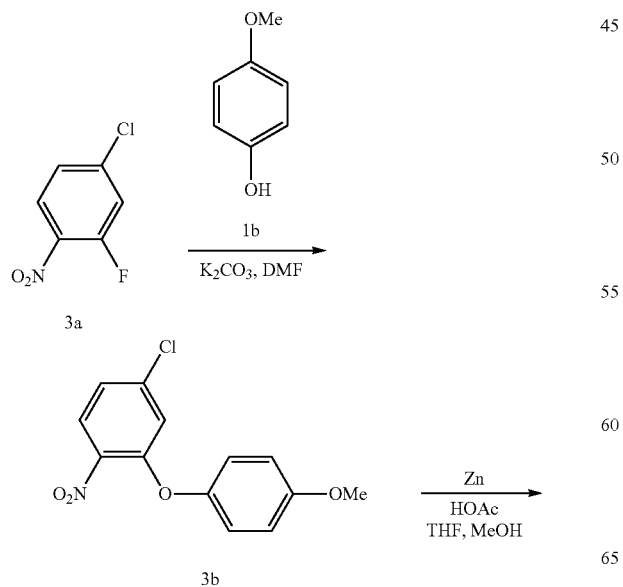

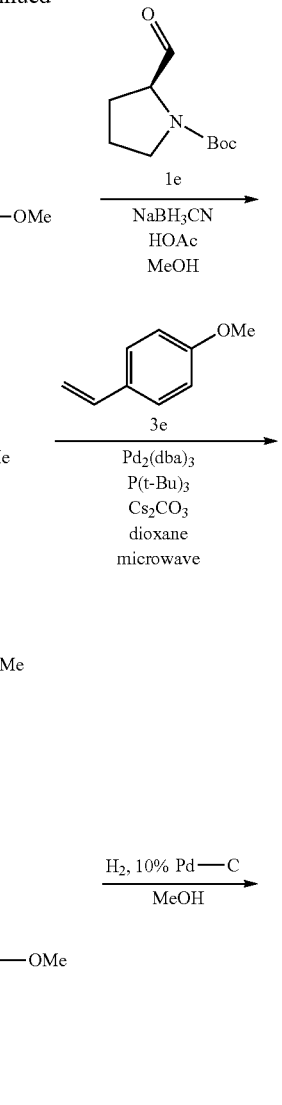

-continued

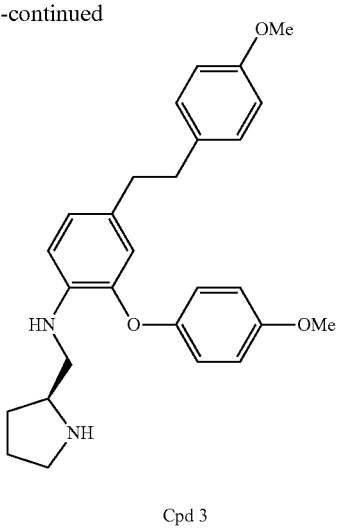

Cpd 3

A. 4-Chloro-2-(4-methoxy-phenoxy)nitrobenzene (3b). 4-Chloro-2-fluoronitrobenzene (Compound 3a, 1.76 g, 10 mmol), Compound 1b (1.30 g, 10.5 mmol), and $K_2CO_3$ (1.52 g, 11 mmol) were heated in 6 mL of DMF at 75° C. for 3 h. The mixture was concentrated in vacuo and the residue was partitioned between EtOAc and water. The organic layer was washed successively with 1N aqueous NaOH, 1N aqueous HCl, saturated aqueous $NaHCO_3$, and brine and dried over $Na_2SO_4$. Concentration and purification by flash column chromatography ($SiO_2$), eluting with a hexanes-EtOAc gradient, afforded Compound 3b as a yellow solid (2.75 g, 98% yield) MS: m/z 279.9 $(M+H)^+$.

B. 4-Chloro-2-(4-methoxy-phenoxy)-aniline (3c). A mixture of Compound 3b (2.47 g, 8.83 mmol), zinc (3.46 g, 53 mmol), 60 mL of HOAc, 5 mL of THF, and 36 mL of MeOH was stirred at 20° C. for 20 h. The solid material was filtered and washed with MeOH. The filtrate was partitioned between EtOAc and 1N aqueous NaOH. The organic phase was washed with brine, dried over $Na_2SO_4$, and concentrated to give Compound 3c as a black gel that was used without purification (1.80 g, 82% yield). MS: m/z 249.9 (M+H)'.

C. 2-(S)-{[4-Chloro-2-(4-methoxy-phenoxy)-phenylamino]-methyl}-pyrrolidine-1-carboxylic acid tert-butyl ester (3d). $NaBH_3CN$ (0.95 g, 14.4 mmol) was added to a mixture of Compound 3c (1.80 g, 7.2 mmol) and Compound 1e (1.48 g, 7.2 mmol) in 28 mL of MeOH and 3.5 mL of HOAc. The mixture was stirred at 20° C. for 1 h. After evaporation of solvent, the residue was extracted with EtOAc. The organic layer was washed successively with saturated aqueous $NaHCO_3$ and brine and was dried over $Na_2SO_4$. Concentration and purification by flash column chromatography ($SiO_2$), eluting with 3:7 EtOAc:hexanes, afforded Compound 3d as a brown oil (2.84 g, 91% yield). MS: m/z 433.1 $(M+H)^+$.

D. (E)-2-(S)-({2-(4-Methoxy-phenoxy)-4-[2-(4-methoxy-phenyl)-ethenyl]-phenylamino}-methyl)-pyrrolidine-1-carboxylic acid tert-butyl ester (3f). A mixture of Compound 3d (0.11 g, 0.254 mmol), 4-vinylanisole (Compound 3e, 0.042 g, 0.042 mL, 0.305 mmol), $Pd_2(dba)_3$ (0.035 g, 0.038 mmol), $P(t^-Bu)_3$ (0.032 g, 0.04 mL, 0.152 mmol), $Cs_2CO_3$ (0.091 g, 0.279 mmol), and 0.2 mL of dioxane was irradiated in a microwave reactor at 180° C. for 30 min. Brine was added and the mixture was extracted with EtOAc. The organic layer was dried over $Na_2SO_4$ and concentrated, and the residue was purified by preparative TLC to give Compound 3f (0.05 g, 51% yield). MS: m/z 531.4 $(M+H)^+$.

E. (E)-2-(S)-({2-(4-Methoxy-phenoxy)-4-[2-(4-methoxy-phenyl)-ethyl]-phenylamino}-methyl)-pyrrolidine-1-carboxylic acid tert-butyl ester (3 g). A mixture of compound 3f (0.050 g, 0.094 mmol) and 10% palladium on carbon in MeOH was shaken under a hydrogen atmosphere (38 psi) at 20° C. The catalyst was filtered and solvent was removed by evaporation to give Compound 3 g (0.05 g, 100% yield).

F. Cpd 3: (S)-{2-(4-Methoxy-phenoxy)-4-[2-(4-methoxy-phenyl)-ethyl]-phenyl}-pyrrolidin-2-ylmethyl-amine. A mixture of Compound 3 g (0.050 g, 0.094 mmol), TFA, and $CH_2Cl_2$ was stirred at 20° C. for 2 h. After concentration, the residue was dissolved in $CH_3CN$ and purified by reverse phase HPLC to afford Cpd 3 as a TFA salt (0.018 g, 29% yield). $^1H$ NMR (300 MHz, $CD_3OD$): δ 6.72-6.94 (m, 10H), 6.38 (m, 1H), 3.81-3.92 (m, 1H), 3.76 (s, 3H), 3.74 (s, 3H), 3.21-3.44 (m, 4H), 2.69-2.71 (m, 4H), 1.98-2.28 (m, 3H), 1.71-1.82 (m, 1H); MS: m/z 432.9 $(M+H)^+$.

Following the procedure described above for Example 3 and substituting the appropriate reagents, starting materials, and purification methods known to those skilled in the art, the following compounds of the present invention were prepared:

| Cpd | MS (M + H)+ | $^1H$ NMR |
|---|---|---|
| 4 | 433.2 | $^1H$ NMR (300 MHz, $CD_3OD$): δ 7.05-7.11 (m, 1H), 6.49-6.90 (m, 9H), 6.42 (m, 1H), 3.80-3.92 (m, 1H), 3.75 (s, 3H), 3.70 (s, 3H), 3.21-3.52 (m, 4H), 2.73-2.79 (m, 4H), 1.91-2.28 (m, 3H), 1.72-1.80 (m, 1H) |
| 5 | 402.9 | $^1H$ NMR (300 MHz, $CD_3OD$): δ 7.05-7.18 (m, 5H), 6.52-6.86 (m, 6H), 6.44 (m, 1H), 3.80-3.90 (m, 1H), 3.78 (s, 3H), 3.26-3.45 (m, 4H), 2.73-2.77 (m, 4H), 1.92-2.26 (m, 3H), 1.72-1.80 (m, 1H) |
| 6 | 421.2 | $^1H$ NMR (300 MHz, $CD_3OD$): δ 6.72-7.08 (m, 10H), 6.38 (m, 1H), 3.81-3.91 (m, 1H), 3.79 (s, 3H), 3.24-3.46 (m, 4H), 2.77-2.79 (m, 4H), 1.96-2.28 (m, 3H), 1.73-1.81 (m, 1H) |
| 7 | 421.2 | $^1H$ NMR (300 MHz, $CD_3OD$): δ 7.14-7.22 (m, 1H), 6.72-6.89 (m, 9H), 6.42 (m, 1H), 3.80-3.92 (m, 1H), 3.78 (s, 3H), 3.25-3.46 (m, 4H), 2.75-2.82 (m, 4H), 1.94-2.25 (m, 3H), 1.72-1.79 (m, 1H) |

Example 4

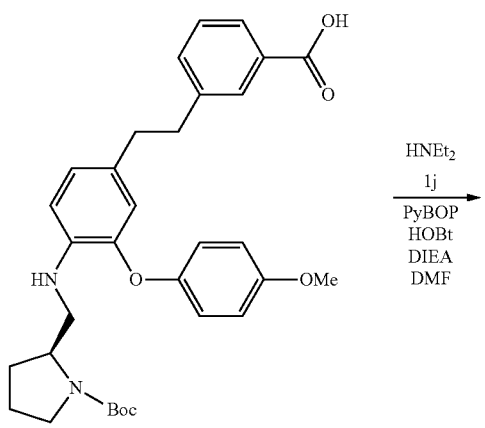

4a 3.13-3.31 (m, 4H), 2.76-2.86 (m, 4H), 2.00-2.28 (m, 3H), 1.75-1.82 (m, 1H), 1.21-1.26 (m, 3H), 0.98-1.04 (m, 3H); MS: m/z 502.4 (M+H)+.

Example 5

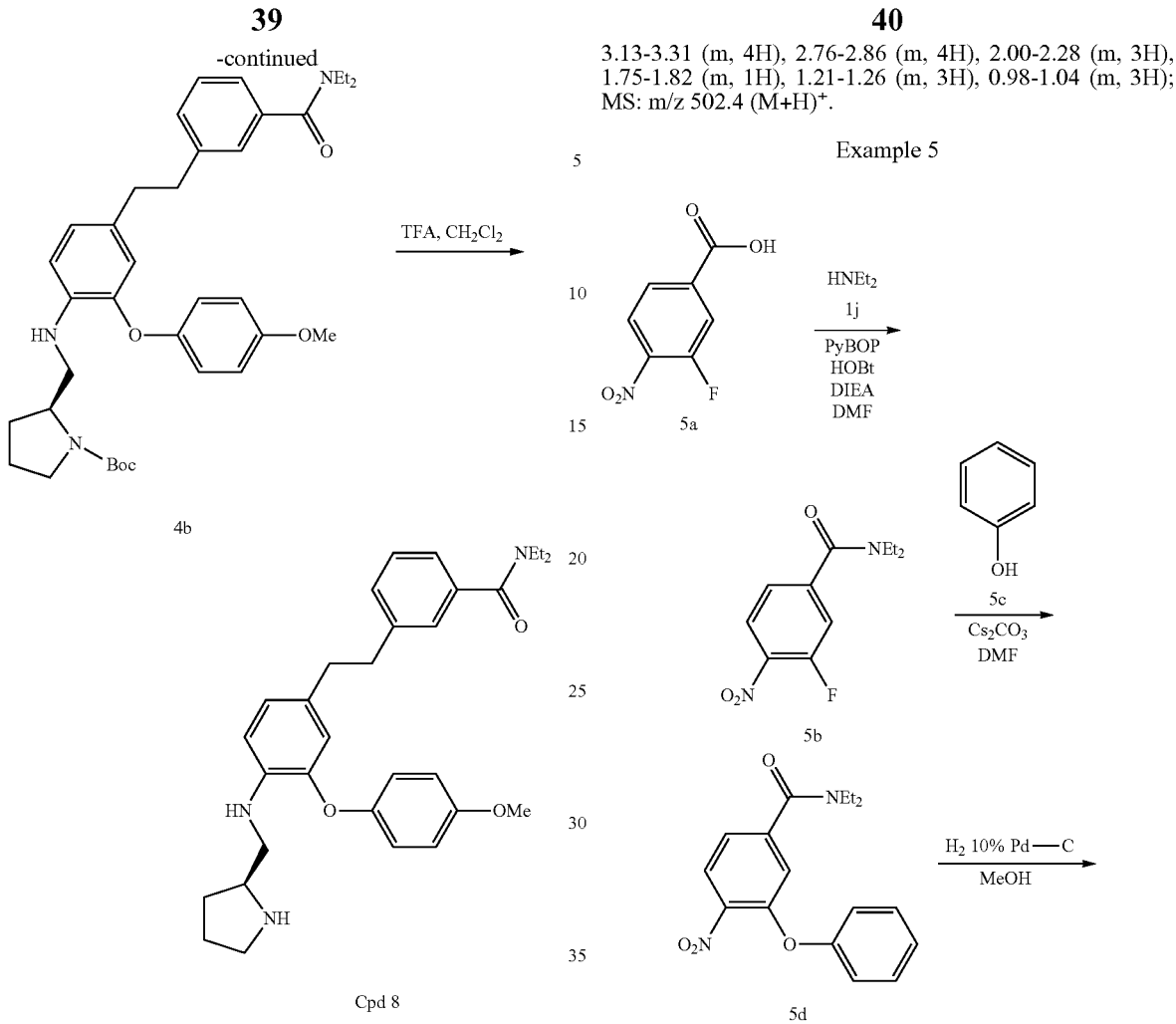

A. 2-(S)-{[4-[2-(3-Carboxy-phenyl)-ethyl]-2-(4-methoxy-phenoxy)-phenylamino]-methyl}-pyrrolidine-1-carboxylic acid tert-butyl ester (4a). Compound 4a was prepared according to the method used to prepare Compound 3 g described in Example 3 above, substituting 3-ethenylbenzoic acid for Compound 3e. MS: m/z 547.2 (M+H)+.

B. 2-(S)-{[4-[2-(3-Diethylcarbamoyl-phenyl)-ethyl]-2-(4-methoxy-phenoxy)-phenylamino]-methyl}-pyrrolidine-1-carboxylic acid tert-butyl ester (4b). A mixture of Compound 4b (0.016 g, 0.029 mmol), Compound 1j (0.0021 g, 0.003 mL, 0.029 mmol), PyBOP (0.030 g, 0.058 mmol), HOBt (0.0059 g, 0.044 mmol), DIEA (0.0075 g, 0.010 mL, 0.058 mmol), and 1 mL of DMF was stirred at 20° C. for 3 h. Water was added and the mixture was extracted with EtOAc. The organic layer was washed successively with 1N aqueous HCl, saturated aqueous NaHCO3, and brine and was dried over Na2SO4. Evaporation of solvent and purification by preparative TLC, eluting with 3:7 EtOAc:hexanes, afforded Compound 4b. MS: m/z 602.3 (M+H)+.

C. Cpd 8: (S)—N,N-Diethyl-3-(2-{3-(4-methoxy-phenoxy)-4-[(pyrrolidin-2-ylmethyl)-amino]-phenyl}-ethyl)-benzamide. A mixture of Compound 4b, TFA, and CH2Cl2 was stirred at 20° C. for 1.5 h. After concentration, the residue was dissolved in CH3CN and purified by reverse phase HPLC to afford Cpd 8 as a TFA salt (0.002 g, 9% yield, steps B and C). 1H NMR (300 MHz, CD3OD): δ 7.25-7.33 (m, 2H), 7.12-7.17 (m, 2H), 7.03 (m, 1H), 6.74-6.86 (m, 5H), 6.43 (m, 1H), 3.82-3.90 (m, 1H), 3.77 (s, 3H), 3.38-3.57 (m, 4H),

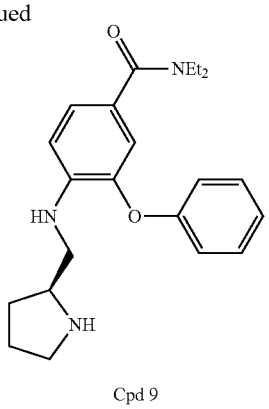

Cpd 9

A. N,N-Diethyl-4-nitro-3-fluoro-benzamide (5b). A mixture of Compound 5a (0.50 g, 2.7 mmol), Compound 1j (0.20 g, 0.28 mL, 2.7 mmol), PyBOP (2.81 g, 5.4 mmol), HOBt (0.55 g, 4.05 mmol), DIEA (0.70 g, 0.94 mL, 5.4 mmol), and 8 mL of DMF was stirred at 20° C. for 3 h. Water was added and the mixture was extracted with EtOAc. The organic layer was washed successively with 1N aqueous HCl, saturated aqueous NaHCO$_3$, and brine and was dried over Na$_2$SO$_4$. Evaporation of solvent and purification by preparative TLC, eluting with 4:6 EtOAc:hexanes, afforded Compound 5b (0.67 g, 103% yield). MS: m/z 240.9 (M+H)$^+$.

B. N,N-Diethyl-4-nitro-3-phenoxy-benzamide (5d). Compound 5b (0.22 g, 0.92 mmol), phenol (Compound 5c, 0.10 g, 1.1 mmol), Cs$_2$CO$_3$ (0.90 g, 2.7 mmol), and 4 mL of DMF were heated with stirring at 120° C. for 3 h. Water was added and the resulting mixture was extracted with EtOAc. The organic layer was washed successively with 3N aqueous NaOH, 2N aqueous HCl, and brine, dried over Na$_2$SO$_4$, and concentrated. The residue was purified by preparative TLC to provide Compound 5d as a brown oil. MS: m/z 315.0 (M+H)$^+$.

C. 4-Amino-N,N-diethyl-3-phenoxy-benzamide (5e). A mixture of compound 5d, prepared in Step B, and 10% palladium on carbon in MeOH was shaken under a hydrogen atmosphere (30 psi) at 20° C. for 3 h. The catalyst was collected by filtration and the solvent was removed by evaporation to give Compound 5e (0.19 g, 73% yield, steps B and C).

D. 2-[(4-Diethylcarbamoyl-2-phenoxy-phenylamino)-methyl]-pyrrolidine-1-carboxylic acid tert-butyl ester (5f). NaBH$_3$CN (0.025 mmol, 0.4 mmol) was added to a mixture of Compound 5e (0.063 g, 0.2 mmol) and Compound 1e (0.04 g, 0.2 mmol) in 5 mL of MeOH and 0.4 mL of HOAc. The mixture was stirred at 20° C. for 1.5 h. After evaporation of solvent, the residue was extracted with EtOAc. The organic layer was washed successively with saturated aqueous NaHCO$_3$ and brine and was dried over MgSO$_4$. Concentration and purification by preparative TLC afforded Compound 5f (0.07 g, 75% yield) MS: m/z 468.3 (M+H)$^+$.

E. Cpd 9: (S)—N,N-Diethyl-3-phenoxy-4-[(pyrrolidin-2-ylmethyl)-amino]-benzamide. A mixture of Compound 5f (0.07 g, 0.15 mmol), TFA, and CH$_2$Cl$_2$ was stirred at 20° C. for 1.5 h. After concentration, the residue was dissolved in CH$_3$CN and purified by reverse phase HPLC to afford Cpd 9 as a TFA salt (0.044 g, 49% yield). $^1$H NMR (300 MHz, CD$_3$OD): δ 7.33-7.39 (m, 2H), 7.10-7.15 (m, 2H), 7.00-7.03 (m, 2H), 6.89-6.92 (m, 1H), 6.77 (m, 1H), 3.88-3.93 (m, 1H), 3.26-3.55 (m, 8H), 1.99-2.25 (m, 3H), 1.74-1.81 (m, 1H), 1.03-1.17 (m, 6H); MS: m/z 368.0 (M+H)$^+$.

Following the procedure described above for Example 5 and substituting the appropriate reagents, starting materials, and purification methods known to those skilled in the art, the following compounds of the present invention were prepared:

| Cpd | MS (M + H)$^+$ | $^1$H NMR |
|---|---|---|
| 10 | 398.0 | $^1$H NMR (300 MHz, CD$_3$OD): δ 6.66-7.05 (m, 6H), 6.66 (m, 1H), 3.89-3.92 (m, 1H), 3.76 (s, 3H), 3.28-3.56 (m, 8H), 1.99-2.26 (m, 3H), 1.02-1.17 (m, 6H) |
| 11 | 398.0 | $^1$H NMR (300 MHz, CD$_3$OD): δ 7.11-7.21 (m, 2H), 6.97-7.06 (m, 3H), 6.84-6.86 (m, 1H), 6.48 (m, 1H), 3.88-4.00 (m, 1H), 3.77 (s, 3H), 3.54-3.58 (m, 2H), 3.28-3.38 (m, 6H), 2.00-2.27 (m, 3H), 1.81-1.86 (m, 1H), 0.95-1,18 (m, 6H) |

Example 6

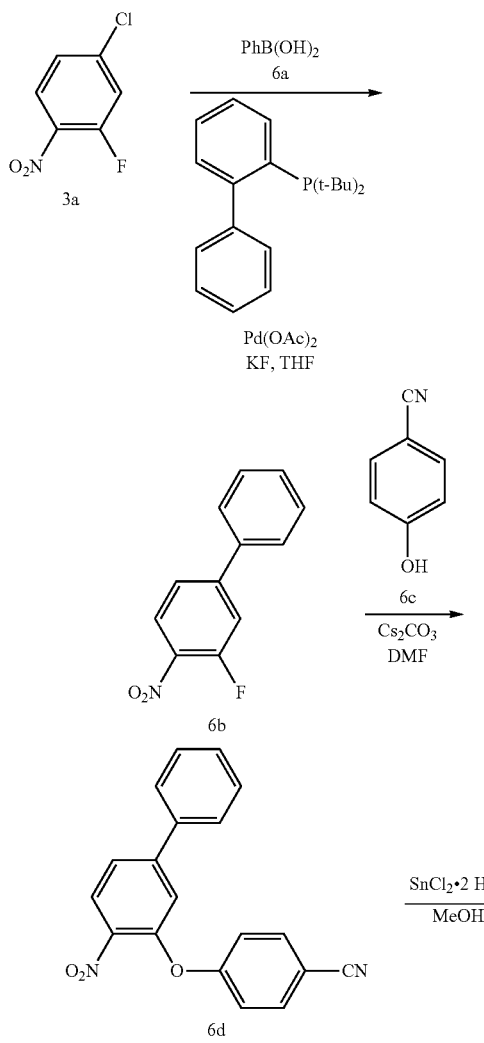

-continued

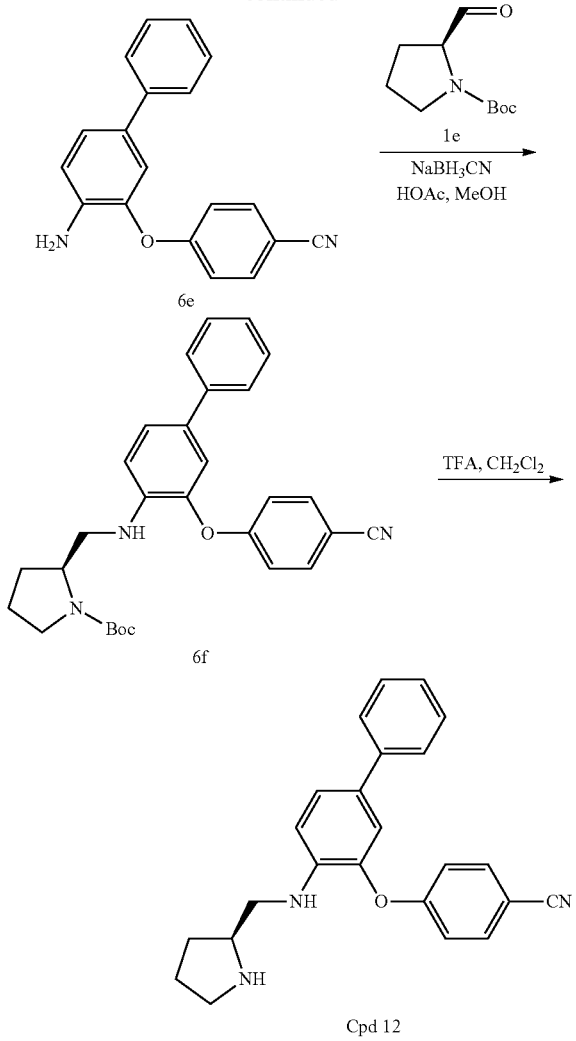

yield). $^1$H NMR (300 MHz, CDCl$_3$): δ 8.12-8.16 (m, 1H), 7.38-7.66 (m, 9H), 7.06-7.09 (m, 2H).

C. 4-(4-Amino-biphenyl-3-yloxy)-benzonitrile (6e). A mixture of compound 6d (1.0 mmol) and tin (II) chloride dihydrate (1.13 g, 5 mmol) in 10 mL of MeOH was refluxed for 2.5 h. After cooling to room temperature, solvent was removed by evaporation and the residue was mixed with water. The aqueous solution was adjusted to pH 9 using saturated aqueous NaHCO$_3$ and the mixture was extracted with EtOAc. The organic layer was dried over Na$_2$SO$_4$ and evaporated to give Compound 6e as a brown solid that was used without purification. MS: m/z 287.2 (M+H)$^+$.

D. 2-(S)-{[3-(4-Cyano-phenoxy)-biphenyl-4-ylamino]-methyl}-pyrrolidine-1-carboxylic acid tert-butyl ester (6f). NaBH$_3$CN (0.066 g, 1.0 mmol) was added to a mixture of Compound 6e (0.14 g, 0.50 mmol) and Compound 1e (0.10 g, 0.50 mmol) in 4 mL of MeOH and 0.3 mL of HOAc. The mixture was stirred at 20° C. for 1.5 h. After evaporation of solvent, the residue was extracted with EtOAc. The organic layer was washed successively with saturated aqueous NaHCO$_3$ and brine and was dried over MgSO$_4$. Concentration and purification by preparative TLC afforded Compound 6f as a brown oil (0.167 g, 71% yield). MS: m/z 470.2 (M+H)$^+$.

E. Cpd 12. (S)-4-{4-[(Pyrrolidin-2-ylmethyl)-amino]-biphenyl-3-yloxy}-benzonitrile. A mixture of Compound 6f (0.167 g, 0.36 mmol), TFA, and CH$_2$Cl$_2$ was stirred at 20° C. for 2 h. After concentration, the residue was dissolved in CH$_3$CN and purified by reverse phase HPLC to afford Cpd 12 as a TFA salt (0.029 g, 13% yield). MS: m/z 370.2 (M+H)$^+$.

Following the procedure described above for Example 6 and substituting the appropriate reagents, starting materials, and purification methods known to those skilled in the art, the following compounds of the present invention were prepared:

A. 3-Fluoro-4-nitrobiphenyl (6b). 4-Chloro-2-fluoronitrobenzene (Compound 3a, 3.51 g, 20 mmol), phenylboronic acid (Compound 6a, 3.77 g, 30 mmol), potassium fluoride (3.49 g, 60 mmol), Pd(OAc)$_2$ (0.045 g, 0.2 mmol), and 2-(di-t-butylphosphino)biphenyl (0.12 g, 0.4 mmol) were added to a dry, nitrogen-swept flask. The flask was evacuated and flushed with nitrogen three times, and THF (25 mL) was added. The reaction mixture was stirred at ambient temperature for 20 h. EtOAc was added and the organic solution was washed successively with 1N aqueous NaOH and brine, dried over MgSO$_4$, and concentrated. The crude product was purified by flash column chromatography (SiO$_2$), eluting with a hexanes-EtOAc gradient to afford pure Compound 6b (1.27 g, 30% yield) and an additional quantity of less pure Compound 6b (3.66 g). $^1$H NMR (300 MHz, CDCl$_3$): δ 8.12-8.18 (m, 1H), 7.47-7.62 (m, 7H).

B. 4-(4-Nitro-biphenyl-3-yloxy)-benzonitrile (6d). Compound 6b (0.22 g, 1.0 mmol), 4-hydroxybenzonitrile (Compound 6c, 0.19 g, 1.5 mmol), Cs$_2$CO$_3$ (0.98 g, 3.0 mmol), and 4 mL of DMF were heated with stirring at 120° C. for 3.5 h. The reaction mixture was poured onto water and extracted with EtOAc. The organic layer was washed successively with 3N aqueous NaOH, 2N aqueous HCl, and brine and dried over Na$_2$SO$_4$. After removal of solvent, crude Compound 6d was isolated and used without purification (0.263 g, 83%

| Cpd | MS (M + H)$^+$ | $^1$H NMR |
|---|---|---|
| 13 | 370.2 | $^1$H NMR (300 MHz, CD$_3$OD): δ 7.18-7.52 (m, 11H), 7.00-7.03 (m, 1H), 3.80-3.90 (m, 1H), 3.48-3.52 (m, 2H), 3.26-3.31 (m, 2H), 2.02-2.24 (m, 3H), 1.75-1.82 (m, 1H) |
| 14 | 345.1 | $^1$H NMR (300 MHz, CD$_3$OD): δ 7.03-7.48 (m, 7H), 7.07-7.12 (m, 1H), 6.95-7.04 (m, 5H), 3.85-3.96 (m, 1H), 3.48-3.54 (m, 2H), 3.26-3.31 (m, 2H), 2.03-2.30 (m, 3H), 1.70-1.84 (m, 1H) |
| 15 | 375.1 | $^1$H NMR (300 MHz, CD$_3$OD): δ 7.44-7.46 (m, 2H), 7.32-7.38 (m, 3H), 7.21-7.24 (m, 2H), 7.10 (m, 1H), 6.95-6.98 (m, 1H), 6.56-6.69 (m, 3H), 3.85-3.96 (m, 1H), 3.76 (s, 3H), 3.48-3.53 (m, 2H), 3.26-3.30 (m, 2H), 1.97-2.30 (m, 3H), 1.73-1.86 (m, 1H) |
| 16 | 363.0 | $^1$H NMR (300 MHz, CD$_3$OD): δ 7.42-7.45 (m, 2H), 7.30-7.37 (m, 3H), 7.21-7.24 (m, 1H), 6.94-7.22 (m, 6H), 3.85-3.96 (m, 1H), 3.48-3.54 (m, 2H), 3.27-3.33 (m, 2H), 1.99-2.32 (m, 3H), 1.74-1.87 (m, 1H) |
| 17 | 428.9 | $^1$H NMR (300 MHz, CD$_3$OD): δ 6.97-7.50 (m, 12H), 3.83-3.95 (m, 1H), 3.40-3.53 (m, 2H), 3.27-3.31 (m, 2H), 2.00-2.28 (m, 3H), 1.77-1.82 (m, 2H) |
| 18 | 412.8 | $^1$H NMR (300 MHz, CD$_3$OD): δ 7.53-7.55 (m, 2H), 7.23-7.32 (m, 7H), 6.93-6.96 (m, 1H), 6.46 (m, 1H), 3.95-4.08 (m, 1H), 3.59-3.63 (m, 2H), 3.31-3.36 (m, 2H), 2.09-2.38 (m, 3H), 1.82-1.93 (m, 1H) |
| 19 | 348.9 | $^1$H NMR (300 MHz, CD$_3$OD): δ 7.18-7.40 (m, 6H), 6.89-7.02 (m, 6H), 3.79 (s, 3H), 3.56-3.60 (m, 2H), 3.26-3.30 (m, 2H), 2.74 (s, 3H) |
| 20 | 402.9 | $^1$H NMR (300 MHz, CD$_3$OD): δ 7.98-8.02 (m, 2H), 7.43-7.50 (m, 3H), 7.35-7.37 (m, 2H), 7.19-7.23 (m, 2H), 6.99-7.06 (m, 3H), 3.82-3.94 (m, 1H), 3.87 (s, 3H), 3.48-3.52 (m, 2H), 3.25-3.31 (m, 2H), 1.93-2.28 (m, 3H), 1.71-1.83 (m, 1H) |
| 21 | 402.9 | $^1$H NMR (300 MHz, CD$_3$OD): δ 7.73-7.76 (m, 1H), 7.60 (m, 1H), 7.23-7.50 (m, 8H), 7.13 (m, 1H), 6.99-7.02 (m, 1H), 3.84-3.95 (m, 1H), 3.88 (s, 3H), 3.49-3.54 (m, 2H), 3.26-3.30 (m, 2H), 1.98-2.29 (m, 3H), 1.75-1.83 (m, 1H) |

-continued

| Cpd | MS (M + H)+ | 1H NMR |
|---|---|---|
| 22 | 412.8 | 1H NMR (300 MHz, CD3OD): δ 7.56 (m, 1H), 7.18-7.40 (m, 7H), 6.91-6.99 (m, 3H), 3.89-3.95 (m, 1H), 3.53-3.56 (m, 2H), 3.28-3.34 (m, 2H), 2.00-2.27 (m, 3H), 1.76-1.83 (m, 1H) |
| 23 | 375.0 | 1H NMR (300 MHz, CD3OD): δ 7.23-7.44 (m, 6H), 6.93-7.10 (m, 6H), 3.76-3.88 (m, 1H), 3.79 (s, 3H), 3.44-3.48 (m, 2H), 3.14-3.18 (m, 2H), 2.25-2.32 (m, 2H), 1.70-1.84 (m, 2H) |

Example 7

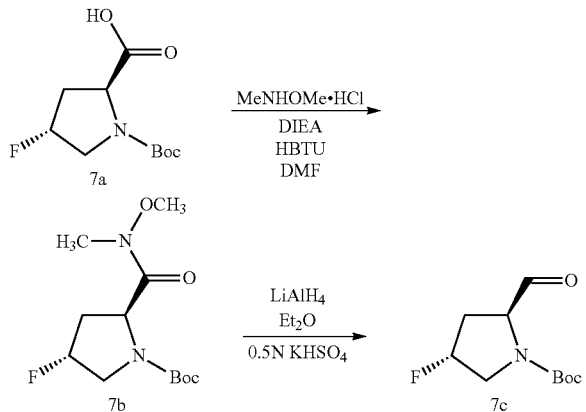

A. (2S,4R)-4-Fluoro-2-(methoxy-methyl-carbamoyl)-pyrrolidine-1-carboxylic acid tert-butyl ester (7b). HBTU (12.3 g, 32.3 mmol) was added in portions to a solution of Compound 7a (6.26 g, 26.9 mmol), N,O-dimethylhydroxylamine hydrochloride (3.15 g, 32.3 mmol), and DIEA (5.62 mL, 4.17 g, 32.3 mmol) in 60 mL of DMF at 0° C. After 15 min, the cooling bath was removed and the mixture was stirred 16 h at 20° C. EtOAc (200 mL) and saturated aqueous NH4Cl (100 mL) were added. The organic layer was separated, washed with saturated aqueous NaHCO3 (100 mL), and brine (100 mL), and dried over MgSO4. The solution was concentrated to give 7.7 g of off-white oil that was purified by flash column chromatography (SiO2), eluting with 10% MeOH/CH2Cl2, to yield Compound 7b (5.47 g, 74% yield). 1H-NMR (DMSO-d6): δ 5.29 (1H, dt), 4.70 (1H, dd), 3.50 (2H, m), 3.13 (3H, s), 2.69 (3H, s), 2.00 (2H, m), 1.34 (9H, s).

B. (2S,4R)-4-Fluoro-2-formyl-pyrrolidine-1-carboxylic acid tert-butyl ester (7c). A 1M solution of LiAlH4 in Et2O (19.2 mL, 19.2 mmol) was added in dropwise to a solution of Compound 7b (3.54 g, 12.8 mmol) in 10 mL of Et2O at 0° C. The mixture was stirred for 1.5 h at 20° C. 10 mL of 0.5 N saturated aqueous KHSO4 was added, followed by 25 mL of Et2O. The organic layer was separated and washed with 1N aqueous NaOH to break up the aluminum complex. The organic layer was separated, dried over MgSO4, and concentrated to provide Compound 7c as an oil (1.33 g, 48% yield).

1H-NMR (DMSO-d6): δ 9.45 (1H, s) 5.10 (1H, m), 4.20 (1H, m), 3.50 (2H, m), 2.20 (2H, m), 1.48 (9H, s).

Example 8

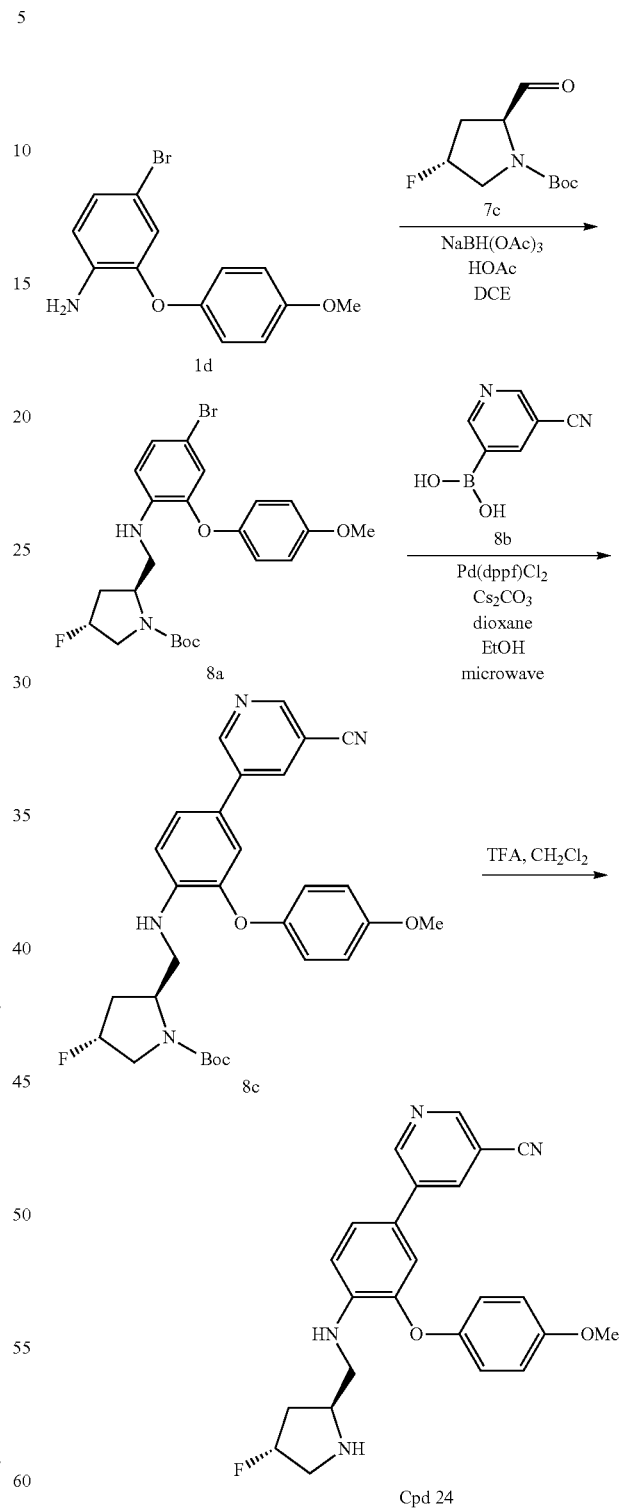

A. (2S,4R)-2-{[4-Bromo-2-(4-methoxy-phenoxy)-phenylamino]-methyl}-4-fluoro-pyrrolidine-1-carboxylic acid tert-butyl ester (8a). A mixture of Compound 1d (1.18 g, 4.0 mmol), Compound 7c (1.33 g, 6.1 mmol), and 5 drops of HOAc in 10 mL of DCE was stirred for 5 min at 20° C. NaBH(OAc)3 (2.54 g, 12 mmol) was added in portions over a 5 min period and the mixture was stirred at 20° C. for 20 h. Saturated aqueous NH₄Cl (25 mL) was added to the stirring mixture, followed by 100 mL of CH₂Cl₂ and 10 mL of water. The organic layer was separated and the aqueous layer was extracted with 50 mL of CH₂Cl₂. The combined organic layers were dried over Na2SO4 and concentrated to give 2 g of crude product. This material was purified by flash column chromatography (SiO₂), eluting with a hexanes-EtOAc gradient, to yield Compound 8a (0.496 g, 25% yield). MS: m/z 495.0/497.0 (M+H)⁺.

B. (2S,4R)-2-{[4-(5-Cyano-pyridin-3-yl)-2-(4-methoxy-phenoxy)-phenylamino]-methyl}-4-fluoro-pyrrolidine-1-carboxylic acid tert-butyl ester (8c). A mixture of Compound 8a (0.124 g, 0.30 mmol), Compound 8b (0.096 g, 0.65 mmol), Pd(dppf)Cl₂ (0.055 g, 0.075 mmol), Cs₂CO₃ (0.244 g, 0.75 mmol), 0.25 mL of EtOH, and 1 mL of dioxane was irradiated in a microwave reactor at 140° C. for 15 min. The reaction mixture was filtered and the solid was washed with 100 mL of EtOAc. The filtrate was washed with saturated aqueous K₂CO₃ dried over Na₂SO₄ and charcoal, and concentrated to afford 0.32 g of crude residue containing Compound 8c.

C. Cpd 24: (2S,4R)-5-[4-[(4-Fluoro-pyrrolidin-2-ylmethyl)-amino]-3-(4-methoxy-phenoxy)-phenyl]-nicotinonitrile. TFA (5 mL) was added dropwise to a solution of the residue from Step B above in 10 mL of CH₂Cl₂ The mixture was stirred for 4 h at 20° C. and was then evaporated. The residue was purified by reverse phase HPLC to afford Cpd 24 as a TFA salt (0.058 g, 36% yield for 2 steps). ¹H NMR (300 MHz, CD₃OD): 8.76 (1H, d), 8.63 (1H, d), 8.14 (1H, d), 7.31 (1H, dd), 6.98-6.82 (6H, m), 5.37 (1H, d), 4.12 (1H, m), 3.65-3.40 (5H, m), 2.50 (1H, m), 1.95 (1H, m); MS: m/z 419.1 (M+H)⁺.

Following the procedure described above for Example 8 and substituting the appropriate reagents, starting materials, and purification methods known to those skilled in the art, the following compounds of the present invention were prepared:

| Cpd | MS (M + H)⁺ | ¹H NMR |
|---|---|---|
| 25 | 412.0 | |
| 26 | 440.1 | |
| 27 | 424.3 | ¹H NMR (400-MHz, CDCl₃): δ 8.44 (s 1H); 8.33 (s, 1H); 7.86 (s, 1H); 7.33 (s, 1H); 6.95 (m, 1H); 4.11 (m, 2H); 3.8 (s, 6H); 3.4 (m, 1H); 255 (m, 2H); 2.24-2.01 (m, 2H); 1.24 (m, 1H) |
| 28 | 408.3 | ¹H NMR (400-MHz, CDCl₃): δ 8.7 (s, 1H); 8.5 (m, 2H); 7.5 (s, 1H); 7.2-6.9 (m, 6H); 4.2 (m, 1H); 3.7 (s, 3H); 3.7 (m, 3H); 3.5 (m, 1H);2.85 (m, 3H); 2.56 (s, 3H) |

Example 9

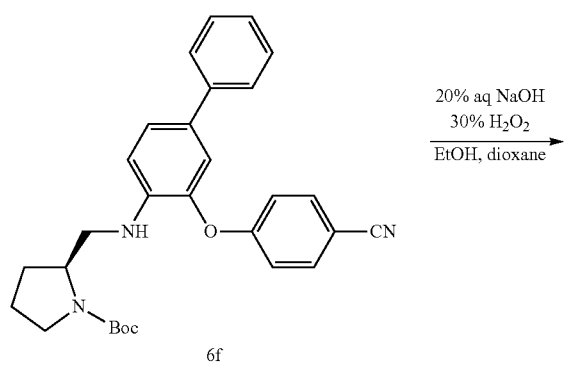

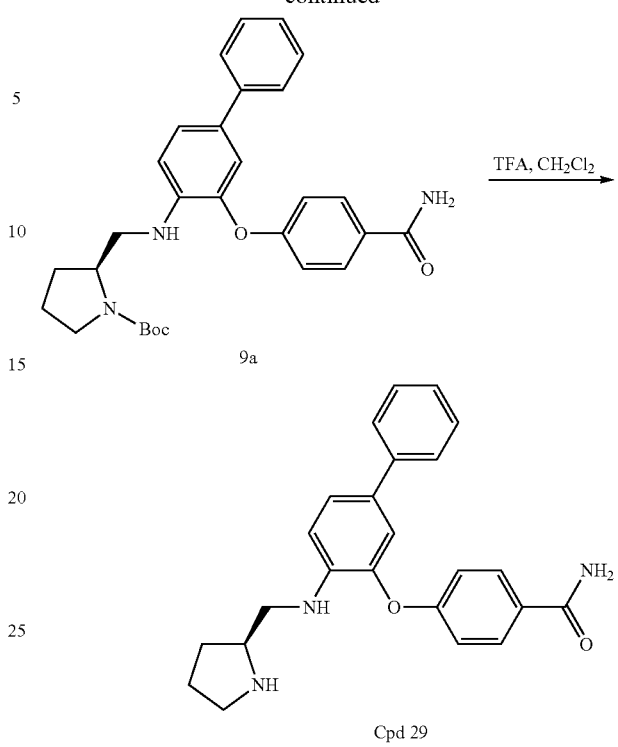

A. 2-(S)-{[3-(4-Carbamoyl-phenoxy)-biphenyl-4-ylamino]-methyl}-pyrrolidine-1-carboxylic acid tert-butyl ester (9a). 20% aqueous NaOH (0.5 mL) and 30% aqueous H₂O₂ (0.4 mL) were added to a solution of compound 6f (0.040 g, 0.085 mmol) in 1.5 mL of EtOH and 1.5 mL of dioxane. The mixture was heated at 60° C. for 2 days. The reaction mixture was extracted with EtOAc, dried over MgSO₄, and concentrated to give Compound 9a. MS: m/z 488.3 (M+H)⁺.

B. Cpd 29: (S)-4-{4-[(Pyrrolidin-2-ylmethyl)-amino]-biphenyl-3-yloxy}-benzamide. A mixture of Compound 9a, TFA, and CH₂Cl₂ was stirred at 20° C. for 2 h. After concentration, the residue was dissolved in CH₃CN and purified by reverse phase HPLC to afford Cpd 29 as a TFA salt (0.015 g, 29% yield for 2 steps). ¹H NMR (300 MHz, CD₃OD): δ 7.87-7.89 (m, 2H), 7.33-7.49 (m, 5H), 7.18-7.19 (m, 2H), 7.00-7.06 (m, 3H), 3.84-3.95 (m, 1H), 3.44-3.57 (m, 2H), 3.28-3.35 (m, 2H), 1.98-2.28 (m, 3H), 1.72-1.82 (m, 1H); MS: m/z 387.9 (M+H)⁺.

Following the procedure described above for Example 9 and substituting the appropriate reagents, starting materials, and purification methods known to those skilled in the art, the following compound of the present invention was prepared:

| Cpd | MS (M + H)⁺ | ¹H NMR |
|---|---|---|
| 30 | 387.9 | ¹H NMR (300 MHz, CD₃OD): δ 7.55-7.58 (m, 1H), 7.31-7.49 (m, 7H), 7.14-7.23 (m, 3H), 6.98-7.00 (m, 1H), 3.85-3.96 (m, 1H), 3.43-3.58 (m, 2H), 3.25-3.31 (m, 2H), 1.98-2.27 (m, 3H), 1.73-1.84 (m, 1H) |

Example 10

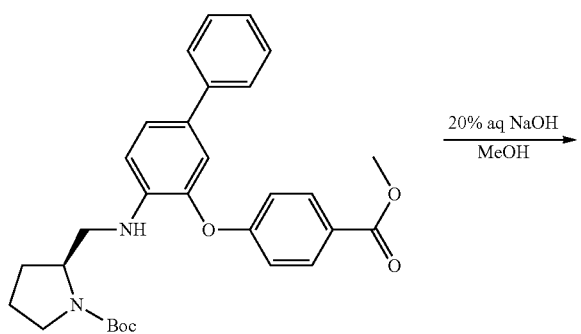

A. 2-(S)-{[3-(4-Methoxycarbonyl-phenoxy)-biphenyl-4-ylamino]-methyl}-pyrrolidine-1-carboxylic acid tert-butyl ester (10a). Compound 10a was prepared according to the method used to prepare Compound 6f described in Example 6 above, substituting methyl 4-hydroxybenzoate for Compound 6c. MS: m/z 503.2 (M+H)$^+$.

B. 2-(S)-{[3-(4-Carboxy-phenoxy)-biphenyl-4-ylamino]-methyl}-pyrrolidine-1-carboxylic acid tert-butyl ester (10b). A mixture of Compound 10a (0.034 g, 0.068 mmol), 20% aqueous NaOH, and MeOH was stirred at 20° C. for 20 h. After evaporation of the MeOH, the aqueous phase was acidified and extracted with EtOAc. The organic layer was washed with brine, dried over Na$_2$SO$_4$, and concentrated to give Compound 10b (0.032 g, 95% yield). MS: m/z 489.2 (M+H)$^+$.

C. Cpd 31: (S)-4-{4-[(Pyrrolidin-2-ylmethyl)-amino]-biphenyl-3-yloxy}-benzoic acid. A mixture of Compound 10b (0.032 g, 0.065 mmol), TFA, and CH$_2$Cl$_2$ was stirred at 20° C. for 2 h. After concentration, the residue was dissolved in CH$_3$CN and purified by reverse phase HPLC to afford Cpd 31 as a TFA salt (0.019 g, 47% yield). $^1$H NMR (300 MHz, CD$_3$OD): δ 7.98-8.13 (m, 2H), 7.43-7.50 (m, 3H), 7.32-7.37 (m, 2H), 7.20-7.25 (m, 2H), 6.99-7.05 (m, 3H), 3.83-3.96 (m, 1H), 3.42-3.58 (m, 2H), 3.25-3.30 (m, 2H), 1.95-2.28 (m, 3H), 1.70-1.83 (m, 1H): MS: m/z 389.0 (M+H)$^+$.

Following the procedure described above for Example 10 and substituting the appropriate reagents, starting materials, and purification methods known to those skilled in the art, the following compound of the present invention was prepared:

| Cpd | MS (M + H)$^+$ | $^1$H NMR |
|---|---|---|
| 32 | 389.0 | $^1$H NMR (300 MHz, CD$_3$OD): δ 7.74-7.79 (m, 1H), 7.61-7.62 (m, 1H), 7.14-7.48 (m, 9H), 6.97-7.00 (m, 1H), 3.87-3.90 (m, 1H), 3.49-3.53 (m, 2H), 3.25-3.32 (m, 2H), 1.99-2.22 (m, 3H), 1.73-1.80 (m, 1H) |

Example 11

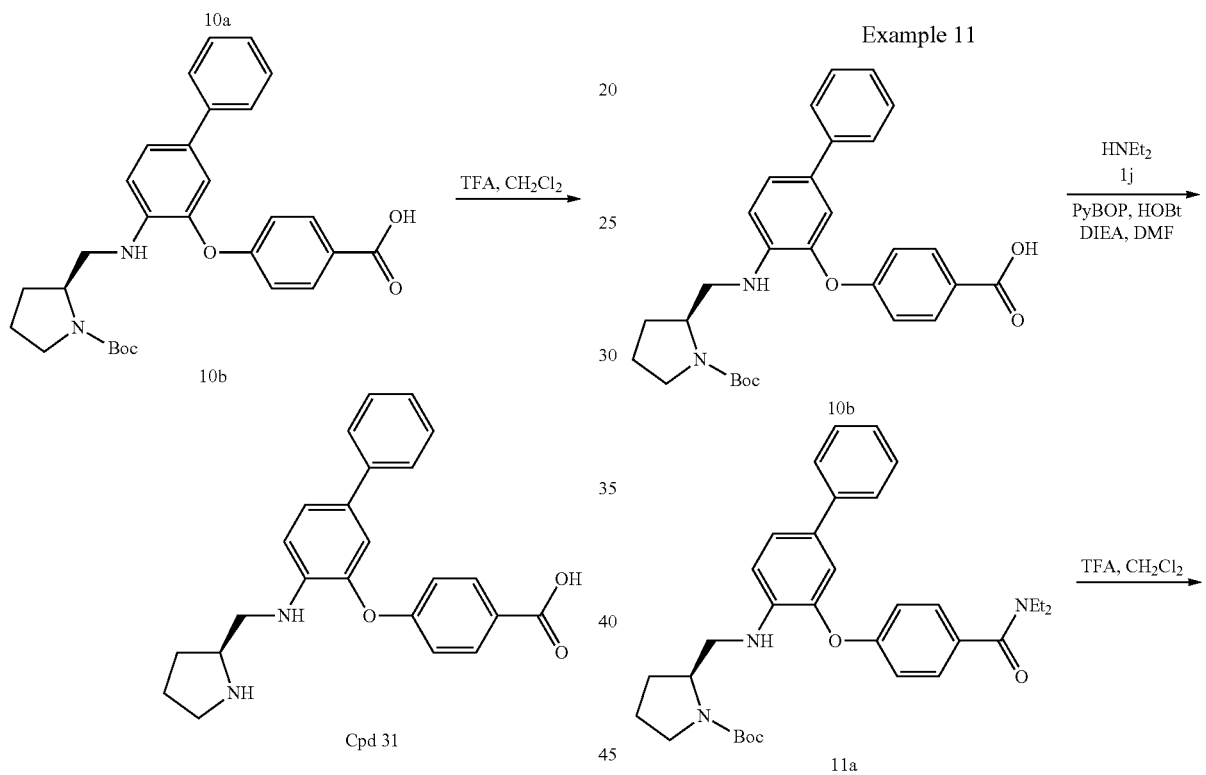

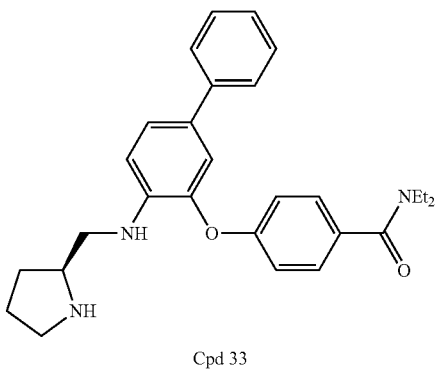

A. 2-(S)-{[3-(4-Diethylcarbamoyl-phenoxy)-biphenyl-4-ylamino]-methyl}-pyrrolidine-1-carboxylic acid tert-butyl ester (11a). A mixture of Compound 10b (0.021 g, 0.043 mmol), Compound 1j (0.0094 g, 0.0013 mL, 0.129 mmol), PyBOP (0.045 g, 0.086 mmol), HOBt (0.0087 g, 0.065 mmol), DIEA (0.011 g, 0.015 mL, 0.086 mmol), and 1 mL of DMF was stirred at 20° C. for 3 h. Water was added and the mixture was extracted with EtOAc. The organic layer was washed successively with 1N aqueous HCl, saturated aqueous NaHCO$_3$, and brine and was dried over MgSO$_4$. Evaporation of solvent and purification by reverse phase HPLC gave Compound 11a. MS: m/z 544.3 (M+H)$^+$.

B. Cpd 33: (S)—N,N-Diethyl-4-{4-[(pyrrolidin-2-ylmethyl)-amino]-biphenyl-3-yloxy}-benzamide. A mixture of Compound 11a, TFA, and CH$_2$Cl$_2$ was stirred at 20° C. for 2 h. After concentration, the residue was dissolved in CH$_3$CN and purified by reverse phase HPLC to afford Cpd 33 as a TFA salt (0.016 g, 55% yield for 2 steps). $^1$H NMR (300 MHz, CD$_3$OD): δ 7.32-7.50 (m, 7H), 7.23-7.25 (m, 1H), 7.16 (m, 1H), 7.05-7.09 (m, 2H), 6.98-7.01 (m, 1H), 3.87-3.91 (m, 1H), 3.44-3.56 (m, 4H), 3.26-3.35 (m, 4H), 2.02-2.23 (m, 3H), 1.74-1.81 (m, 1H), 1.09-1.28 (m, 6H); MS: m/z 444.0 (M+H)$^+$.

Following the procedure described above for Example 11 and substituting the appropriate reagents, starting materials, and purification methods known to those skilled in the art, the following compound of the present invention was prepared:

| Cpd | MS (M + H)$^+$ | $^1$H NMR |
|---|---|---|
| 34 | 444.0 | $^1$H NMR (300 MHz, CD$_3$OD): δ 7.31-7.48 (m, 6H), 6.88-7.24 (m, 6H), 3.87-3.92 (m, 1H), 3.42-3.58 (m, 4H), 3.22-3.32 (m, 4H), 2.19-2.25 (m, 1H), 2.01-2.08 (m, 2H), 1.73-1.80 (m, 1H), 1.17-1.22 (m, 3H), 1.00-1.04 (m, 3H) |

Example 12

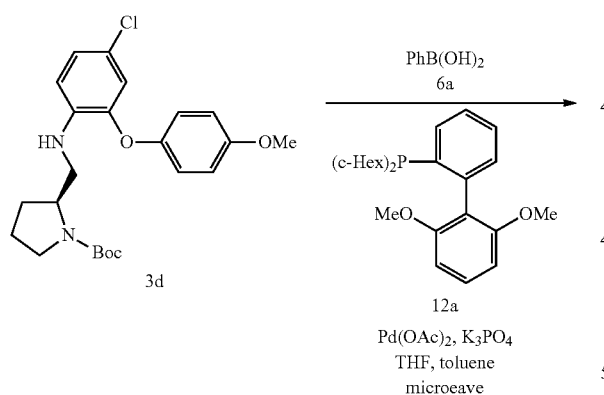

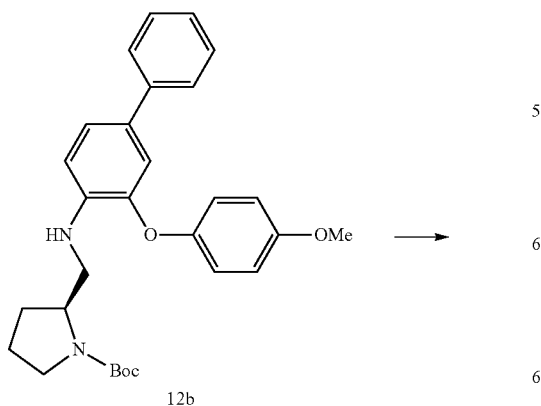

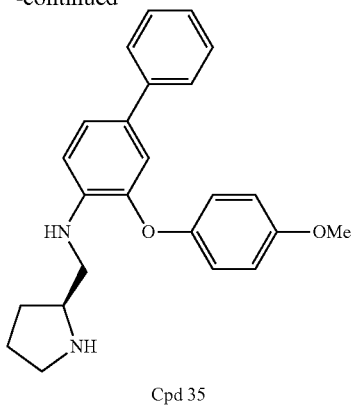

Cpd 35

A. 2-(S)-{[3-(4-Methoxy-phenoxy)-biphenyl-4-ylamino]-methyl}-pyrrolidine-1-carboxylic acid tert-butyl ester (12b). A microwave reaction vessel containing a mixture of Compound 3d (0.070 g, 0.16 mmol), Compound 6a (0.030 g, 0.24 mmol), Pd(OAc)$_2$ (0.0034 g, 0.015 mmol), Compound 12a (0.016 g, 0.039 mmol), and K$_3$PO$_4$ (0.064 g, 0.30 mmol) was evacuated and flushed with nitrogen three times. Toluene (0.5 mL) and THF (0.3 mL) were added and the mixture was irradiated in a microwave reactor at 160° C. for 30 min. The reaction mixture was filtered and the concentrated filtrate was purified by preparative TLC to give Compound 12b (0.050 g, 66% yield). MS: m/z 475.2 (M+H)$^+$.

B. Cpd 35: (S)-[3-(4-Methoxy-phenoxy)-biphenyl-4-yl]-pyrrolidin-2-ylmethyl-amine. A mixture of Compound 12b (0.050 g, 0.11 mmol), TFA, and CH$_2$Cl$_2$ was stirred at 20° C. for 1 h. After concentration, the residue was dissolved in CH$_3$CN and purified by reverse phase HPLC to afford Cpd 35 as a TFA salt (0.0063 g, 9% yield). $^1$H NMR (300 MHz, CD$_3$OD): δ 6.68-7.50 (m, 12H), 4.08-4.14 (m, 1H), 3.78-3.83 (m, 1H), 3.80 (s, 3H), 3.56-3.61 (m, 1H), 3.32-3.41 (m, 2H), 2.00-2.27 (m, 3H), 1.77-1.88 (m, 1H); MS: m/z 375.1 (M+H)$^+$.

Example 13

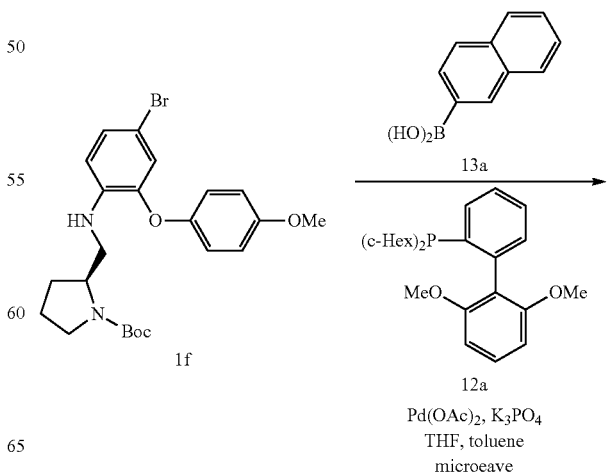

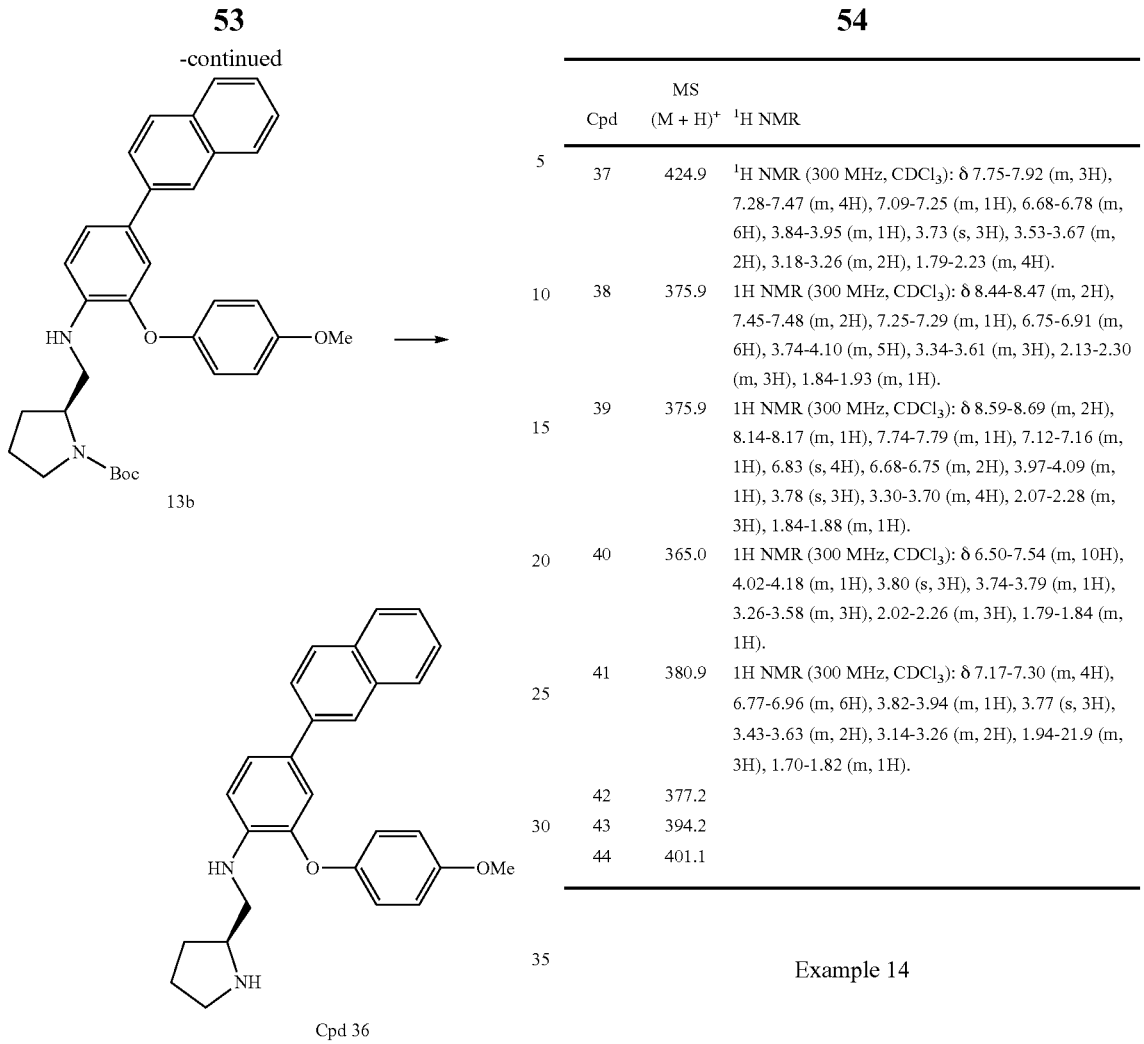

| Cpd | MS (M + H)+ | 1H NMR |
|---|---|---|
| 37 | 424.9 | 1H NMR (300 MHz, CDCl3): δ 7.75-7.92 (m, 3H), 7.28-7.47 (m, 4H), 7.09-7.25 (m, 1H), 6.68-6.78 (m, 6H), 3.84-3.95 (m, 1H), 3.73 (s, 3H), 3.53-3.67 (m, 2H), 3.18-3.26 (m, 2H), 1.79-2.23 (m, 4H). |
| 38 | 375.9 | 1H NMR (300 MHz, CDCl3): δ 8.44-8.47 (m, 2H), 7.45-7.48 (m, 2H), 7.25-7.29 (m, 1H), 6.75-6.91 (m, 6H), 3.74-4.10 (m, 5H), 3.34-3.61 (m, 3H), 2.13-2.30 (m, 3H), 1.84-1.93 (m, 1H). |
| 39 | 375.9 | 1H NMR (300 MHz, CDCl3): δ 8.59-8.69 (m, 2H), 8.14-8.17 (m, 1H), 7.74-7.79 (m, 1H), 7.12-7.16 (m, 1H), 6.83 (s, 4H), 6.68-6.75 (m, 2H), 3.97-4.09 (m, 1H), 3.78 (s, 3H), 3.30-3.70 (m, 4H), 2.07-2.28 (m, 3H), 1.84-1.88 (m, 1H). |
| 40 | 365.0 | 1H NMR (300 MHz, CDCl3): δ 6.50-7.54 (m, 10H), 4.02-4.18 (m, 1H), 3.80 (s, 3H), 3.74-3.79 (m, 1H), 3.26-3.58 (m, 3H), 2.02-2.26 (m, 3H), 1.79-1.84 (m, 1H). |
| 41 | 380.9 | 1H NMR (300 MHz, CDCl3): δ 7.17-7.30 (m, 4H), 6.77-6.96 (m, 6H), 3.82-3.94 (m, 1H), 3.77 (s, 3H), 3.43-3.63 (m, 2H), 3.14-3.26 (m, 2H), 1.94-21.9 (m, 3H), 1.70-1.82 (m, 1H). |
| 42 | 377.2 | |
| 43 | 394.2 | |
| 44 | 401.1 | |

Example 14

A. 2-(S)-{[2-(4-Methoxy-phenoxy)-4-naphthalen-2-yl-phenylamino]-methyl}-pyrrolidine-1-carboxylic acid tert-butyl ester (13b). A mixture of Compound 1f (0.14 g, 0.30 mmol), Compound 13a (0.077 g, 0.45 mmol), Pd2(dba)3 (0.0011 g, 0.012 mmol), Compound 12a (0.010 g, 0.024 mmol), K3PO4 (0.13 g, 0.60 mmol), and 0.6 mL of toluene was irradiated in a microwave reactor at 160° C. for 30 min. The reaction mixture was filtered and the concentrated filtrate was purified by preparative TLC to give Compound 13b. MS: m/z 425.2 (M−Boc)+.

B. Cpd 36: (S)-[2-(4-Methoxy-phenoxy)-4-naphthalen-2-yl-phenyl]-pyrrolidin-2-ylmethyl-amine. A mixture of Compound 13b, TFA, and CH2Cl2 was stirred at 20° C. for 1.5 h. After concentration, the residue was dissolved in CH3CN and purified by reverse phase HPLC to afford Cpd 36 as a TFA salt (0.0084 g, 3% yield for 2 steps). 1H NMR (300 MHz, CDCl3): δ 7.78-7.81 (m, 4H), 7.32-7.55 (m, 4H), 7.11 (m, 1H), 6.83-6.99 (m, 5H), 3.84-3.95 (m, 1H), 3.7 (s, 3H), 3.50-3.70 (m, 2H), 3.26 (m, 2H), 1.98-2.23 (m, 3H), 1.73-1.83 (m, 1H); MS: m/z 425.0 (M+H)+.

Following the procedure described above for Example 13 and substituting the appropriate reagents, starting materials, and purification methods known to those skilled in the art, the following compounds of the present invention were prepared:

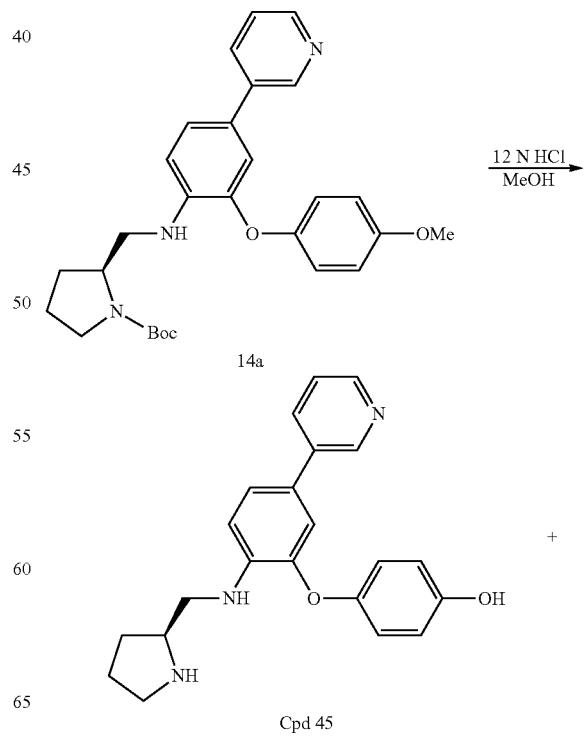

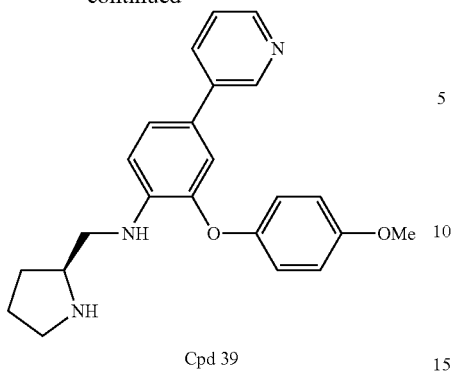

Cpd 39

A. 2-{[2-(4-methoxy-phenoxy)-4-pyridin-3-yl-phenylamino]-methyl}-pyrrolidine-1-carboxylic acid tert-butyl ester (14a). Compound 14a was prepared according to the method described in Example 13 above, substituting pyridine-3-boronic acid for Compound 13a. MS: m/z 476.3 (M+H)⁺.

B. Cpd 45: (S)-4-{5-Pyridin-3-yl-2-[(pyrrolidin-2-ylmethyl)-amino]-phenoxy}-phenol. A mixture of Compound 14a (0.18 g, 0.38 mmol), 2 mL of concentrated (12 N) HCl, and 2 mL of MeOH was stirred at 20° C. for 3 h. After concentration, the residue was purified by preparative TLC, eluting with MeOH:CH$_2$Cl$_2$. The product was taken up in MeOH, filtered, and concentrated to give a yellow solid. This material was neutralized with saturated aqueous NaHCO$_3$ and extracted into EtOAc. The organic phase was washed with water, concentrated to a small volume, filtered through a 0.4 μm filter disk, and acidified with 2N aqueous HCl. The EtOAc was evaporated and the residue was dissolved in water, filtered, and lyophilized. The resulting material was purified by reverse phase HPLC. The fractions containing Cpd 39 were concentrated, neutralized with saturated aqueous NaHCO$_3$, and extracted with EtOAc. The organic phase was washed with water and concentrated; the residue was dissolved in dilute aqueous HCl, filtered, and lyophilized to give Cpd 39 as an HCl salt (0.195 g). The fractions containing Cpd 45 were concentrated and lyophilized to give Cpd 45 as a TFA salt (0.013 g). MS: m/z 362.2 (M+H)⁺.

Example 15

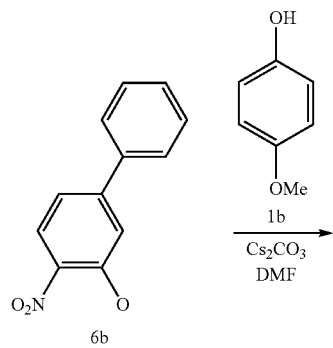

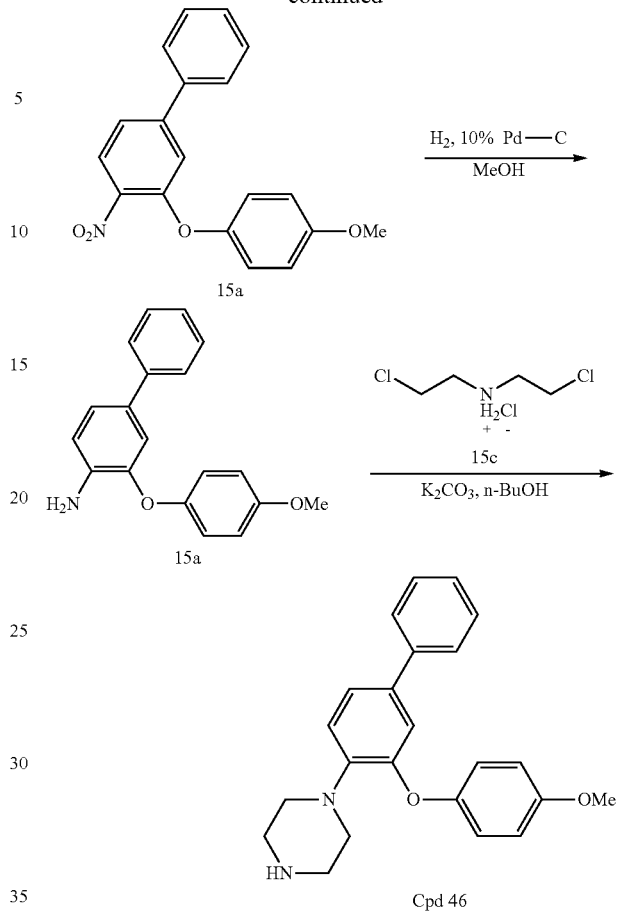

Cpd 46

A. 3-(4-Methoxy-phenoxy)-4-nitrobiphenyl (15a). Compound 6b (0.22 g, 1.0 mmol), Compound 1b (0.19 g, 1.5 mmol), Cs$_2$CO$_3$ (0.98 g, 3.0 mmol), and 4 mL of DMF were heated with stirring at 120° C. for 3 h. The reaction mixture was poured onto ice water and the resulting solid was collected by filtration. The solid was dissolved in EtOAc and dried over Na$_2$SO$_4$. After removal of solvent, Compound 15a was isolated as a brown oil that was used without purification (0.45 g, ~140% yield). ¹H NMR (300 MHz, CDCl$_3$): δ 8.02 (m, 1H), 7.32-7.47 (m, 6H), 7.06-7.10 (m, 3H), 6.91-6.94 (m, 2H), 3.82 (s, 3H).

B. 3-(4-Methoxy-phenoxy)-biphenyl-4-ylamine (15b). A mixture of compound 15a (~1.0 mmol) and 10% palladium on carbon in MeOH was shaken under a hydrogen atmosphere (34 psi) at 20° C. for 3 h. The catalyst was filtered and solvent was removed by evaporation to give Compound 15b as a brown oil that was used without purification (0.33 g, 113% yield). MS: m/z 292.2 (M+H)⁺.

C. Cpd 46: 1-[3-(4-Methoxy-phenoxy)biphenyl-4-yl]piperazine. A mixture of Compound 15b (0.16 g, 0.55 mmol), bis-(2-chloroethyl)ammonium chloride (Compound 15c, 0.10 g, 0.55 mmol), K$_2$CO$_3$ (0.038 g, 0.275 mmol) and 2 mL of n-butanol was heated at reflux for 42 h. After cooling to room temperature, brine was added and the mixture was extracted with EtOAc. The organic layer was dried over MgSO$_4$ and concentrated to give crude residue that was purified by reverse phase HPLC to afford Cpd 46 as a TFA salt. ¹H NMR (300 MHz, CD$_3$OD): δ 7.47-7.50 (m, 2H), 7.37-7.41 (m, 3H), 7.28-7.31 (m, 1H), 7.12-7.19 (m, 2H), 6.92-6.94 (m, 4H), 3.77 (s, 3H), 3.35-3.39 (m, 4H), 3.18-3.22 (m, 4H); MS: m/z 360.9 (M+H)⁺.

Example 16

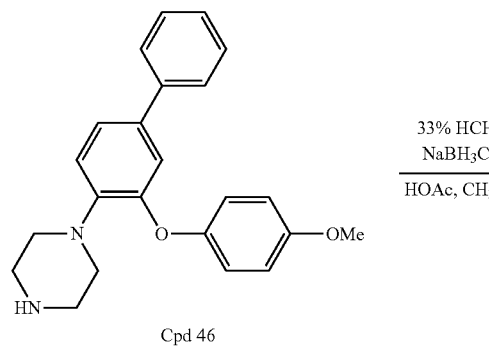

Cpd 46

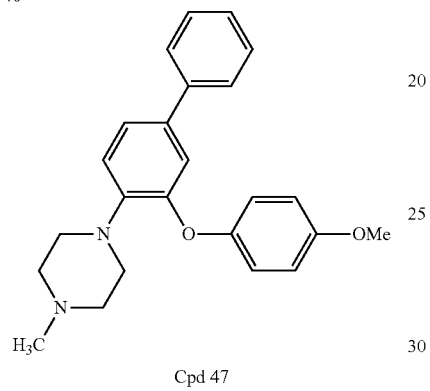

Cpd 47

Cpd 47: 1-[3-(4-Methoxy-phenoxy)biphenyl-4-yl]-4-methyl-piperazine. To a stirring solution of Cpd 46 (0.090 g, 0.25 mmol) and 37% aqueous formaldehyde (0.5 mL) in 0.5 mL of acetonitrile was added sodium cyanoborohydride (0.06 g, 0.9 mmol) and 0.5 mL of acetic acid. The resulting mixture was stirred at 20° C. for 3 h, and then was quenched by adding saturated aqueous $NaHCO_3$. Solvent was removed by evaporation and the aqueous residue was extracted with EtOAc. The organic layer was washed successively with 1N aqueous NaOH, 1N aqueous HCl, and brine, dried over $Na_2SO_4$, and concentrated. The resulting crude residue was purified by reverse phase HPLC to afford Cpd 47 as a TFA salt. $^1$H NMR (300 MHz, $CD_3OD$): δ 7.16-7.48 (m, 7H), 7.09 (m, 1H), 6.92 (m, 4H), 3.77 (s, 3H), 3.68-3.72 (m, 2H), 3.52-3.55 (m, 2H), 3.07-3.13 (m, 4H), 2.90 (s, 3H); MS: m/z 374.9 (M+H)$^+$.

Example 17

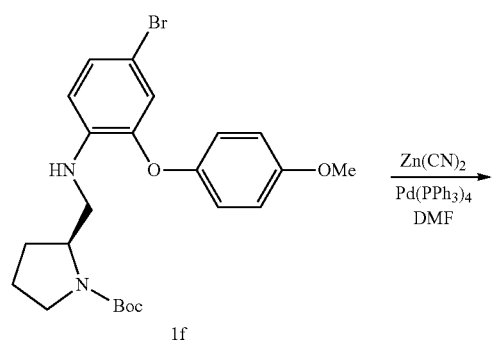

1f

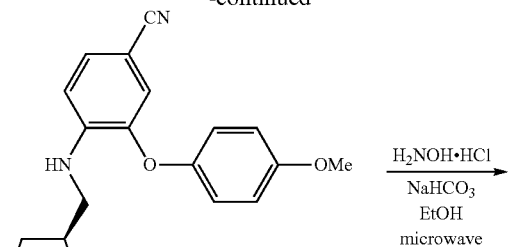

17a

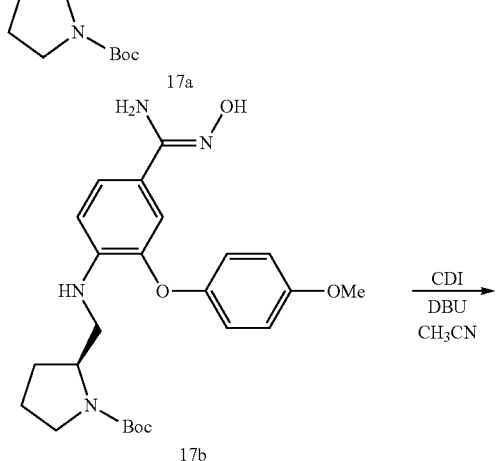

17b

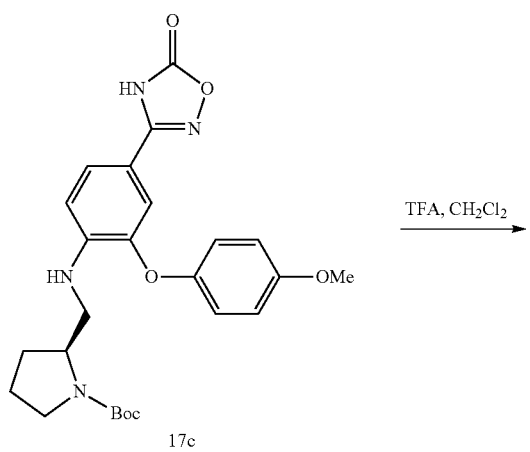

17c

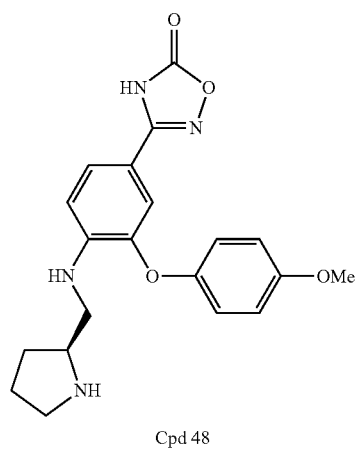 [SMILES: COc1ccc(Oc2cc(-c3noc(=O)[nH]3)ccc2NC[C@@H]2CCCN2)cc1]

Cpd 48

A. 2-(S)-{[4-Cyano-2-(4-methoxy-phenoxy)-phenylamino]-methyl}-pyrrolidine-1-carboxylic acid tert-butyl ester (17a). A mixture of Compound 1f (0.13 g, 0.30 mmol), zinc (II) cyanide (0.036 mmol, 0.30 mmol), and Pd(PPh$_3$)$_4$ (0.017 g, 0.015 mmol) in 1.2 mL of DMF was irradiated in a microwave reactor at 160° C. for 6 min. The residue was purified by preparative TLC, eluting with 1:1 EtOAc:hexanes, to give Compound 17a (0.080 g, 63% yield). MS: m/z 426.2 (M+H)$^+$.

B. 2-(S)-{[4-(N-Hydroxycarbamimidoyl)-2-(4-methoxy-phenoxy)-phenylamino]-methyl}-pyrrolidine-1-carboxylic acid tert-butyl ester (17b). Hydroxylamine hydrochloride (0.023 g, 0.32 mmol), NaHCO$_3$ (0.040 g, 0.48 mmol), and 0.2 mL of water were stirred until CO$_2$ evolution ceased. A suspension of compound 17a (0.069 g, 0.16 mmol) in 0.5 mL of EtOH was added. The mixture was irradiated in a microwave reactor at 160° C. for 16 min. After evaporation of the solvent, the residue was dissolved in EtOAc and purified by preparative TLC, eluting with 1:1 EtOAc:hexanes, to give Compound 17b (0.038 g, 52% yield). MS: m/z 459.3 (M+H)$^+$.

C. 2-(S)-{[2-(4-Methoxy-phenoxy)-4-(5-oxo-4,5-dihydro-[1,2,4]oxadiazol-3-yl)-phenylamino]-methyl}-pyrrolidine-1-carboxylic acid tert-butyl ester (17c). DBU (0.071 g, 0.069 mL, 0.464 mmol) was added to a stirring solution of Compound 17b (0.053 g, 0.116 mmol) and 1,1'-carbonyldiimidazole (0.021 g, 0.128 mmol) in 1 mL of CH$_3$CN. The mixture was stirred under N$_2$ for 2 days and was then purified by filtration through a solid-phase extraction (SPE) column. Evaporation of the solvent afforded Compound 17c. MS: m/z 483.2 (M+H)$^+$.

D. Cpd 48: (S)-3-{3-(4-Methoxy-phenoxy)-4-[(pyrrolidin-2-ylmethyl)-amino]-phenyl}-4H-[1,2,4]oxadiazol-5-one. A mixture of Compound 17c (0.048 g, 0.099 mmol), TFA, and CH$_2$Cl$_2$ was stirred at 20° C. for 4 h. After concentration, the residue was purified by reverse phase HPLC to afford Cpd 48 as a TFA salt (0.018 g, 30% yield. $^1$H NMR (300 MHz, CD$_3$OD): δ 7.39 (d, 1H), 6.92-7.07 (m, 6H), 3.88-3.98 (m, 1H), 3.80 (s, 3H), 3.53-3.60 (m, 2H) 3.30-3.33 (m, 2H), 2.23-2.31 (m, 1H), 2.05-2.13 (m, 2H), 1.75-1.88 (m, 1H); MS: m/z 383.1 (M+H)$^+$.

Example 18

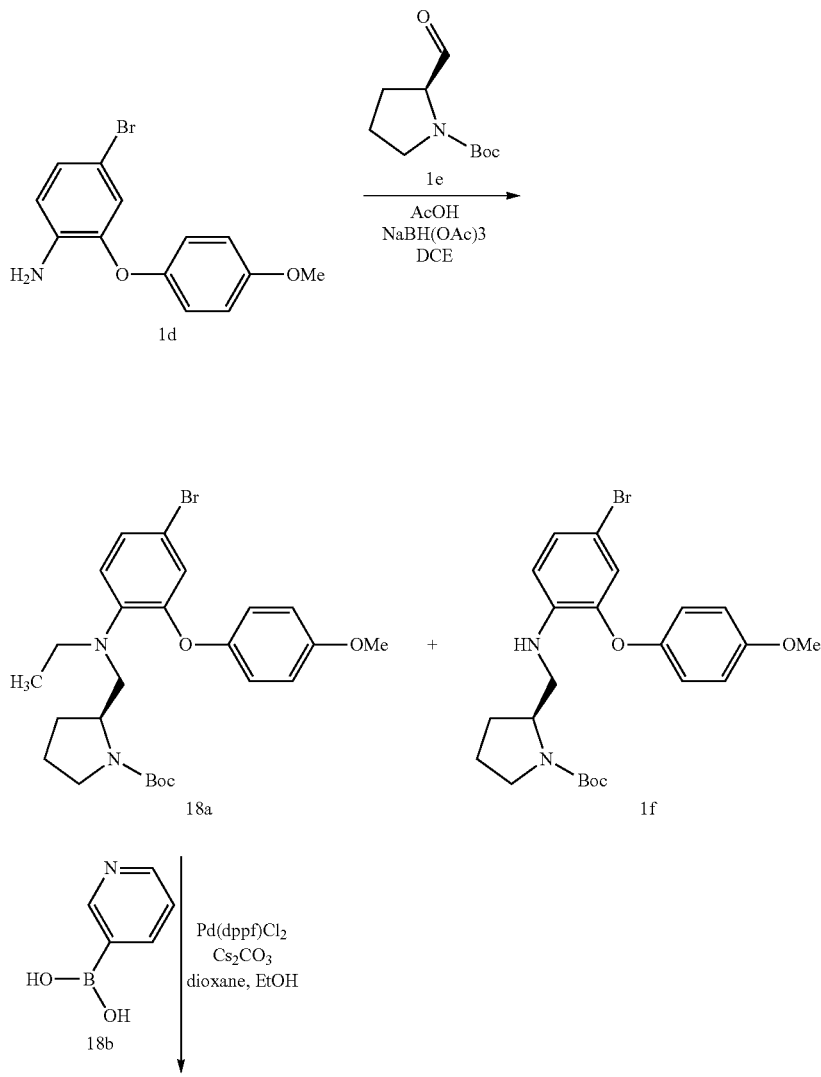

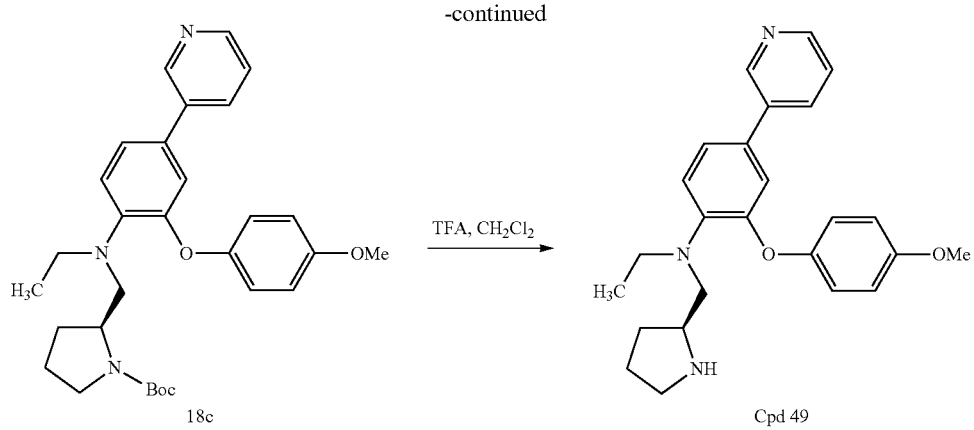

A. 2-(S)-({[4-Bromo-2-(4-methoxy-phenoxy)-phenyl]-ethyl-amino}-methyl)-pyrrolidine-1-carboxylic acid tert-butyl ester (18a). A mixture of Compound 1d (11.8 g, 40 mmol) and Compound 1e in 5 mL of HOAc and 60 mL of 1,2-dichloroethane was stirred for 1 h at 20° C. NaBH(OAc)$_3$ was added in portions over a 15 min period, and the mixture was allowed to stir at 20° C. for 2½ days. Saturated aqueous K$_2$CO$_3$ (200 mL) was added slowly, followed by CH$_2$Cl$_2$ (500 mL). The organic layer was separated, and the aqueous layer was extracted with CH$_2$Cl$_2$ (2×200 mL). The combined organic fractions were dried over MgSO$_4$, treated with charcoal, filtered over Celite, and evaporated to yield 26.9 g of a dark brown oil. The residue was purified via flash column chromatography (SiO$_2$), eluting with a hexanes-EtOAc gradient to yield Compound 1f (6.93 g, 36% yield) and Compound 18a (6.63 g, 33% yield). MS: m/z 505.1/507.1 (M+H)$^+$.

B. 2-(S)-({Ethyl-[2-(4-methoxy-phenoxy)-4-pyridin-3-yl-phenyl]-amino}-methyl)-pyrrolidine-1-carboxylic acid tert-butyl ester (18c). A mixture of Compound 18a (0.51 g, 1 mmol), Compound 18b (0.307 g, 2.5 mmol), Pd(dppf)Cl$_2$ (0.183 g, 0.25 mmol), Cs$_2$CO$_3$ (0.977 g, 3.0 mmol), 0.5 mL of EtOH, and 2.5 mL of dioxane was irradiated in a microwave reactor at 140° C. for 15 min. The reaction mixture was filtered and the solid was washed with 100 mL of EtOAc. The filtrate was washed with 30 mL of saturated aqueous K$_2$CO$_3$ dried over Na$_2$SO$_4$ and charcoal, and concentrated to afford 0.36 g of crude residue containing Compound 18c.

C. Cpd 49: (S)-Ethyl-[2-(4-methoxy-phenoxy)-4-pyridin-3-yl-phenyl]-pyrrolidin-2-ylmethyl-amine. TFA (5 mL) was added dropwise to a solution of the residue from Step B above in 10 mL of CH$_2$Cl$_2$ The mixture was stirred for 4 h at 20° C. and was then evaporated. The residue was dissolved in 100 mL of CH$_2$Cl$_2$ and washed with 20 mL of 1N aqueous NaOH. The organic layer was dried over Na$_2$SO$_4$ and concentrated. The residue was purified by reverse phase HPLC. Fractions containing the desired product were concentrated, dissolved in 100 mL of CH$_2$Cl$_2$, and washed with 10 mL of 1N aqueous NaOH. The organic layer was dried over Na$_2$SO$_4$, concentrated redissolved in CH$_2$Cl$_2$, treated with 6 mL of 1N HCl in Et$_2$O, and evaporated to afford a lightly yellow solid, Cpd 49, as an HCl salt (0.130 g, 27% yield for 2 steps). $^1$H NMR (300 MHz, DMSO-d$_6$): 9.64 (1H, s, broad), 9.20 (1H, d), 8.93, 1H, s, broad), 8.84 (1H, d), 8.78 (1H, d), 8.07 (1H, dd), 7.71 (1H, dd), 7.46 (1H, d), 7.42 (1H, d), 7.00 (4H, m), 3.79 (3H, s), 3.7-3.1 (7H, m), 2.0-1.75 (3H, m), 1.55 (1H, m), 1.02 (3H, t); MS: m/z 404.2 (M+H)$^+$.

Following the procedure described above for Example 18 and substituting the appropriate reagents, starting materials, and purification methods known to those skilled in the art, the following compounds of the present invention were prepared:

| Cpd | MS (M + H)$^+$ |
|---|---|
| 50 | 422.2 |
| 51 | 405.1 |
| 52 | 429.1 |

Example 19

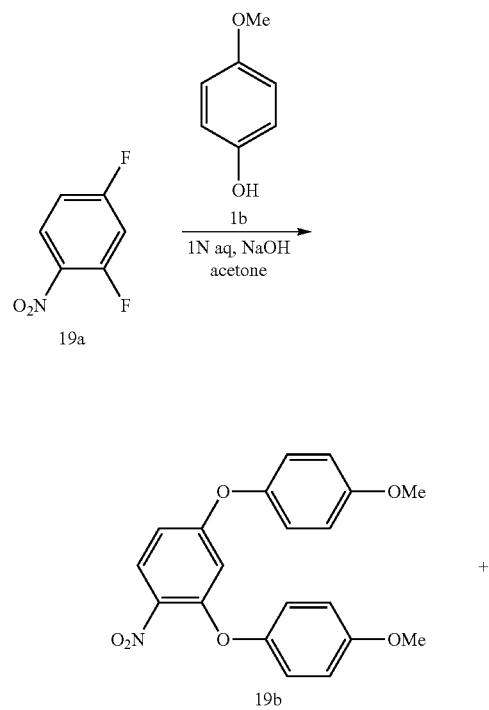

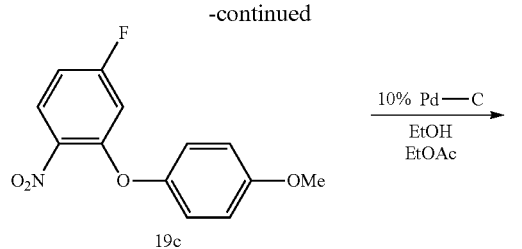
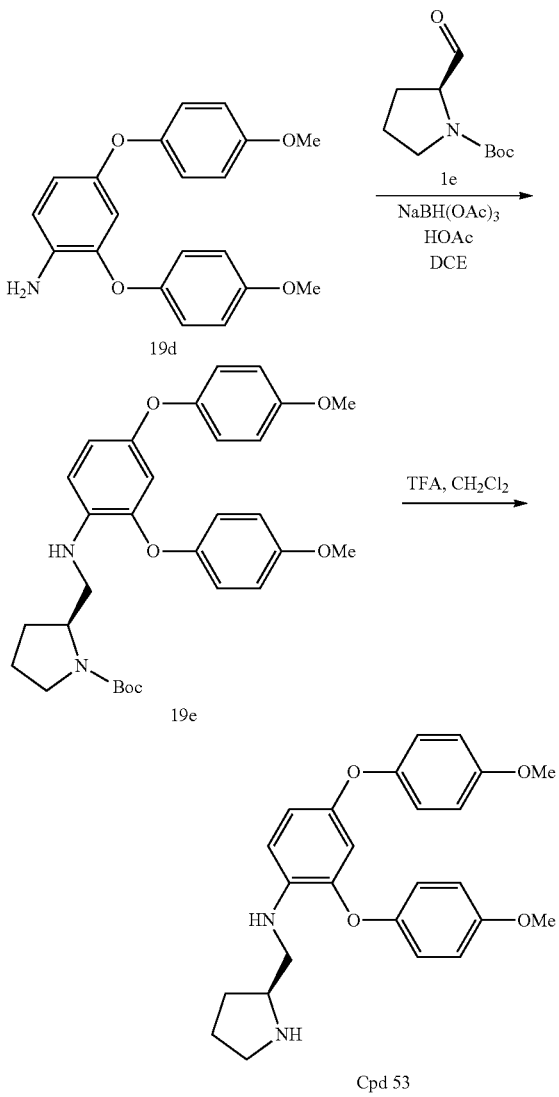

A. 2,4-Bis-(4-methoxy-phenoxy)-nitrobenzene (19b). A solution of 2,4-difluoronitrobenzene (Compound 19a, 0.5 g, 3.1 mmol) in 15 mL of acetone was added to a mixture of Compound 1b (0.86 g, 6.9 mmol) and 6.9 mL of 1N aqueous NaOH in 5 mL of acetone. The mixture was heated at 55° C. for 3 days and then at 80° C. for 5 h. The reaction mixture was concentrated to remove acetone and the residue was loaded onto a 10 mL solid-phase extraction (SPE) column. Elution with $CH_2Cl_2$ and concentration of the eluent yielded 1.5 g of a 1:4 mixture of Compound 19c and Compound 19b that was used without purification. MS: m/z 368 $(M+H)^+$.

B. 2,4-Bis-(4-methoxy-phenoxy)-aniline (19d). The mixture containing Compounds 19b and 19c prepared in Step A were combined with 50 mg of 10% Pd—C in 50 mL of EtOH/EtOAc and stirred at 20° C. under a hydrogen atmosphere (14.7 psi) for 17 h. The mixture was filtered through Celite and concentrated. The residue was taken up in MeOH, filtered through a 0.4 µm filter disk, and concentrated to give Compound 19d. MS: m/z 338.1 $(M+H)^+$.

C. (S)-2-{[2,4-Bis-(4-methoxy-phenoxy)-phenylamino]-methyl}-pyrrolidine-1-carboxylic acid tert-butyl ester (19e). A mixture of Compound 19d (0.051 g, 0.15 mmol), Compound 1e (0.033 g, 0.31 mL, 0.17 mmol), HOAc (0.017 mL, 0.3 mmol), and 0.4 mL of DCE was stirred at 20° C. for 2.5 h. $NaBH(OAc)_3$ (0.089 g, 0.42 mmol) was added and the mixture was stirred at 20° C. for 20 h. The reaction mixture was purified using a 1 mL SPE column, eluting with $CH_2Cl_2$, to give Compound 19e.

D. Cpd 53: (S)-[2,4-Bis-(4-methoxy-phenoxy)-phenyl]-pyrrolidin-2-ylmethyl-amine. Compound 19e was dissolved in 50% $TFA/CH_2Cl_2$ and stirred at 20° C. for 45 min. After concentration, the residue was purified by reverse phase HPLC to afford Cpd 53 as a TFA salt (0.082 g, 84% yield). MS: m/z 421.2 $(M+H)^+$.

Following the procedure described above for Example 19 and substituting the appropriate reagents, starting materials, and purification methods known to those skilled in the art, the following compounds of the present invention were prepared:

| Cpd | MS $(M+H)^+$ |
|---|---|
| 54 | 421.1 |
| 55 | 411.1 |
| 56 | 421.1 |
| 57 | 447.0 |
| 60 | 447.2 |
| 61 | 435.2 |
| 62 | 435.2 |

Example 20

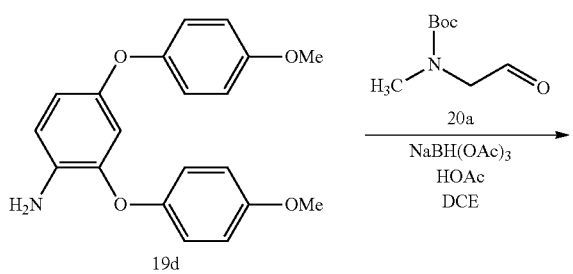

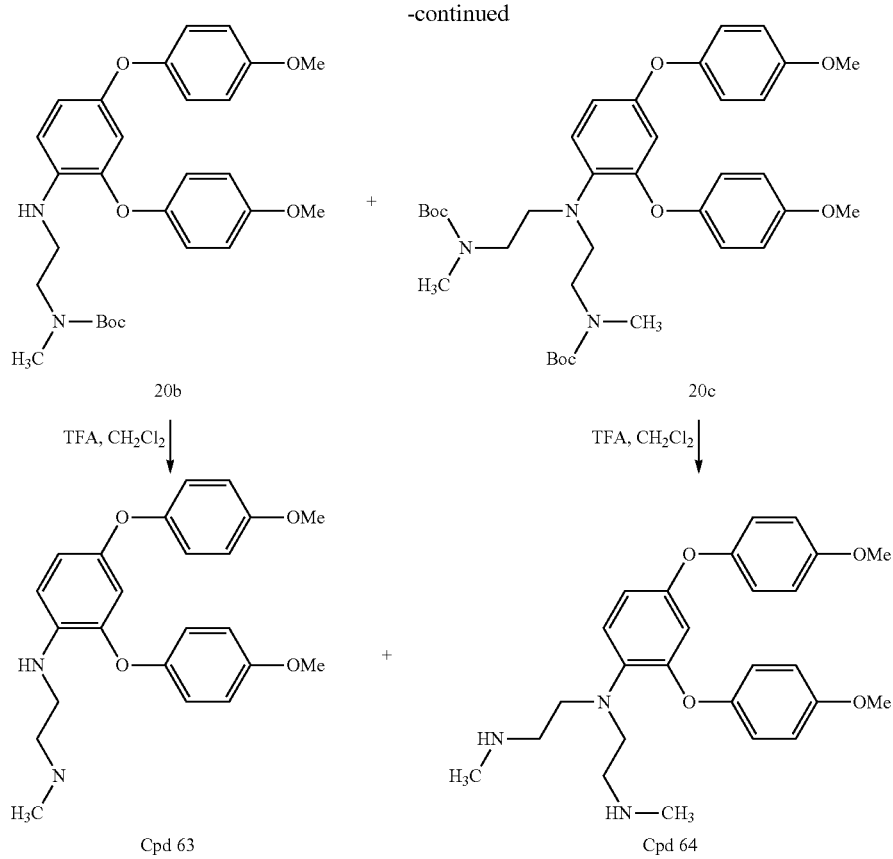

A. {2-[2,4-Bis-(4-methoxy-phenoxy)-phenylamino]-ethyl}-methyl-carbamic acid tert-butyl ester (20b); and (2-{[2,4-Bis-(4-methoxy-phenoxy)-phenyl]-[2-(tert-butoxy-carbonyl-methyl-amino)-ethyl]-amino}-ethyl)-methyl-carbamic acid tert-butyl ester (20c). HOAc (0.034 mL, 0.59 mmol) and NaBH(OAc)$_3$ (0.175 g, 0.83 mmol) were added to a solution of Compound 19d (0.102 g, 0.30 mmol) and Compound 20a (0.112 g, 0.32 mL, 0.17 mmol) in DCE and the mixture was stirred at 20° C. for 18 h. Water (0.2 mL) was added and the reaction mixture was purified using a 3 mL SPE column, eluting with CH$_2$Cl$_2$, to give a mixture of Compound 20b and Compound 20c.

B. Cpd 63: N-[2,4-Bis-(4-methoxy-phenoxy)-phenyl]-N'-methyl-ethane-1,2-diamine; and Cpd 64: N-[2,4-Bis-(4-methoxy-phenoxy)-phenyl]-N'-methyl-N-(2-methylamino-ethyl)-ethane-1,2-diamine.

The mixture of Compound 20b and Compound 20c prepared in Step A was dissolved in TFA/CH$_2$Cl$_2$ and stirred at 20° C. After concentration, the residue was purified by reverse phase HPLC to afford Cpd 63 (0.139 g, 62% yield) and Cpd 64 (0.013 g, 5.6% yield), each as a TFA salt. Cpd 63: MS: m/z 395.2 (M+H)$^+$. Cpd 64: MS: m/z 452.3 (M+H)$^+$.

Following the procedure described above for Example 20 and substituting the appropriate reagents, starting materials, and purification methods known to those skilled in the art, the following compounds of the present invention were prepared:

| Cpd | MS (M + H)$^+$ |
|---|---|
| 58 | 407.1 |
| 59 | 476.3 |

Compounds 1 through 64 of Formula (I) in the table below were synthesized using the procedures described above.

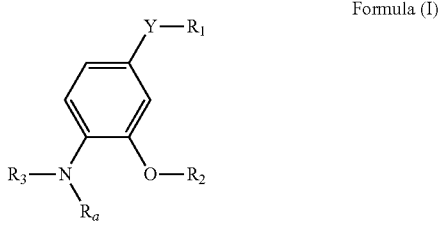

Formula (I)

TABLE 1

| Cpd No. | R$_1$ | Y | R$_2$ | R$_3$ | R$_a$ | R$_3$—N—R$_a$ | R$_3$ stereo chem |
|---|---|---|---|---|---|---|---|
| 1 | 2-(N,N-diethylamino carbonyl) | (E)-vinyl- | 4-methoxy-phenyl | pyrrolidin-2-yl methyl | H | | 2S |

TABLE 1-continued

| Cpd No. | R₁ | Y | R₂ | R₃ | Rₐ | R₃—N—Rₐ | R₃ stereo chem |
|---|---|---|---|---|---|---|---|
| 2 | 2-(N,N-diethylamino carbonyl) | ethyl | 4-methoxy-phenyl | pyrrolidin-2-yl methyl | H | | 2S |
| 3 | 2-(4-methoxy-phenyl) | ethyl | 4-methoxy-phenyl | pyrrolidin-2-ylmethyl | H | | 2S |
| 4 | 2-(3-methoxy-phenyl) | ethyl | 4-methoxy-phenyl | pyrrolidin-2-yl methyl | H | | 2S |
| 5 | 2-phenyl | ethyl | 4-methoxy-phenyl | pyrrolidin-2-yl methyl | H | | 2S |
| 6 | 2-(4-fluoro-phenyl) | ethyl | 4-methoxy-phenyl | pyrrolidin-2-yl methyl | H | | 2S |
| 7 | 2-(3-fluoro-phenyl) | ethyl | 4-methoxy-phenyl | pyrrolidin-2-yl methyl | H | | 2S |
| 8 | 2-[3-(N,N-diethylamino carbonyl)phenyl] | ethyl | 4-methoxy-phenyl | pyrrolidin-2-yl methyl | H | | 2S |
| 9 | N,N-diethylamino carbonyl | a bond | phenyl | pyrrolidin-2-yl methyl | H | | 2S |
| 10 | N,N-diethylamino carbonyl | a bond | 4-methoxy-phenyl | pyrrolidin-2-yl methyl | H | | 2S |
| 11 | N,N-diethylamino carbonyl | a bond | 2-methoxy-phenyl | pyrrolidin-2-yl methyl | H | | 2S |
| 12 | phenyl | a bond | 4-cyano-phenyl | pyrrolidin-2-yl methyl | H | | 2S |
| 13 | phenyl | a bond | 3-cyano-phenyl | pyrrolidin-2-yl methyl | H | | 2S |
| 14 | phenyl | a bond | phenyl | pyrrolidin-2-yl methyl | H | | 2S |
| 15 | phenyl | a bond | 3-methoxy-phenyl | pyrrolidin-2-yl methyl | H | | 2S |
| 16 | phenyl | a bond | 4-fluoro-phenyl | pyrrolidin-2-yl methyl | H | | 2S |
| 17 | phenyl | a bond | 4-trifluoro methoxy-phenyl | pyrrolidin-2-yl methyl | H | | 2S |
| 18 | phenyl | a bond | 2,6-dichloro-phenyl | pyrrolidin-2-yl methyl | H | | 2S |
| 19 | phenyl | a bond | 4-methoxy-phenyl | 2-(N-methylamino)ethyl | H | | |
| 20 | phenyl | a bond | 4-methoxy carbonyl-phenyl | pyrrolidin-2-yl methyl | H | | 2S |
| 21 | phenyl | a bond | 3-methoxy carbonyl-phenyl | pyrrolidin-2-ylmethyl | H | | 2S |
| 22 | phenyl | a bond | 2,4-dichloro-phenyl | pyrrolidin-2-yl methyl | H | | 2S |
| 23 | phenyl | a bond | 4-methoxy-phenyl | piperidin-4-yl | H | | |
| 24 | 5-cyano-pyridin-3-yl | a bond | 4-methoxy-phenyl | 4-fluoro-pyrrolidin-2-yl methyl | H | | 2S,4R |
| 25 | 5-fluoro-pyridin-3-yl | a bond | 4-methoxy-phenyl | 4-fluoro-pyrrolidin-2-yl methyl | H | | 2S,4R |
| 26 | 5-methylthio-pyridin-3-yl | a bond | 4-methoxy-phenyl | 4-fluoro-pyrrolidin-2-yl methyl | H | | 2S,4R |
| 27 | 5-methyoxy-pyridin-3-yl | a bond | 4-methoxy-phenyl | 4-fluoro-pyrrolidin-2-yl methyl | H | | 2S,4R |
| 28 | 5-methyl-pyridin-3-yl | a bond | 4-methoxy-phenyl | 4-fluoro-pyrrolidin-2-yl methyl | H | | 2S,4R |
| 29 | phenyl | a bond | 4-amino carbonyl-phenyl | pyrrolidin-2-yl methyl | H | | 2S |
| 30 | phenyl | a bond | 3-amino carbonyl-phenyl | pyrrolidin-2-yl methyl | H | | 2S |
| 31 | phenyl | a bond | 4-carboxy-phenyl | pyrrolidin-2-yl methyl | H | | 2S |
| 32 | phenyl | a bond | 3-carboxy-phenyl | pyrrolidin-2-yl methyl | H | | 2S |

TABLE 1-continued

| Cpd No. | R₁ | Y | R₂ | R₃ | Rₐ | R₃—N—Rₐ | R₃ stereo chem |
|---|---|---|---|---|---|---|---|
| 33 | phenyl | a bond | 4-(N.N-diethylamino carbonyl)phenyl | pyrrolidin-2-yl methyl | H | | 2S |
| 34 | phenyl | a bond | 3-(N.N-diethylamino carbonyl)phenyl | pyrrolidin-2-yl methyl | H | | 2S |
| 35 | phenyl | a bond | 4-methoxy-phenyl | pyrrolidin-2-ylmethyl | H | | 2S |
| 36 | naphthalen-2-yl | a bond | 4-methoxy-phenyl | pyrrolidin-2-yl methyl | H | | 2S |
| 37 | naphthalen-1-yl | a bond | 4-methoxy-phenyl | pyrrolidin-2-yl methyl | H | | 2S |
| 38 | pyridin-4-yl | a bond | 4-methoxy-phenyl | pyrrolidin-2-yl methyl | H | | 2S |
| 39 | pyridin-3-yl | a bond | 4-methoxy-phenyl | pyrrolidin-2-yl methyl | H | | 2S |
| 40 | furan-3-yl | a bond | 4-methoxy-phenyl | pyrrolidin-2-yl methyl | H | | 2S |
| 41 | thiophen-3-yl | a bond | 4-methoxy-phenyl | pyrrolidin-2-yl methyl | H | | 2S |
| 42 | pyrimidin-5-yl | a bond | 4-methoxy-phenyl | pyrrolidin-2-yl methyl | H | | 2S |
| 43 | 5-fluoro-pyridin-3-yl | a bond | 4-methoxy-phenyl | pyrrolidin-2-yl methyl | H | | 2S |
| 44 | 5-cyano-pyridin-3-yl | a bond | 4-methoxy-phenyl | pyrrolidin-2-yl methyl | H | | 2S |
| 45 | pyridin-3-yl | a bond | 4-hydroxy-phenyl | pyrrolidin-2-yl methyl | H | | 2S |
| 46 | phenyl | a bond | 4-methoxy-phenyl | | | piperazin-1-yl | |
| 47 | phenyl | a bond | 4-methoxy-phenyl | | | 4-methyl-piperazin-1-yl | |
| 48 | 5-oxo-4,5-dihydro-[1,2,4]oxadiazol-3-yl | a bond | 4-methoxy-phenyl | pyrrolidin-2-yl methyl | H | | 2S |
| 49 | pyridin-3-yl | a bond | 4-methoxy-phenyl | pyrrolidin-2-yl methyl | ethyl | | 2S |
| 50 | 5-fluoro-pyridin-3-yl | a bond | 4-methoxy-phenyl | pyrrolidin-2-yl methyl | ethyl | | 2S |
| 51 | pyrimidin-5-yl | a bond | 4-methoxy-phenyl | pyrrolidin-2-yl methyl | ethyl | | 2S |
| 52 | 5-cyano-pyridin-3-yl | a bond | 4-methoxy-phenyl | pyrrolidin-2-yl methyl | ethyl | | 2S |
| 53 | 4-methoxy-phenyl | O | 4-methoxy-phenyl | pyrrolidin-2-yl methyl | H | | 2S |
| 54 | 4-methoxy-phenyl | O | 4-methoxy-phenyl | piperidin-3-yl | H | | racemic |
| 55 | 4-methoxy-phenyl | O | 4-methoxy-phenyl | 3-hydroxy-2(R)-amino-propyl | H | | 2R |
| 56 | 4-methoxy-phenyl | O | 4-methoxy-phenyl | piperidin-4-yl | H | | |
| 57 | 4-methoxy-phenyl | O | 4-methoxy-phenyl | 8-azabicyclo[3.2.1]octan-3-yl | H | | mixture of endo/exo isomers |
| 58 | 4-methoxy-phenyl | O | 4-methoxy-phenyl | azetidin-3-yl-methyl | H | | |
| 59 | 4-methoxy-phenyl | O | 4-methoxy-phenyl | azetidin-3-yl-methyl | azetidin-3-yl-methyl | | |
| 60 | 4-methoxy-phenyl | O | 4-methoxy-phenyl | 1-azabicyclo[2.2.2]octan-3-yl | H | | mixture of endo/exo isomers |
| 61 | 4-methoxy-phenyl | O | 4-methoxy-phenyl | piperidin-3-yl methyl | H | | racemic |
| 62 | 4-methoxy-phenyl | O | 4-methoxy-phenyl | 3-amino-cyclohexyl | H | | mixture of 4 isomers |

TABLE 1-continued

| Cpd No. | $R_1$ | Y | $R_2$ | $R_3$ | $R_a$ | $R_3$—N—$R_a$ | $R_3$ stereo chem |
|---|---|---|---|---|---|---|---|
| 63 | 4-methoxy-phenyl | O | 4-methoxy-phenyl | 2-(N-methylamino)ethyl | H | | |
| 64 | 4-methoxy-phenyl | O | 4-methoxy-phenyl | 2-(N-methylamino)ethyl | 2-(N-methylamino)ethyl | | |

BIOLOGICAL EXAMPLES

In Vitro Assays

Example 1

NG108-15, 24-Well Delta Opioid Receptor Binding Assay

Methods: NG108-15 cell membranes were purchased from Applied Cell Sciences (Rockville, Md.). 5 mg/mL of membrane protein suspended in 10 mM TRIS-HCl pH 7.2, 2 mM EDTA, 10% sucrose. With several brief pulses from a Polytron homogenizer, each vial was homogenized in 5 mls of 50 mM Tris Buffer, pH 7.4. The homogenate was diluted in 50 mM Tris Buffer containing 5 mM $MgCl_2$ to 330 ug/ml in the working solution for a final concentration of 133 ug/well. This particulate preparation was used for the 24-well delta opioid binding assay.

Following incubation with the delta selective peptide ligand ~0.2 nM [$^3$H]naltrindole at 25° C. for 2.5 h in a 24-well plate with total volume of 1 mL, the plate contents were filtered through a UniFilter24, GF/B. This plate was pre-soaked in 0.3% PEI and filtered through a 24-well Harvester. The UniFilter24 was rinsed three times with 2 mL of 10 mM HEPES (pH 7.4), and dried in an oven at 37° C. for 1.5 hours. To each well, was added 150 µL of Scint0 (PerkinElmer, Cat #6013611). The plates were then read on a TopCount.

Analysis: The data from the scintillation counter were used to calculate either the % inhibition compared to control binding (when only a single concentration of test compound was evaluated) or a $K_1$ value (when a range of concentrations was tested). Non-specific binding (N.S.-1 mM naloxone) was used as the negative control, while the Total Binding (T.B.-Membrane and ligand only) was used as the positive control. If one concentration was screened, the % inhibition was calculated as (cpms of total binding minus cpms of compound) divided by (cpms of T.B.minus cpms of N.S). The triplicate % Inhibitions were averaged and reported. If multiple concentrations were generated, the values were analyzed using the one-site binding non-linear regression program in Prism to determine $K_i$ values. The bottom and top values are globally shared. The triplicate $K_i$ values are then averaged and reported.

The data obtained are shown in Table 2, below.

Example 2

Rat Brain Delta Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand ~4 nM [$^3$H]DPDPE or 0.25 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 µL of Betaplate Scint scintillation fluid (LKB) was added and the radioactivity was quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_1$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. The data obtained are shown in Table 2, below.

Example 3

Rat Brain Mu Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the mu opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 µL of Betaplate Scint scintillation fluid (LKB) was added and the radioactivity was quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_1$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. The data obtained are shown in Table 2, below.

TABLE 2

Delta and Mu Opioid Receptor Binding Data

| Cpd No. | δ-binding NG108 cell membrane $K_i$ (μM) | δ-binding (DPDPE ligand) $K_i$ (μM) | δ-binding (Naltrindole ligand) $K_i$ (μM) | μ-binding $K_i$ (μM) |
|---|---|---|---|---|
| 1 | | | 0.006081 | 3.3659 |
| 2 | | | 0.02641 | >100 |
| 3 | | | 0.1197 | >10 |
| 4 | | | 0.21 | >10 |
| 5 | | | 0.2395 | >10 |
| 6 | | | 0.6836 | >10 |
| 7 | | | 0.2288 | >10 |
| 8 | | | 0.1269 | 9.00119 |
| 9 | | | 1.023 | >10 |
| 10 | | | 0.9356 | 0.9356 |
| 11 | | 0.1053 | | >10 |
| 12 | | | 0.9959 | >10 |
| 13 | | | 0.4018 | >10 |
| 14 | | | 0.1131 | >10 |
| 15 | | | 0.2886 | >10 |
| 16 | | | 0.4191 | >10 |
| 17 | | | 1.472 | >10 |
| 18 | | | 0.1075 | >10 |
| 19 | | | 0.192 | >10 |
| 20 | | | 0.7789 | >10 |
| 21 | | | 0.8869 | >10 |
| 22 | | | 0.6978 | >10 |
| 23 | | | 0.4615 | >10 |
| 27 | | | 1.001 | >10 |
| 28 | | | 0.006814 | 4.673 |
| 29 | | | 0.1467 | >10 |
| 30 | | | 0.1265 | 5.7956 |
| 31 | | | 7.691 | >10 |
| 32 | | | 2.667 | >10 |
| 33 | | | 0.2843 | 9.30465 |
| 34 | | | 0.3095 | >10 |
| 35 | | 0.02885 | | >10 |
| 36 | | | 0.2905 | >10 |
| 37 | | | 0.3009 | >10 |
| 38 | | | 0.0155 | 4.3621 |
| 39 | 0.001646 | | 0.02213 | 3.1067 |
| 40 | | | 0.2051 | >10 |
| 41 | | | 0.2896 | >10 |
| 42 | 0.001388 | | | |
| 43 | 0.00076 | | | |
| 44 | 0.000436 | | | |
| 45 | | | 0.00542 | 4.4555 |
| 46 | | | 0.07971 | >10 |
| 47 | | | 2.223 | >10 |
| 48 | | 0.492 | | 9.705 |
| 49 | 0.02897 | | | |
| 50 | 0.02303 | | | |
| 51 | 0.077 | | | |
| 52 | 0.009328 | | | |
| 53 | | | 0.1053 | >10 |
| 54 | | 0.492 | | 9.705 |
| 55 | | | 1.367 | >10 |
| 56 | | | 1.729 | >10 |
| 57 | | | 1.43 | >10 |
| 58 | | | 0.7027 | >10 |
| 59 | | | 2.275 | >10 |
| 60 | | | 0.1577 | >10 |
| 61 | | | 0.111 | >10 |
| 62 | | | 0.04088 | 1.6417 |
| 63 | | | 0.02374 | >10 |
| 64 | | | 1.536 | >10 |

Example 4

[$^{35}$S]GTPγS Binding Assay in NG108-15 Cell Membranes (delta opioid functional assay)-200 nM Screen Methods: NG108-15 cell membranes were purchased from Applied Cell Sciences (Rockville, Md.). 5 mg/mL of membrane protein suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM MgCl$_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 μg/mL) were preincubated with SPA (10 mg/mL) at 25° C. for 45 min in the assay buffer. The SPA (5 mg/mL) coupled with membranes (37.5 μg/mL) was then incubated with 0.1 nM [$^{35}$S] GTPγS in the same Tris buffer containing 100 μM GDP in total volume of 200 pt. 200 nM of receptor agonists was used to stimulate [$^{35}$S]-GTPγS binding. The basal binding was tested in the absence of agonists and non-specific binding was tested in the presence of 10 μM unlabeled GTPγS. The data were analyzed on a Packard Top Count and are shown in Table 3, below.

Data

% of Basal=(stimulated−non specific)*100/(basal−non specific).

Relative Efficacy of a compound at 200 nM=(% of Basal of test compound at 200 nM)/(Calculated Max of SNC80 dose response. Curve in prism).

Example 5

[$^{35}$S]GTPγS Binding Assays in CHO-hMOR Cell Membranes (mu opioid functional assay)

Methods: CHO-hMOR cell membranes were purchased from Receptor Biology, Inc. (Baltimore, Md.). About 10 mg/mL of membrane protein was suspended in 10 mM TRIS-HCl pH 7.2, 2 mM EDTA, 10% sucrose, and the suspension kept on ice. A 1 mL volume of membranes was added to 15 mL cold binding assay buffer containing 50 mM HEPES, pH 7.6, 5 mM MgCl$_2$, 100 mM NaCl, 1 mM DTT and 1 mM EDTA. The membrane suspension was homogenized with a Polytron and centrifuged at 3,000 rpm for 10 min. The supernatant can then be centrifuged at 18,000 rpm for 20 min. The pellet was resuspended in 10 mL assay buffer with a Polytron. The membranes were preincubated with wheat germ agglutinin coated SPA beads (Amersham) at 25° C. for 45 min in the assay buffer. The SPA bead (5 mg/mL) coupled membranes (10 μg/mL) were then incubated with 0.5 nM [$^{35}$S] GTPγS in the assay buffer. The basal binding was that taking place in the absence of added test compound; this unmodulated binding was considered as 100%, with agonist stimulated binding rising to levels significantly above this value. A range of concentrations of receptor agonist was used to stimulate [$^{35}$S]GTPγS binding. Both basal and non-specific binding were tested in the absence of agonist; non-specific binding determination included 10 μM unlabeled GTPγS.

Compounds were tested for function as antagonists by evaluating their potential to inhibit agonist-stimulated GTPγS binding. Radioactivity was quantified on a Packard TopCount. The following parameters were calculated:

$$\% \text{ stimulation} = \frac{(\text{test compound } cpm - \text{non-specific } cpm) \times 100}{(\text{basal } cpm - \text{non-specific } cpm)}.$$

$$\% \text{ inhibition} = \frac{\left(\frac{\% \text{ stimulation by 1 } \mu M \text{ DAMGO} -}{\% \text{ stimulation by test compound}}\right) \times 100}{(\% \text{ stimulation by 1 } \mu M \text{ DAMGO} - 100)}$$

EC$_{50}$ values were calculated using GraphPad Prism and are shown in Table 3, below.

TABLE 3-continued

Delta Opioid Receptor Functional Data

| Cpd No. | GTPγS δ-RelEfficacy @200 nM | GTPγS δ-opioid receptor EC$_{50}$ (μM) | GTγPS δ-opioid receptor Rel Efficacy | GTPγS δ-opioid receptor % Inh @10 μM |
|---|---|---|---|---|
| 43 | 0.43 | 0.218 | 1.0908 | |
| 44 | 0.45 | 0.1176 | 1.1554 | |
| 45 | | 0.0408 | 0.627 | 35.642 |
| 53 | | 0.3194 | | 28.165 |
| 61 | | 4.0729 | | 16.134 |
| 62 | | 0.3811 | | 1.733 |
| 63 | | 3.1067 | | 25.97 |

In Vivo Assay

Example 6

Mouse Graded Abdominal Irritant Test (GrAIT)

Test compound or vehicle was administered s.c. or p.o. to mice. Following the pretreatment time, an i.p. injection of 0.6% of acetic acid in 0.5 mL was administered. Five min after acetic acid administration, mice were placed into clear chambers and were continuously observed for 5 min. Behavioral responses including twisting and elongation of the body that extended through the hindlimbs were counted and averaged for the group of animals over the observation period. The results are shown in Table 4 below.

TABLE 4

| Cpd | dose (mg/kg) | vehicle | route of admin. | no. of animals | pretreatment (min) | # abdominal stretches (vehicle) | # abdominal stretches (cpd) |
|---|---|---|---|---|---|---|---|
| 1 | 30 | 10% Solutol | s.c. | 5 | 30 | 14.1 | 10.9 |
| 10 | 30 | 10% Solutol | s.c. | 10 | 30 | 16.7 | 11 |
| 10 | 30 | 10% Solutol | p.o. | 5 | 30 | 19.8 | 19 |
| 10 | 100 | 10% Solutol | p.o. | 10 | 30 | 19.8 | 17.9 |
| 10 | 300 | 10% Solutol | p.o. | 5 | 30 | 19.8 | 21.2 |

TABLE 3

Delta Opioid Receptor Functional Data

| Cpd No. | GTPγS δ-RelEfficacy @200 nM | GTPγS δ-opioid receptor EC$_{50}$ (μM) | GTγPS δ-opioid receptor Rel Efficacy | GTPγS δ-opioid receptor % Inh @10 μM |
|---|---|---|---|---|
| 1 | | 0.1093 | 0.8328 | 2.2554 |
| 2 | | 0.0391 | 0.8333 | 22.78 |
| 11 | | 0.3194 | | |
| 18 | | 1.0428 | 0.763 | 23.395 |
| 24 | 1.01 | 0.0461 | 1.0158 | |
| 25 | 0.78 | 0.0924 | 1.0217 | |
| 26 | 0.7 | 0.1873 | 1.0716 | |
| 28 | | 0.1651 | 0.8756 | |
| 30 | | 1.0245 | 0.2668 | 36.491 |
| 35 | | 1.4612 | | 1 |
| 38 | | 0.4782 | 0.8323 | 16.36 |
| 39 | | 0.1114 | 0.9245 | 13.425 |
| 42 | 0.39 | | | |

What is claimed is:

1. A compound of Formula I

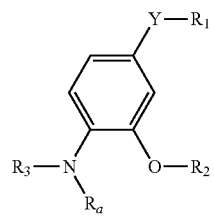

Formula I wherein

R$_1$ is selected from the group consisting of i) phenyl optionally substituted with one to two substituents independently selected from the group consisting of C$_{1-4}$alkyl, C$_{1-4}$alkoxy, C$_{1-4}$alkylthio, hydroxy, di($C_{1-4}$alkyl)aminocarbonyl, chloro, and fluoro; such that only one di($C_{1-4}$alkyl)aminocarbonyl is present;
ii) naphthyl;
iii) pyridinyl optionally substituted with one substituent selected from the group consisting of $C_{1-4}$alkyl, $C_{1-4}$alkoxy, $C_{1-4}$alkylthio, hydroxy, fluoro, chloro, and cyano;
iv) pyrimidin-5-yl;
v) furanyl;
vi) thienyl;
vii) 5-oxo-4,5-dihydro-[1,2,4]oxadiazol-3-yl; and
viii) di($C_{1-2}$alkyl)aminocarbonyl;
with the proviso that when $R_1$ is 5-oxo-4,5-dihydro-[1,2,4]oxadiazol-3-yl, Y is a bond;
Y is ethyl, vinyl, or a bond;
or, Y is O when $R_1$ is an optionally substituted phenyl;
$R_2$ is phenyl optionally substituted with one to two substituents independently selected from the group consisting of $C_{1-4}$alkyl, $C_{1-4}$alkoxy, fluoro, chloro, cyano, trifluoromethoxy, and hydroxy;
or, $R_2$ is phenyl substituted with one aminocarbonyl, di($C_{1-4}$alkyl)aminocarbonyl, $C_{1-4}$alkoxycarbonyl, or carboxy substituent;
$R_3$ is selected from the group consisting of
i) 3-amino-cyclohexyl;
ii) 4-amino-cyclohexyl;
iii) piperidin-3-yl;
iv) piperidin-4-yl;
v) pyrrolidin-2-ylmethyl wherein pyrrolidin-2-yl is optionally substituted at the 3- or 4- position with one to two fluoro substituents;
vi) azetidin-3-ylmethyl;
vii) 2-(N-methylamino)ethyl;
viii) 3-hydroxy-2-amino-propyl;
ix) piperidin-3-ylmethyl;
x) 1-azabicyclo[2.2.2]octan-3-yl; and
xi) 8-azabicyclo[3.2.1]octan-3-yl;
or, $R_3$ is taken with $R_a$ and the nitrogen atom to which they are both attached to form piperazinyl optionally substituted with 4-$C_{1-4}$alkyl;
$R_a$ is hydrogen, 2-(N-methylamino)ethyl, or $C_{1-2}$alkyl optionally substituted with azetidin-3-yl;
and enantiomers, diastereomers, and pharmaceutically acceptable salts thereof.

2. The compound of claim 1 wherein $R_1$ is selected from the group consisting of
i) phenyl optionally substituted with one to two substituents independently selected from the group consisting of $C_{1-4}$alkoxy, di($C_{1-4}$alkyl)aminocarbonyl, and fluoro; such that only one di($C_{1-4}$alkyl)aminocarbonyl is present;
ii) naphthyl;
iii) pyridinyl optionally substituted with one substituent selected from the group consisting of $C_{1-4}$alkyl, $C_{1-4}$alkoxy, $C_{1-4}$alkylthio, fluoro, and cyano;
iv) pyrimidin-5-yl;
v) furanyl;
vi) thienyl; and
vii) di($C_{1-2}$alkyl)aminocarbonyl.

3. The compound of claim 2 wherein $R_1$ is selected from the group consisting of
i) phenyl optionally substituted with one substituent selected from the group consisting of $C_{1-4}$alkoxy, di($C_{1-4}$alkyl)aminocarbonyl, and fluoro;
ii) pyridinyl optionally substituted with one substituent selected from the group consisting of $C_{1-4}$alkyl, $C_{1-4}$alkoxy, $C_{1-4}$alkylthio, fluoro, and cyano;
iii) pyrimidin-5-yl; and
iv) di($C_{1-2}$alkyl)aminocarbonyl.

4. The compound of claim 3 wherein $R_1$ is selected from the group consisting of
i) phenyl optionally substituted with one methoxy substituent;
ii) pyridinyl optionally substituted with one substituent selected from the group consisting of $C_{1-4}$alkyl, $C_{1-4}$alkoxy, $C_{1-4}$alkylthio, fluoro, and cyano;
iii) pyrimidin-5-yl; and
iv) di($C_{1-2}$alkyl)aminocarbonyl.

5. The compound of claim 1 wherein Y is vinyl or a bond; or, Y is O when $R_1$ is an optionally substituted phenyl.

6. The compound of claim 5 wherein Y is vinyl or a bond.

7. The compound of claim 1 wherein $R_2$ is phenyl optionally substituted with one
to two substituents independently selected from the group consisting of $C_{1-4}$alkyl, $C_{1-4}$alkoxy, fluoro, chloro, and hydroxy;
or, $R_2$ is phenyl substituted with one aminocarbonyl or di($C_{1-4}$alkyl)aminocarbonyl substituent.

8. The compound of claim 7 wherein $R_2$ is phenyl optionally substituted with one
to two substituents independently selected from the group consisting of $C_{1-4}$alkyl, $C_{1-4}$alkoxy, and hydroxy;
or, $R_2$ is phenyl substituted with one aminocarbonyl or di($C_{1-4}$alkyl)aminocarbonyl substituent.

9. The compound of claim 8 wherein $R_2$ is phenyl optionally substituted with one substituent independently selected from the group consisting of methoxy, hydroxy, aminocarbonyl, and $C_{1-4}$alkylcarbonylamino.

10. The compound of claim 1 wherein $R_3$ is selected from the group consisting of
i) 3-amino-cyclohexyl;
ii) 4-amino-cyclohexyl;
iii) pyrrolidin-2-ylmethyl wherein pyrrolidin-2-yl is optionally substituted at the 3- or 4- position with one to two fluoro substituents;
iv) 2-(N-methylamino)ethyl;
v) piperidin-3-ylmethyl; and
vi) 1-azabicyclo[2.2.2]octan-3-yl;
or, $R_3$ is taken with $R_a$ and the nitrogen atom to which they are both attached to form piperazinyl.

11. The compound of claim 10 wherein $R_3$ is selected from the group consisting of
i) 3-amino-cyclohexyl;
ii) 4-amino-cyclohexyl; and
iii) pyrrolidin-2-ylmethyl wherein pyrrolidin-2-yl is optionally substituted at the 3- or 4- position with one fluoro substituent;
or, $R_3$ is taken with $R_a$ and the nitrogen atom to which they are both attached to form piperazinyl.

12. The compound of claim 1 wherein $R_a$ is hydrogen or $C_{1-2}$alkyl.

13. The compound of claim 12 wherein $R_a$ is hydrogen.

14. A compound of Formula (I)

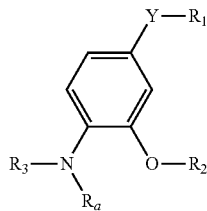

Formula (I)

wherein $R_1$ is selected from the group consisting of
i) phenyl optionally substituted with one to two substituents independently selected from the group consisting of $C_{1-4}$alkoxy, di($C_{1-4}$alkyl)aminocarbonyl, and fluoro; such that only one di($C_{1-4}$alkyl)aminocarbonyl is present;
ii) naphthyl;
iii) pyridinyl optionally substituted with one substituent selected from the group consisting of $C_{1-4}$alkyl, $C_{1-4}$alkoxy, $C_{1-4}$alkylthio, fluoro, and cyano;
iv) pyrimidin-5-yl;
v) furanyl;
vi) thienyl; and
vii) di($C_{1-2}$alkyl)aminocarbonyl;

Y is vinyl or a bond; or, Y is 0 when $R_1$ is an optionally substituted phenyl;

$R_2$ is phenyl optionally substituted with one to two substituents independently selected from the group consisting of $C_{1-4}$alkyl, $C_{1-4}$alkoxy, fluoro, chloro, and hydroxy;
or, $R_2$ is phenyl substituted with one aminocarbonyl or di($C_{1-4}$alkyl)aminocarbonyl substituent;

$R_3$ is selected from the group consisting of
i) 3-amino-cyclohexyl;
ii) 4-amino-cyclohexyl;
iii) pyrrolidin-2-ylmethyl wherein pyrrolidin-2-yl is optionally substituted at the 3- or 4- position with one to two fluoro substituents;2-(N -methylamino)ethyl;piperidin-3-ylmethyl; and
iv) 1-azabicyclo[2.2.2]octan-3-yl;
or, $R_3$ is taken with $R_a$ and the nitrogen atom to which they are both attached to form piperazinyl;

$R_a$ is hydrogen or $C_{1-2}$alkyl;

and enantiomers, diastereomers, and pharmaceutically acceptable salts thereof.

15. A compound of Formula (I)

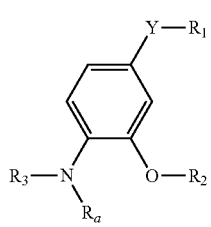

Formula (I)

wherein $R_1$ is selected from the group consisting of
i) phenyl optionally substituted with one substituent selected from the group consisting of $C_{1-4}$alkoxy, di($C_{1-4}$alkyl)aminocarbonyl, and fluoro;
ii) pyridinyl optionally substituted with one substituent selected from the group consisting of $C_{1-4}$alkyl, $C_{1-4}$alkoxy, $C_{1-4}$alkylthio, fluoro, and cyano;
iii) pyrimidin-5-yl; and
iv) di($C_{1-2}$alkyl)aminocarbonyl;

Y is vinyl or a bond;

$R_2$ is phenyl optionally substituted with one to two substituents independently selected from the group consisting of $C_{1-4}$alkyl, $C_{1-4}$alkoxy, and hydroxy; or, $R_2$ is phenyl substituted with one aminocarbonyl or di($C_{1-4}$alkyl)aminocarbonyl substituent;

$R_3$ is selected from the group consisting of
i) 3-amino-cyclohexyl;
ii) 4-amino-cyclohexyl;
iii) pyrrolidin-2-ylmethyl wherein pyrrolidin-2-yl is optionally substituted at a carbon atom with one to two fluoro substituents;
iv) 2-(N-methylamino)ethyl;
v) piperidin-3-ylmethyl; and
vi) 1-azabicyclo[2.2.2]octan-3-yl;
or, $R_3$ is taken with $R_a$ and the nitrogen atom to which they are both attached to form piperazinyl;

$R_a$ is hydrogen;

and enantiomers, diastereomers, and pharmaceutically acceptable salts thereof.

16. A compound of Formula (I)

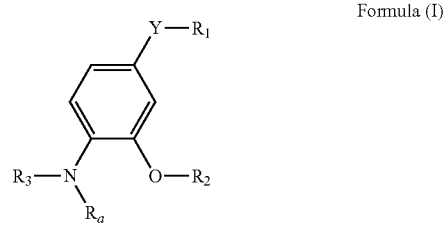

Formula (I)

wherein $R_1$ is selected from the group consisting of
i) phenyl optionally substituted with one methoxy substituent;
ii) pyridinyl optionally substituted with one substituent selected from the group consisting of $C_{1-4}$alkyl, $C_{1-4}$alkoxy, $C_{1-4}$alkylthio, fluoro, and cyano;
iii) pyrimidin-5-yl; and
iv) di($C_{1-2}$alkyl)aminocarbonyl;

Y is vinyl or a bond;

$R_2$ is phenyl optionally substituted with one substituent independently selected from the group consisting of methoxy, hydroxy, aminocarbonyl, and $C_{1-4}$alkylcarbonylamino;

$R_3$ is selected from the group consisting of
i) 3-amino-cyclohexyl;
ii) 4-amino-cyclohexyl;
iii) pyrrolidin-2-ylmethyl wherein pyrrolidin-2-yl is optionally substituted at a carbon atom with one fluoro substituent; and
or, $R_3$ is taken with $R_a$ and the nitrogen atom to which they are both attached to form piperazinyl;

$R_a$ is hydrogen;

and enantiomers, diastereomers, and pharmaceutically acceptable salts thereof.

17. A compound of Formula (I)

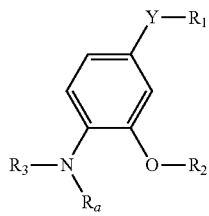

Formula (I)

selected from the group consisting of
a compound wherein $R_1$ is 2-(N,N-diethylaminocarbonyl), Y is (E)-vinyl, $R_2$ is 4-methoxy-phenyl, $R_3$ is pyrrolidin-2-ylmethyl, and $R_a$ is H; (2S)
a compound wherein $R_1$ is 2-(N,N-diethylaminocarbonyl), Y is ethyl, $R_2$ is 4-methoxy-phenyl, $R_3$ is pyrrolidin-2-ylmethyl, and $R_a$ is H; (2S)
a compound wherein $R_1$ is 2-(4-methoxy-phenyl), Y is ethyl, $R_2$ is 4-methoxy-phenyl, $R_3$ is pyrrolidin-2-ylmethyl, and $R_a$ is H; (2S)
a compound wherein $R_1$ is 2-(3-methoxy-phenyl), Y is ethyl, $R_2$ is 4-methoxy-phenyl, $R_3$ is pyrrolidin-2-ylmethyl, and $R_a$ is H; (2S)
a compound wherein $R_1$ is 2-phenyl, Y is ethyl, $R_2$ is 4-methoxy-phenyl, $R_3$ is pyrrolidin-2-ylmethyl, and $R_a$ is H; (2S)
a compound wherein $R_1$ is 2-(4-fluoro-phenyl), Y is ethyl, $R_2$ is 4-methoxy-phenyl, $R_3$ is pyrrolidin-2-ylmethyl, and $R_a$ is H; (2S)
a compound wherein $R_1$ is 2-(3-fluoro-phenyl), Y is ethyl, $R_2$ is 4-methoxy-phenyl, $R_3$ is pyrrolidin-2-ylmethyl, and $R_a$ is H; (2S)
a compound wherein $R_1$ is 2-[3-(N,N-diethylaminocarbonyl)phenyl], Y is ethyl, $R_2$ is 4-methoxy-phenyl, $R_3$ is pyrrolidin-2-ylmethyl, and $R_a$ is H; (2S)
a compound wherein $R_1$ is N,N-diethylaminocarbonyl, Y is a bond, $R_2$ is phenyl, $R_3$ is pyrrolidin-2-ylmethyl, and $R_a$ is H; (2S)
a compound wherein $R_1$ is N,N-diethylaminocarbonyl, Y is a bond, $R_2$ is 4-methoxy-phenyl, $R_3$ is pyrrolidin-2-ylmethyl, and $R_a$ is H; (2S)
a compound wherein $R_1$ is N,N-diethylaminocarbonyl, Y is a bond, $R_2$ is 2-methoxy-phenyl, $R_3$ is pyrrolidin-2-ylmethyl, and $R_a$ is H; (2S)
a compound wherein $R_1$ is phenyl, Y is a bond, $R_2$ is 4-cyano-phenyl, $R_3$ is pyrrolidin-2-ylmethyl, and $R_a$ is H; (2S)
a compound wherein $R_1$ is phenyl, Y is a bond, $R_2$ is 3-cyano-phenyl, $R_3$ is pyrrolidin-2-ylmethyl, and $R_a$ is H; (2S)
a compound wherein $R_1$ is phenyl, Y is a bond, $R_2$ is phenyl, $R_3$ is pyrrolidin-2-ylmethyl, and $R_a$ is H; (2S)
a compound wherein $R_1$ is phenyl, Y is a bond, $R_2$ is 3-methoxy-phenyl, $R_3$ is pyrrolidin-2-ylmethyl, and $R_a$ is H; (2S)
a compound wherein $R_1$ is phenyl, Y is a bond, $R_2$ is 4-fluoro-phenyl, $R_3$ is pyrrolidin-2-ylmethyl, and $R_a$ is H; (2S)
a compound wherein $R_1$ is phenyl, Y is a bond, $R_2$ is 4-trifluoromethoxy-phenyl, $R_3$ is pyrrolidin-2-ylmethyl, and $R_a$ is H; (2S)
a compound wherein $R_1$ is phenyl, Y is a bond, $R_2$ is 2,6-dichloro-phenyl, $R_3$ is pyrrolidin-2-ylmethyl, and $R_a$ is H; (2S)
a compound wherein $R_1$ is phenyl, Y is a bond, $R_2$ is 4-methoxy-phenyl, $R_3$ is 2-(N-methylamino)ethyl, and $R_a$ is H;
a compound wherein $R_1$ is phenyl, Y is a bond, $R_2$ is 4-methoxycarbonyl-phenyl, $R_3$ is pyrrolidin-2-ylmethyl, and $R_a$ is H; (2S)
a compound wherein $R_1$ is phenyl, Y is a bond, $R_2$ is 3-methoxycarbonyl-phenyl, $R_3$ is pyrrolidin-2-ylmethyl, and $R_a$ is H; (2S)
a compound wherein $R_1$ is phenyl, Y is a bond, $R_2$ is 2,4-dichloro-phenyl, $R_3$ is pyrrolidin-2-ylmethyl, and $R_a$ is H; (2S)
a compound wherein $R_1$ is phenyl, Y is a bond, $R_2$ is 4-methoxy-phenyl, $R_3$ is piperidin-4-yl, and $R_a$ is H;
a compound wherein $R_1$ is 5-cyano-pyridin-3-yl, Y is a bond, $R_2$ is 4-methoxy-phenyl, $R_3$ is 4-fluoro-pyrrolidin-2-ylmethyl, and $R_a$ is H; (2S,4R)
a compound wherein $R_1$ is 5-fluoro-pyridin-3-yl, Y is a bond, $R_2$ is 4-methoxy-phenyl, $R_3$ is 4-fluoro-pyrrolidin-2-ylmethyl, and $R_a$ is H; (2S,4R)
a compound wherein $R_1$ is 5-methylthio-pyridin-3-yl, Y is a bond, $R_2$ is 4-methoxy-phenyl, $R_3$ is 4-fluoro-pyrrolidin-2-ylmethyl, and $R_a$ is H; (2S,4R)
a compound wherein $R_1$ is 5-methoxy-pyridin-3-yl, Y is a bond, $R_2$ is 4-methoxy-phenyl, $R_3$ is 4-fluoro-pyrrolidin-2-ylmethyl, and $R_a$ is H; (2S,4R)
a compound wherein $R_1$ is 5-methyl-pyridin-3-yl, Y is a bond, $R_2$ is 4-methoxy-phenyl, $R_3$ is 4-fluoro-pyrrolidin-2-ylmethyl, and $R_a$ is H; (2S,4R)
a compound wherein $R_1$ is phenyl, Y is a bond, $R_2$ is 4-aminocarbonyl-phenyl, $R_3$ is pyrrolidin-2-ylmethyl, and $R_a$ is H; (2S)
a compound wherein $R_1$ is phenyl, Y is a bond, $R_2$ is 3-aminocarbonyl-phenyl, $R_3$ is pyrrolidin-2-ylmethyl, and $R_a$ is H; (2S)
a compound wherein $R_1$ is phenyl, Y is a bond, $R_2$ is 4-carboxy-phenyl, $R_3$ is pyrrolidin-2-ylmethyl, and $R_a$ is H; (2S)
a compound wherein $R_1$ is phenyl, Y is a bond, $R_2$ is 3-carboxy-phenyl, $R_3$ is pyrrolidin-2-ylmethyl, and $R_a$ is H; (2S)
a compound wherein $R_1$ is phenyl, Y is a bond, $R_2$ is 4-(N,N-diethylaminocarbonyl)phenyl, $R_3$ is pyrrolidin-2-ylmethyl, and $R_a$ is H; (2S)
a compound wherein $R_1$ is phenyl, Y is a bond, $R_2$ is 3-(N,N-diethylaminocarbonyl)phenyl, $R_3$ is pyrrolidin-2-ylmethyl, and $R_a$ is H; (2S)
a compound wherein $R_1$ is phenyl, Y is a bond, $R_2$ is 4-methoxy-phenyl, $R_3$ is pyrrolidin-2-ylmethyl, and $R_a$ is H; (2S)
a compound wherein $R_1$ is naphthalen-2-yl, Y is a bond, $R_2$ is 4-methoxy-phenyl, $R_3$ is pyrrolidin-2-ylmethyl, and $R_a$ is H; (2S)
a compound wherein $R_1$ is naphthalen-1-yl, Y is a bond, $R_2$ is 4-methoxy-phenyl, $R_3$ is pyrrolidin-2-ylmethyl, and $R_a$ is H; (2S)
a compound wherein $R_1$ is pyridin-4-yl, Y is a bond, $R_2$ is 4-methoxy-phenyl, $R_3$ is pyrrolidin-2-ylmethyl, and $R_a$ is H; (2S)
a compound wherein $R_1$ is pyridin-3-yl, Y is a bond, $R_2$ is 4-methoxy-phenyl, $R_3$ is pyrrolidin-2-ylmethyl, and $R_a$ is H; (2S)
a compound wherein $R_1$ is furan-3-yl, Y is a bond, $R_2$ is 4-methoxy-phenyl, $R_3$ is pyrrolidin-2-ylmethyl, and $R_a$ is H; (2S)
a compound wherein $R_1$ is thiophen-3-yl, Y is a bond, $R_2$ is 4-methoxy-phenyl, $R_3$ is pyrrolidin-2-ylmethyl, and $R_a$ is H; (2S) a compound wherein $R_1$ is pyrimidin-5-yl, Y is a bond, $R_2$ is 4-methoxy-phenyl, $R_3$ is pyrrolidin-2-ylmethyl, and $R_a$ is H; (2S)

a compound wherein $R_1$ is 5-fluoro-pyridin-3-yl, Y is a bond, $R_2$ is 4-methoxy-phenyl, $R_3$ is pyrrolidin-2-ylmethyl, and $R_a$ is H; (2S)

a compound wherein $R_1$ is 5-cyano-pyridin-3-yl, Y is a bond, $R_2$ is 4-methoxy-phenyl, $R_3$ is pyrrolidin-2-ylmethyl, and $R_a$ is H; (2S)

a compound wherein $R_1$ is pyridin-3-yl, Y is a bond, $R_2$ is 4-hydroxy-phenyl, $R_3$ is pyrrolidin-2-ylmethyl, and $R_a$ is H; (2S)

a compound wherein $R_1$ is phenyl, Y is a bond, $R_2$ is 4-methoxy-phenyl, $R_3$ is taken with $R_a$ and the nitrogen atom to which they are both attached to form piperazin-1-yl;

a compound wherein $R_1$ is phenyl, Y is a bond, $R_2$ is 4-methoxy-phenyl, $R_3$ is taken with $R_a$ and the nitrogen atom to which they are both attached to form 4-methyl-piperazin-1-yl;

a compound wherein $R_1$ is 5-oxo-4,5-dihydro-[1,2,4]oxadiazol-3-yl, Y is a bond, $R_2$ is 4-methoxy-phenyl, $R_3$ is pyrrolidin-2-ylmethyl, and $R_a$ is H; (2S)

a compound wherein $R_1$ is pyridin-3-yl, Y is a bond, $R_2$ is 4-methoxy-phenyl, $R_3$ is pyrrolidin-2-ylmethyl, and $R_a$ is ethyl; (2S)

a compound wherein $R_1$ is 5-fluoro-pyridin-3-yl, Y is a bond, $R_2$ is 4-methoxy-phenyl, $R_3$ is pyrrolidin-2-ylmethyl, and $R_a$ is ethyl; (2S)

a compound wherein $R_1$ is pyrimidin-5-yl, Y is a bond, $R_2$ is 4-methoxy-phenyl, $R_3$ is pyrrolidin-2-ylmethyl, and $R_a$ is ethyl; (2S)

a compound wherein $R_1$ is 5-cyano-pyridin-3-yl, Y is a bond, $R_2$ is 4-methoxy-phenyl, $R_3$ is pyrrolidin-2-ylmethyl, and $R_a$ is ethyl; (2S)

a compound wherein $R_1$ is 4-methoxy-phenyl, Y is 0, $R_2$ is 4-methoxy-phenyl, $R_3$ is pyrrolidin-2-ylmethyl, and $R_a$ is H; (2S)

a compound wherein $R_1$ is 4-methoxy-phenyl, Y is 0, $R_2$ is 4-methoxy-phenyl, $R_3$ is piperidin-3-yl, and $R_a$ is H; racemic;

a compound wherein $R_1$ is 4-methoxy-phenyl, Y is 0, $R_2$ is 4-methoxy-phenyl, $R_3$ is 3-hydroxy-2(R)-amino-propyl, and $R_a$ is H;

a compound wherein $R_1$ is 4-methoxy-phenyl, Y is 0, $R_2$ is 4-methoxy-phenyl, $R_3$ is piperidin-4-yl, and $R_a$ is H;

a compound wherein $R_1$ is 4-methoxy-phenyl, Y is 0, $R_2$ is 4-methoxy-phenyl, $R_3$ is 8-azabicyclo[3.2.1]octan-3-yl, and $R_a$ is H; mixture of endo/exo isomers;

a compound wherein $R_1$ is 4-methoxy-phenyl, Y is 0, $R_2$ is 4-methoxy-phenyl, $R_3$ is azetidin-3-yl-methyl, and $R_a$ is H;

a compound wherein $R_1$ is 4-methoxy-phenyl, Y is 0, $R_2$ is 4-methoxy-phenyl, $R_3$ is azetidin-3-yl-methyl, and $R_a$ is azetidin-3-yl-methyl;

a compound wherein $R_1$ is 4-methoxy-phenyl, Y is 0, $R_2$ is 4-methoxy-phenyl, $R_3$ is 1-azabicyclo[2.2.2]octan-3-yl, and $R_a$ is H; mixture of endo/exo isomers;

a compound wherein $R_1$ is 4-methoxy-phenyl, Y is 0, $R_2$ is 4-methoxy-phenyl, $R_3$ is piperidin-3-ylmethyl, and $R_a$ is H; racemic;

a compound wherein $R_1$ is 4-methoxy-phenyl, Y is 0, $R_2$ is 4-methoxy-phenyl, $R_3$ is 3-amino-cyclohexyl, and $R_a$ is H; mixture of 4 isomers;

a compound wherein $R_1$ is 4-methoxy-phenyl, Y is 0, $R_2$ is 4-methoxy-phenyl, $R_3$ is 2-(N-methylamino)ethyl, and $R_a$ is H; and a compound wherein $R_1$ is 4-methoxy-phenyl, Y is 0, $R_2$ is 4-methoxy-phenyl, $R_3$ is 2-(N-methylamino)ethyl, and $R_a$ is 2-(N-methylamino)ethyl;

and pharmaceutically acceptable salts thereof.

18. A pharmaceutical composition comprising a compound of claim 1 and at least one of a pharmaceutically acceptable carrier, a pharmaceutically acceptable excipient, and a pharmaceutically acceptable diluent.

19. The pharmaceutical composition of claim 18, wherein the composition is a solid, oral dosage form.

20. The pharmaceutical composition of claim 18, wherein the composition is a syrup, an elixir, or a suspension.

21. A method for treating mild to severe pain in a subject in need thereof, comprising administering to the subject a therapeutically effective amount of a compound of claim 1.

22. The method of claim 21 wherein the mild to severe pain is due to a disease or condition selected from the group consisting of osteoarthritis, rheumatoid arthritis, fibromyalgia, migraine, headache, toothache, burn, sunburn, snake bite, spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulitis, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

23. The method of claim 21 wherein the pain is selected from the group consisting of inflammatory pain, centrally mediated pain, peripherally mediated pain, visceral pain, structural related pain, cancer pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

24. A method for treating depression, said method comprising the step of administering to a mammal in need of such treatment a therapeutically effective amount of a compound, or salt of claim 1.

* * * * *